US012662524B2

(12) United States Patent
Sahu et al.

(10) Patent No.: US 12,662,524 B2
(45) Date of Patent: Jun. 23, 2026

(54) DAF-MCP CHIMERIC PROTEINS, PROCESS TO MANUFACTURE THE SAME AND USE OF THE CHIMERIC PROTEIN FOR TREATING PATHOLOGICAL CONDITIONS INVOLVING THE COMPLEMENT SYSTEM

(71) Applicant: NATIONAL CENTRE FOR CELL SCIENCE, Maharashtra (IN)

(72) Inventors: Arvind Sahu, Maharashtra (IN); Hemendra Singh Panwar, Maharashtra (IN); Hina Ojha, Maharashtra (IN); Payel Ghosh, Maharashtra (IN); Sagar H. Barage, Maharashtra (IN)

(73) Assignee: NATIONAL CENTRE FOR CELL SCIENCE, Maharashtra (IN)

( * ) Notice: Subject to any disclaimer, the term of this patent is extended or adjusted under 35 U.S.C. 154(b) by 1202 days.

(21) Appl. No.: 17/603,444

(22) PCT Filed: Apr. 9, 2020

(86) PCT No.: PCT/IN2020/050337

§ 371 (c)(1),
(2) Date: Oct. 13, 2021

(87) PCT Pub. No.: WO2020/213004

PCT Pub. Date: Oct. 22, 2020

(65) Prior Publication Data

US 2022/0195012 A1     Jun. 23, 2022

(30) Foreign Application Priority Data

Apr. 13, 2019     (IN) .............................. 201921014960

(51) Int. Cl.
*C07K 14/705*     (2006.01)
*A61K 38/00*     (2006.01)

(52) U.S. Cl.
CPC ........ *C07K 14/70596* (2013.01); *A61K 38/00* (2013.01)

(58) Field of Classification Search
CPC ............................................... C07K 14/70596
See application file for complete search history.

(56) References Cited

U.S. PATENT DOCUMENTS

| | | | |
|---|---|---|---|
| 5,851,528 A | 12/1998 | Ko et al. | |
| 5,866,402 A | 2/1999 | Innis et al. | |
| 8,932,601 B2 | 1/2015 | Medof et al. | |
| 2008/0188404 A1 * | 8/2008 | Medof ............. | C07K 14/70596 435/320.1 |

FOREIGN PATENT DOCUMENTS

| | | |
|---|---|---|
| CN | 1390938 | 1/2003 |
| WO | 95/08570 | 3/1995 |

OTHER PUBLICATIONS

Andersson, Jonas, et al. "Binding of a model regulator of complement activation (RCA) to a biomaterial surface: surface-bound factor H inhibits complement activation." Biomaterials 22(17) (2001): 2435-2443. (Year: 2001).*
Ekdahl, Kristina N., et al. "Therapeutic regulation of complement activation in extracorporeal circuits and intravascular treatments with special reference to the alternative pathway amplification loop." Immunological Reviews 313(1) (2023): 91-103. (Year: 2023).*
International Search Report issued Aug. 27, 2020 in International (PCT) Application No. PCT/IN2020/050337.
Written Opinion dated Aug. 27, 2020 in International (PCT) Application No. PCT/IN2020/050337.
Tulika et al., "Cloning, Expression and Functional Analysis of D2D3 domains of Decay Accelerating Factor (DAF)", 1st International Conference on Human Implications of Biotechnology, 2016, pp. 55-56.
Christiansen, Dale et al., "Chimeric CD46/DAF molecules reveal a cryptic functional role for SCR1 of DAF in regulating complement activation", Molecular Immunology, 2000, vol. 37, pp. 687-696.

* cited by examiner

*Primary Examiner* — Gary B Nickol
*Assistant Examiner* — Bryan William Heck
(74) *Attorney, Agent, or Firm* — Wenderoth, Lind & Ponack, L.L.P.

(57) ABSTRACT

The complement system is part of the innate immune system and is highly regulated by regulatory proteins belonging to the Regulators of Complement Activation (RCA) family. It is known that lack of regulation causes damage to host cells and deficiencies in the regulation is also linked to diseases such as age-related macular degeneration, atypical hemolytic uremic syndrome, and dense deposit disease. The regulatory proteins primarily include decay-accelerating factor (DAF; CD55), membrane cofactor protein (MCP; CD46), complement receptor 1 (CR1; CD35), factor H (FH) and C4b-binding protein (C4BP). Structurally, these proteins are composed of repeating complement control protein (CCP) domains where 2-4 successive domains contribute to the regulatory functions termed as decay-accelerating activity (DAA) and cofactor activity (CFA). However, no four-domain chimeric protein currently exists having both strong DAA (CP-DAA and AP-DAA) and strong CFA (C3b-CFA and C4b-CFA). Therefore, chimeric protein DCP (i.e., a dual-activity regulator) was created.

10 Claims, 25 Drawing Sheets
(18 of 25 Drawing Sheet(s) Filed in Color)

Specification includes a Sequence Listing.

A : Interaction of DAF domains in D2D3M3M4 with C3b
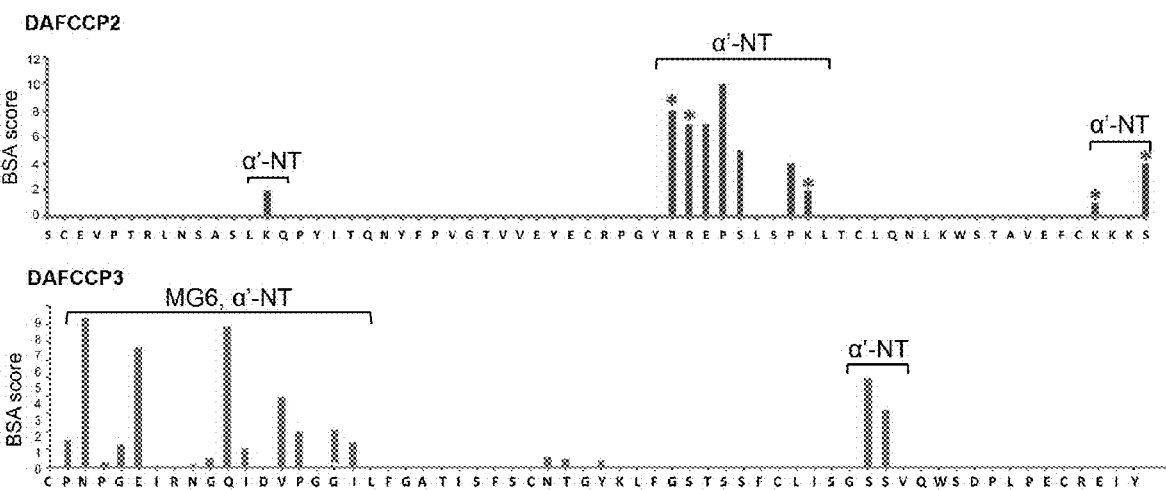
B : Interaction of DAF domains D2D3M3M4 with VWA domain in Bb
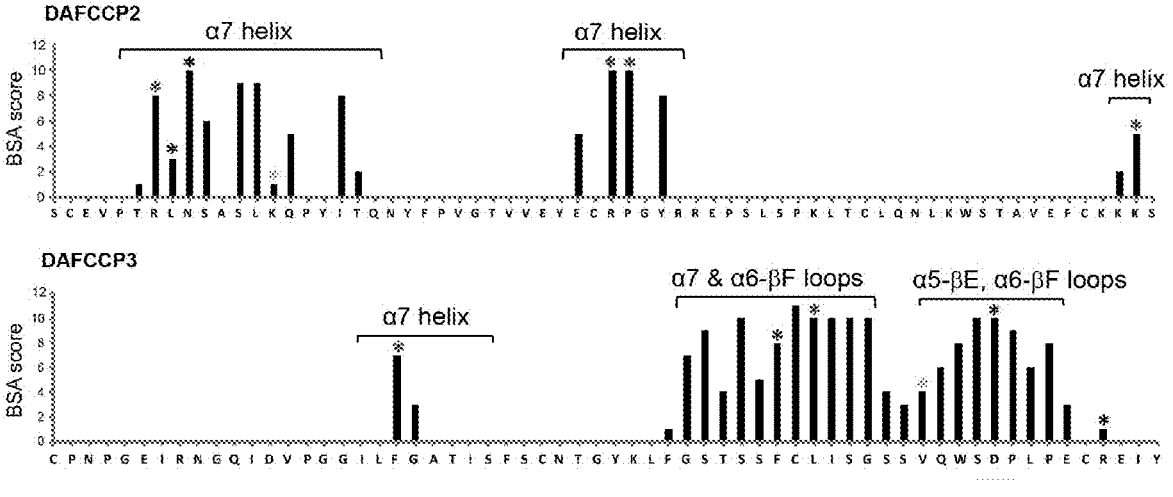
Figure 7 i ii

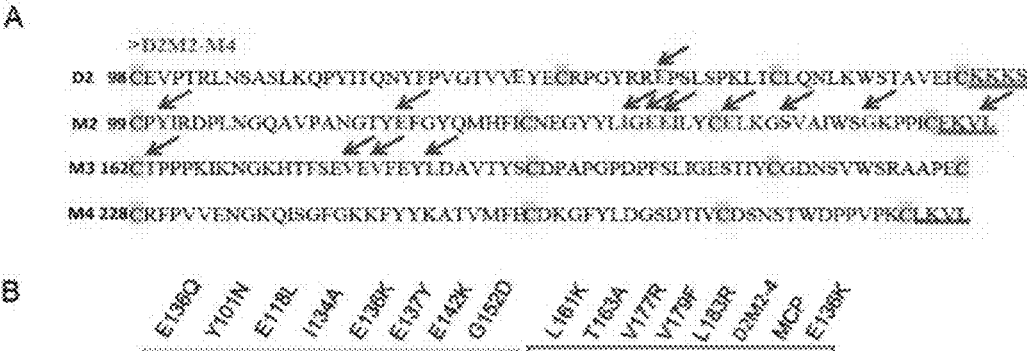

A

>D2M2-M4

D2  CEVPTRLNSASLKQPYTIQNYFPVGTVVEYECRPGYRREPSLSPKLICLQNLKWSTAVEFCKK

M2  CPYTRDPLNGQAVPANGTYEFGYDMRFICNEGYYLIGEEILYCELKGSVAIWSGKPPICEKVL

M3  CTPPPKIKNGKHTFSEYEVFEYLDAVTYSCDPAPGPDPFSLIGESTIYCGDNSVWSRAAPEC

M4  CRFPVVENGKQISGFGKKFYYKATVMFECDKGFYLDGSDTIVECDSNSTWDPPVPKCLKVL

B

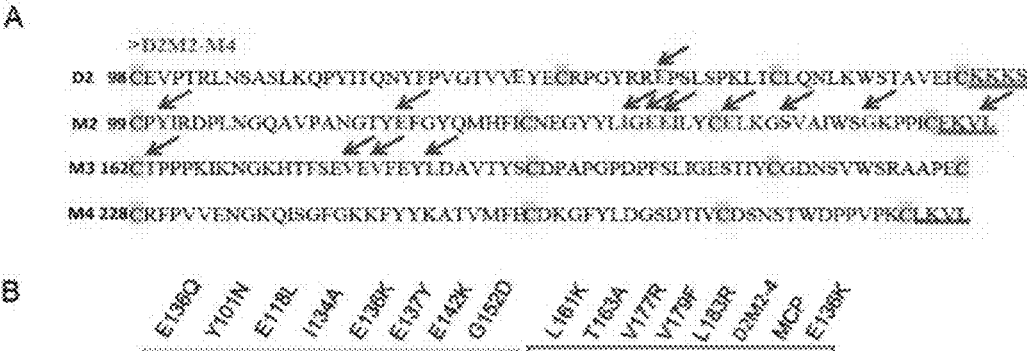

C

| Mutation | Based on the mutation data of regulator * | Domain of D2M2-4 |
|----------|-------------------------------------------|------------------|
| 1. E136Q | DAF | D2 |
| 2. Y101N | DAF | M2 |
| 3. E118L | DAF | M2 |
| 4. I134A | DAF | M2 |
| 5. E136K | sCCPH | M2 |
| 6. E137Y | SPICE | M2 |
| 7. E142K | DAF | M2 |
| 8. G152D | DAF | M2 |
| 9. L161K | Kaposica | M2-M3 linker |
| 10. T163A | MCP | M3 |
| 11. V177R | DAF, sCCPH | M3 |
| 12. V179F | sCCPH | M3 |
| 13. L183R | DAF | M3 |

Figure 16

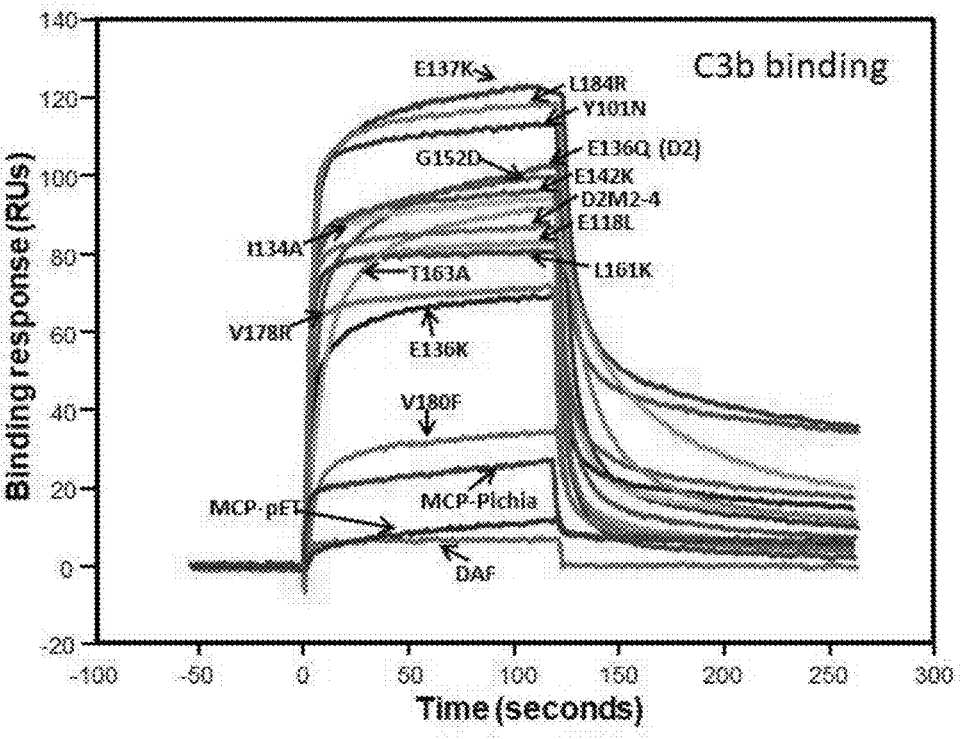
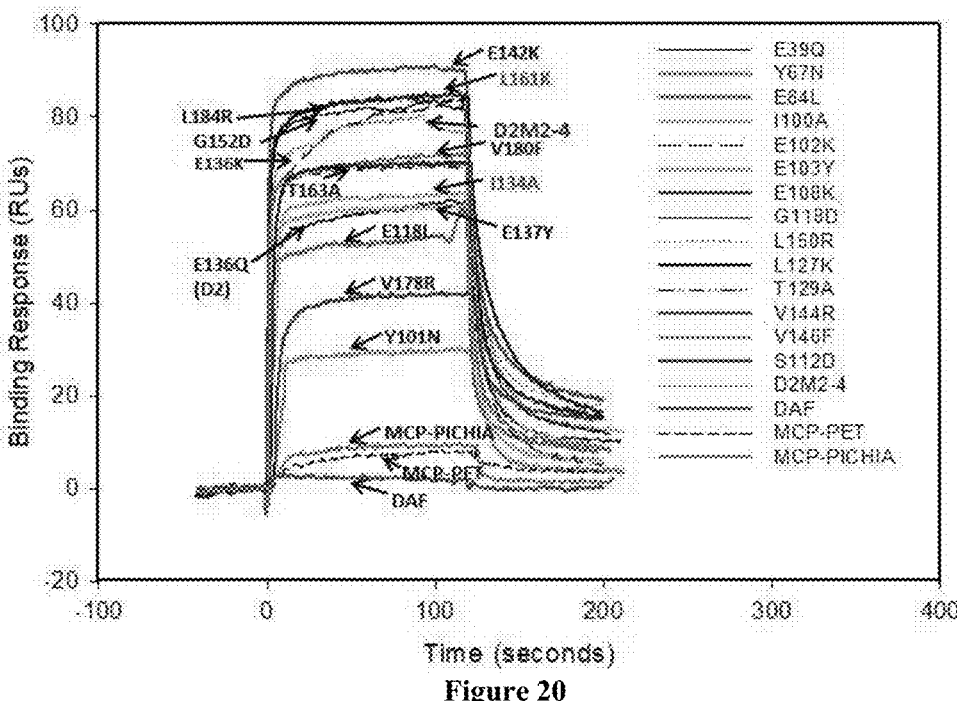
Figure 20

A    C3b-CFA
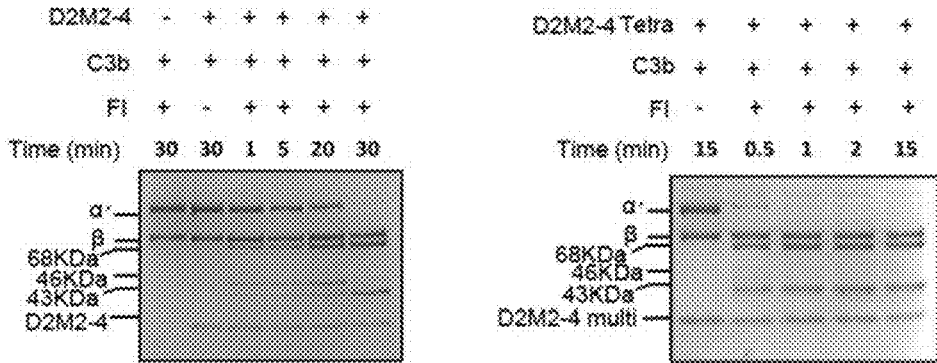
B    C4b-CFA
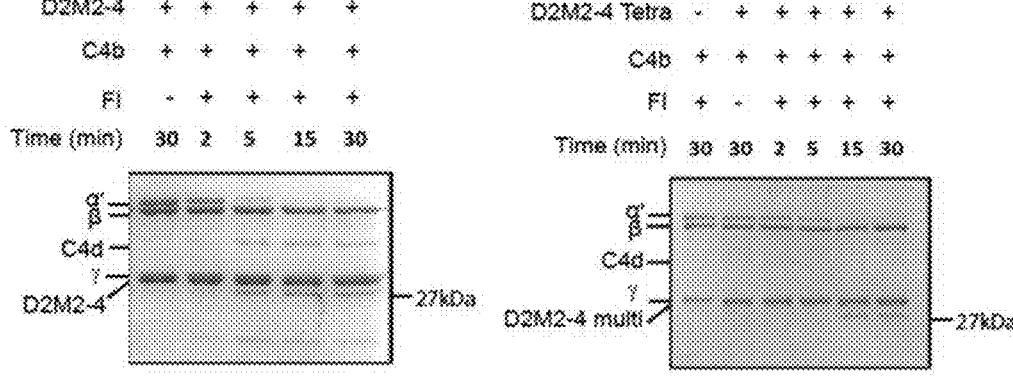
Figure 22

DAF-MCP CHIMERIC PROTEINS, PROCESS TO MANUFACTURE THE SAME AND USE OF THE CHIMERIC PROTEIN FOR TREATING PATHOLOGICAL CONDITIONS INVOLVING THE COMPLEMENT SYSTEM

SEQUENCE LISTING

A sequence listing in electronic (ASCII text file) format is filed with this application and incorporated herein by reference. The name of the ASCII text file is "2021-2141A_ST25.txt"; the file was created on Jul. 10, 2025; the size of the file is 103,390 bytes.

FIELD OF THE INVENTION

The present invention relates generally to the field of biotechnology. In particular, the present invention relates to a novel genetically modified four domain DAF-MCP chimeric proteins with dual-activity regulatory action and further modified for enhancing affinity towards factor I and avidity towards C3b/C4b (Chimeric protein DCP) and process for manufacturing the novel genetically modified four domain DAF-MCP chimeric protein.

BACKGROUND OF THE INVENTION

The complement system is a part of the innate immune system known for the role such as its direct action on pathogens, boosting the pathogenic-specific adaptive immune responses, contribution in processes of cell differentiation and polarization, tissue regeneration, lipid metabolism, clearing of immune complexes and apoptosis etc. Lack of regulation of complement activation or inappropriate activation results in damage to host tissues and therefore the complement system is tightly regulated by a series of proteins. Among these, the Regulators of Complement Activation (RCA) family proteins are majorly responsible for complement regulation. The RCA proteins include membrane proteins such as decay-accelerating factor (DAF; CD55), membrane cofactor protein (MCP; CD46), and complement receptor 1 (CR1; CD35) as well as fluid phase proteins such as factor H (FH) and C4b-binding protein (C4BP). Structurally, the RCA proteins are composed of repeating complement control protein (CCP) modules where 2-4 successive modules contribute to the regulatory functions termed as decay-accelerating activity (DAA) and cofactor activity (CFA). The RCA proteins function by targeting the C3/C5-convertases, which are the central enzymes of the complement pathways. For inactivation of these enzymes, the RCA proteins bind to these convertases or their non-catalytic subunits and inactivate them. In DAA, the RCA protein binds to the convertase and irreversibly dissociates it into its subunits, while in CFA, the RCA protein binds to the non-catalytic subunit of the convertase (C3b/C4b) and recruits serine protease factor I (FI) to cleave and inactivate it, thus ceasing its ability to form C3 convertase.

Activation of the complement system is initiated by three major pathways named as the lectin, classical and alternative pathways which converge at the C3 convertases (C4b2a or C3bBb) formation. These enzymes cleave complement component C3, which is necessary for initiation of all the downstream effector functions of complement. The C3 convertases are composed of two subunits wherein a catalytic subunit (Bb/C2a) is bound to a non-catalytic (C3b/C4b) subunit in an $Mg^{++}$-dependent manner.

The widely expressed membrane regulators of the RCA family proteins which protect the host cells from autologous complement attack are DAF and MCP. DAF dissociates C3 convertases through its DAA, while MCP prevents C3 convertases formation via its CFA. DAF and MCP are composed of four CCP modules each, which are arranged in an extended fashion. It is known that CCP2-4 domains of DAF are sequentially similar to CCP1-3 of MCP. Domain-deletion and site-directed mutagenesis studies in DAF demonstrated that CCP2-3 of DAF are required for its ability to decay the classical/lectin pathway C3 convertase (CP-DAA), and CCP2-4 are essential for the decay of the alternative pathway C3 convertase (AP-DAA). In MCP, domain deletion and site-directed mutagenesis data implicated CCP2-4 in CFA against C3b (C3b-CFA) and C4b (C4b-CFA). Further, the recent crystal structures of DAF and MCP in complex with C3b revealed that they bind through a common binding mode and CCP3-4 of these proteins form contact with C3b. However, the smallest structural unit of DAF required for imparting DAA, and the functional significance of each of its domain in DAA, and similarly the minimal FI interaction sites on MCP essential for imparting CFA against C3b and C4b are not currently known. Also, whether the presence of functional modularity exists in these proteins is not known, i.e., whether individual CCPs or multi-CCP units can impart a specific function to the protein and joining them would add new functional capabilities.

Prior art documents such as U.S. Pat. No. 5,866,402 claims chimeric protein sequences from MCP and DAF along with peptides sequences capable of binding glycosaminoglycans. Further, prior art documents EP 8932601B2 discloses a hybrid having structure $1^{st}$ Functional (Fn) unit-spacer-$2^{nd}$ Fn unit-spacer-$3^{rd}$ Fn unit where the complement Fn units can be either DAF and/or MCP and/or CR1 and/or non-complement functional units such as Ig and/or protein for enhancing binding to the animal cell. It also mentions several hybrids such as DAF-CRIB, DAF-CR1 BB, and DAF-IgG4 and a DAF-MCP hybrid having (DAF CCPs 1,2,3,4-CR1 CCPs 4,5,6,7-MCP CCPs 1,2,3, 4+2 amino acids (VS) of MCP STP region+6×His). U.S. Pat. No. 5,851,528 discloses polypetides which inhibit complement activity. US'528 does not specify the type of the regulatory activity or the mechanism of action of the said peptides.

However, none of the prior art discloses a four-domain DAF-MCP chimeric mutant containing DAA and CFA equivalent to that of the parent proteins with dual-activity regulatory action, which is achieved by enhancing affinity towards factor I and avidity towards C3b/C4b.

It is known that defects in the functioning of these RCA proteins are linked to various diseases such as age-related macular degeneration (AMD), atypical hemolytic uremic syndrome (aHUS), and dense deposit disease (DDD). The present invention is for a four-domain DAF-MCP chimeric mutant (DCP) containing DAA and CFA equivalent to that of the parent proteins with dual-activity regulatory action that was achieved by enhancing affinity towards factor I and avidity towards C3b/C4b. DCP may serve as a lead molecule for developing RCA-based therapeutics for treating pathological conditions involving the complement system.

Therefore, to test the above unknown factors four CCP DAF-MCP chimeras were generated and biochemically characterized. Further, the site-directed mutants of the four CCP DAF-MCP chimeras were generated and biochemically characterised. The resulting experiments and their data demonstrated the functional role of individual modules of DAF and MCP in a structural framework of four contiguous CCPs. Additionally, DAF-MCP chimeric mutant containing DAA and CFA equivalent to that of the parent proteins was constructed and thereby revealing the existence of functional modularity in RCA proteins.

Furthermore, the experimental data also provides mechanistic insight into both the regulatory activities.

OBJECT OF THE INVENTION

An object of the invention is to provide engineered chimeric proteins for inhibition of complement pathways. Another object of the invention is to provide a modified four domain DAF-MCP chimeric protein for dual-activity regulation and its further modification for enhancing affinity towards factor I and avidity towards C3b/C4b (i.e., creation of DCP), a process to manufacture the novel genetically modified four domain DAF-MCP chimeric protein and uses of DCP.

SUMMARY OF THE INVENTION

The complement system is an integral part of the innate immune system. It is highly regulated by regulatory proteins belonging to the Regulators of Complement Activation (RCA) family and lack of regulation causes damage to host cells and deficiencies in the regulation is linked to diseases such as age-related macular degeneration (AMD), atypical hemolytic uremic syndrome (aHUS), and dense deposit disease (DDD). Currently, there are no efficient four domain DAF-MCP chimeras that effectively have dual regulatory activity, and there is a need for a robust molecule/chimeric protein. The RCA proteins include membrane-tethered complement regulators decay-accelerating factor (DAF; CD55), membrane cofactor protein (MCP; CD46), and complement receptor 1 (CR1; CD35) and fluid-phase regulators such as factor H (FH) and C4b-binding protein (C4BP). Structurally, these proteins are composed of repeating complement control protein (CCP) domains where 2-4 successive domains contribute to the regulatory functions termed as decay-accelerating activity (DAA) and cofactor activity (CFA) and current DAF-MCP chimeras with dual activity have 8 CCP domains. However, there is no four-domain chimeric protein currently that has both strong DAA and strong CFA. Therefore, the present invention is for a four-domain Chimeric protein DCP (i.e., a dual-activity regulator) created to have dual activity regulation (i.e., DAA and CFA) with enhanced affinity/interaction with factor I and avidity for C3b/C4b, the process to manufacture the novel genetically modified four domain DAF-MCP chimeric protein and uses of DCP and the use of DCP for commercial use.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is the Diagrammatic representation of DAF, MCP and the DAF-MCP chimeras. The red linkers denote the linkers connecting the DAF domains, and the blue linkers denote the linkers connecting the MCP domains; the same colour scheme is used to depict the linkers in the DAF-MCP chimeras. FIG. 1B depicts the Upper panel—SDS-PAGE analysis of DAF, MCP and the DAF-MCP chimeras expressed in *Pichia* and Lower panel—SDS-PAGE analysis of DAF, DAF mutant D2D3 and the DAF-MCP chimeras—D2D3M3M4, D2D3D4M4 expressed in *E. coli*. MW, molecular mass.

FIG. 2A depicts Classical pathway decay-accelerating activity (CP-DAA) of DAF, MCP, D2D3 mutant and the indicated DAF-MCP chimeras. FIG. 2B depicts Alternative pathway decay-accelerating activity (AP-DAA) of DAF, MCP, D2D3 mutant and the indicated DAF-MCP chimeras. FIG. 2C depicts Binding analysis of DAF, MCP, D2D3 mutant and the indicated DAF-MCP chimeras to C3b (left panel) and C4b (right panel).

FIG. 3A depicts Relative C3b-CFA and C4b-CFA of MCP and D2D3M3M4. FIG. 3B depicts SDS-PAGE analysis of D2D3M3M4 and its single and multi-residue mutants expressed in *E. coli*. FIG. 3C depicts Relative C3b-CFA and C4b-CFA of D2D3M3M4 and its single and multi-residue mutants.

FIG. 4A depicts Substitution of the putative factor I interaction sites in D3 domain of D2D3M3M4 generate molecules (multi-4 & -5) with C3b-CFA. FIG. 4B depicts Substitution of the putative factor I interaction sites in D3 domain of D2D3M3M4 generate molecules (multi-4 & -5) with C4b-CFA. FIG. 4C depicts Alternative pathway decay-accelerating activity of the D3D3M3M4 substitution mutants (multi-4 & -5) in comparison to DAF and the DAF-MCP chimera D3D3M3M4. FIG. 4D depicts Classical pathway decay-accelerating activity of the D3D3M3M4 substitution mutants (multi-4 & -5) in comparison to DAF and the DAF-MCP chimera D3D3M3M4.

FIG. 5A depicts Model of the C3b-multi-4 mutant-FI trimolecular complex. FIG. 5B shows the zoomed view of the interactions shown by the gain-of-function residues with FI. FIG. 5C depicts Charge and hydrophobic interactions of gain-of-function residues with FI.

FIG. 6A shows the Relative binding of DAF, MCP and the indicated DAF-MCP chimeras to C3b (left panel) and C4b (right panel). FIG. 6B shows the Binding sensograms of D2D3M3M4, D2D3D4M4 and the multi-residue mutants of D2D3M3M4 (multi-4 & -5) to C3b (left panel) and C4b (right panel). FIG. 6C shows Relative binding of D2D3M3M4, D2D3D4M4 and the multi-residue mutants of D2D3M3M4 (multi-4 & -5) to C3b (left panel) and C4b (right panel).

FIG. 7 depicts interface analysis of the D2D3M3M4 chimera with C3b and Bb in the C3b-D2D3M3M4-Bb complex. FIG. 7 A depicts Interaction of DAF domains in D2D3M3M4 with C3b. FIG. 7B depicts the Interaction of DAF domains in D2D3M3M4 with VWA domain in Bb. DAFCCP2—Seq ID. No. 68; DAFCCP3—Seq ID. No. 69.

Sequence Set 1 (from the top of the page): DCP CCP2—Seq ID. No. 70; DAF CCP2—Seq ID. No. 71; MCP CCP1—Seq ID. No. 72; FH CCP1—Seq ID. No. 73; CR1 CCP15—Seq ID. No. 74; SPICE CCP1—Seq ID. No. 75; KAPO CCP1—Seq ID. No. 76; sCCPH CCP1—Seq ID. No. 77.

Sequence Set 2: DCP CCP2—Seq ID. No. 78; DAF CCP3—Seq ID. No. 79; MCP CCP2—Seq ID. No. 80; FH CCP2—Seq ID. No. 81; CR1 CCP16—Seq ID. No. 82; SPICE CCP2—Seq ID. No. 83; KAPO CCP2—Seq ID. No. 84; sCCPH CCP2—Seq ID. No. 85.

Sequence Set 3: DCP CCP3—Seq ID. No. 86; DAF CCP4—Seq ID. No. 87; MCP CCP3—Seq ID. No. 88; FH CCP3—Seq ID. No. 89; CR1 CCP17—Seq ID. No. 90; SPICE CCP3—Seq ID. No. 91; KAPO CCP3—Seq ID. No. 92; sCCPH CCP3—Seq ID. No. 93.

Sequence Set 4: DCP CCP4—Seq ID. No. 94; MCP CCP4—Seq ID. No. 95; FH CCP4—Seq ID. No. 96; SPICE CCP4—Seq ID. No. 97; KAPO CCP4—Seq ID. No. 99; sCCPH CCP4—Seq ID. No. 99.

Figure 10A:
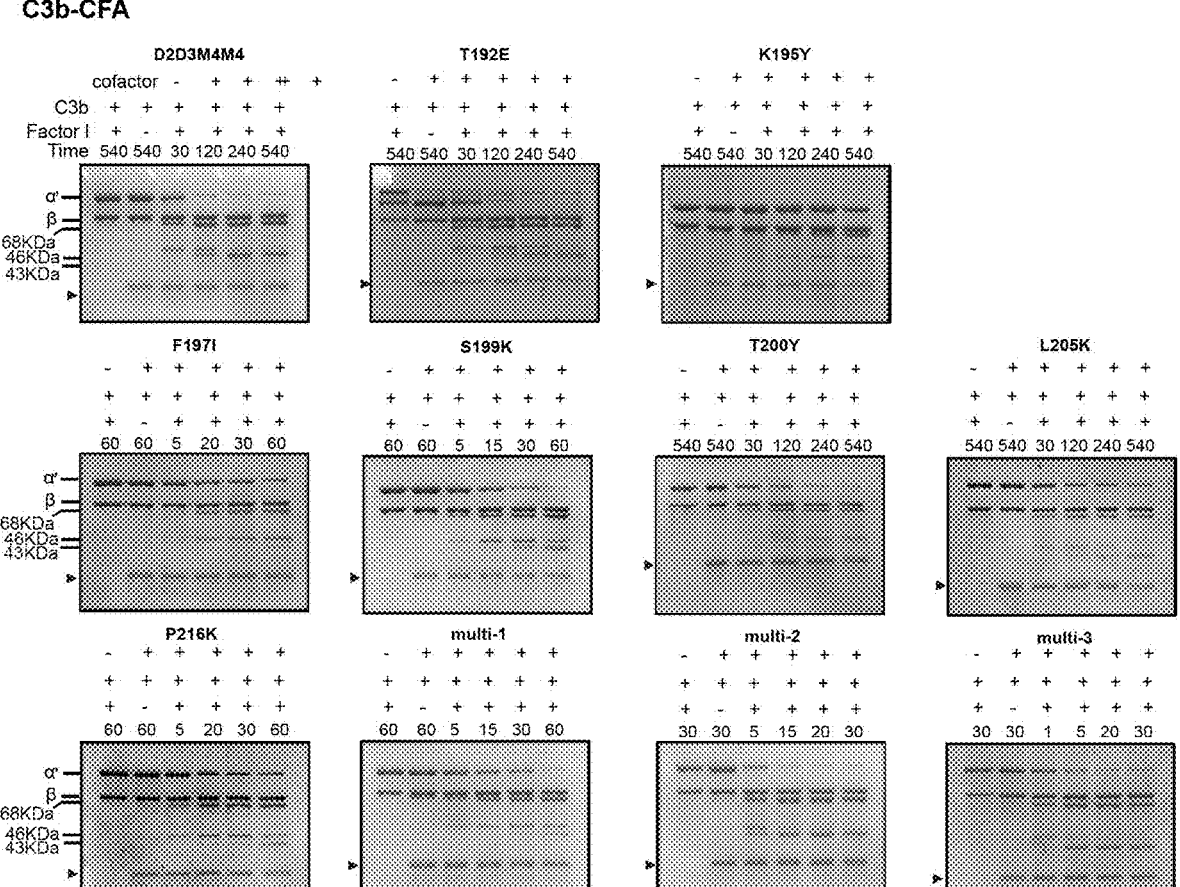
Figure 10B:
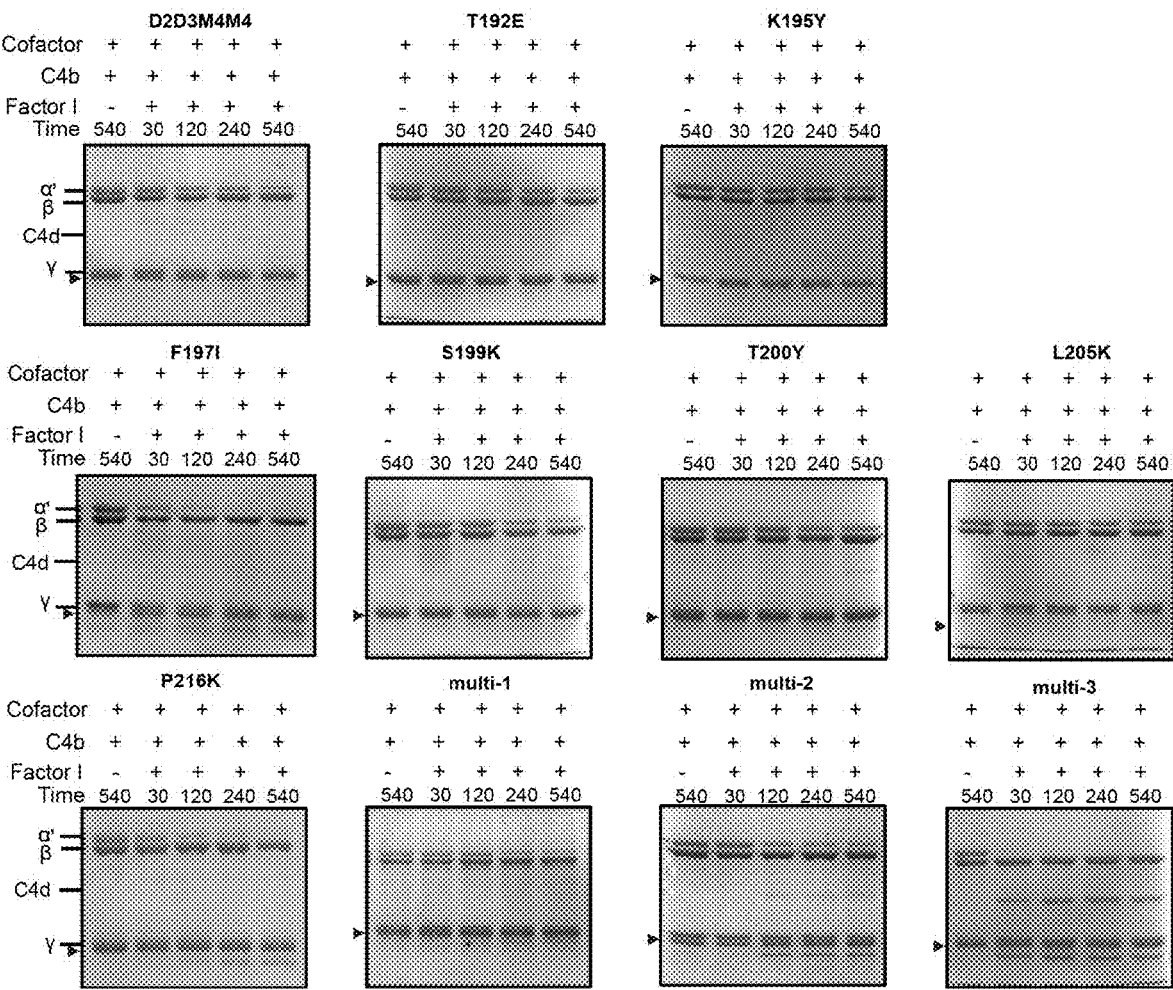

FIG. 10A shows the comparison of C3b cofactor activity (C3b-CFA) of the point and multi-residue mutants of D2D3M3M4 with D2D3M3M4. FIG. 10B shows the comparison of C4b cofactor activity (C4b-CFA) of the point and the multi-residue mutants of D2D3M3M4 with D2D3M3M4.

Figure 11:
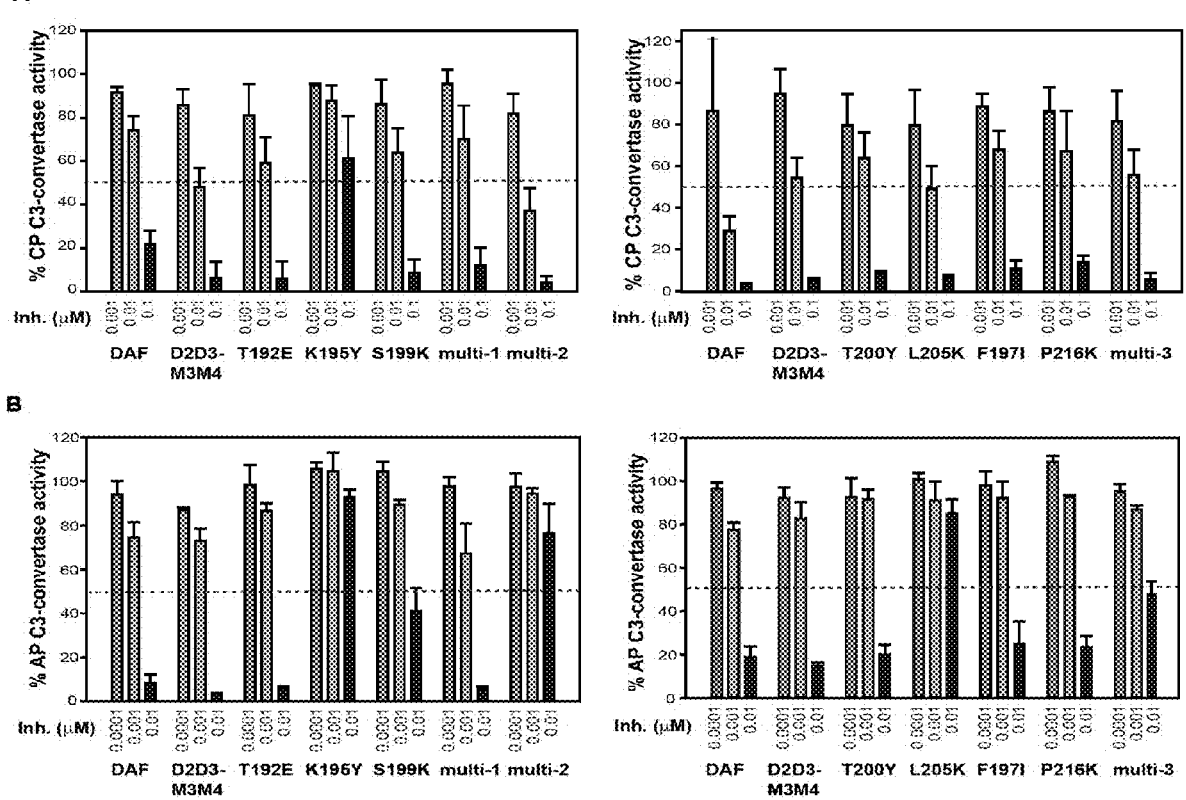

FIG. 11 depicts CP-DAA and AP-DAA measurements of DAF, D2D3M3M4, and the single and multi-residue mutants of D2D3M3M4.

Figure 12:
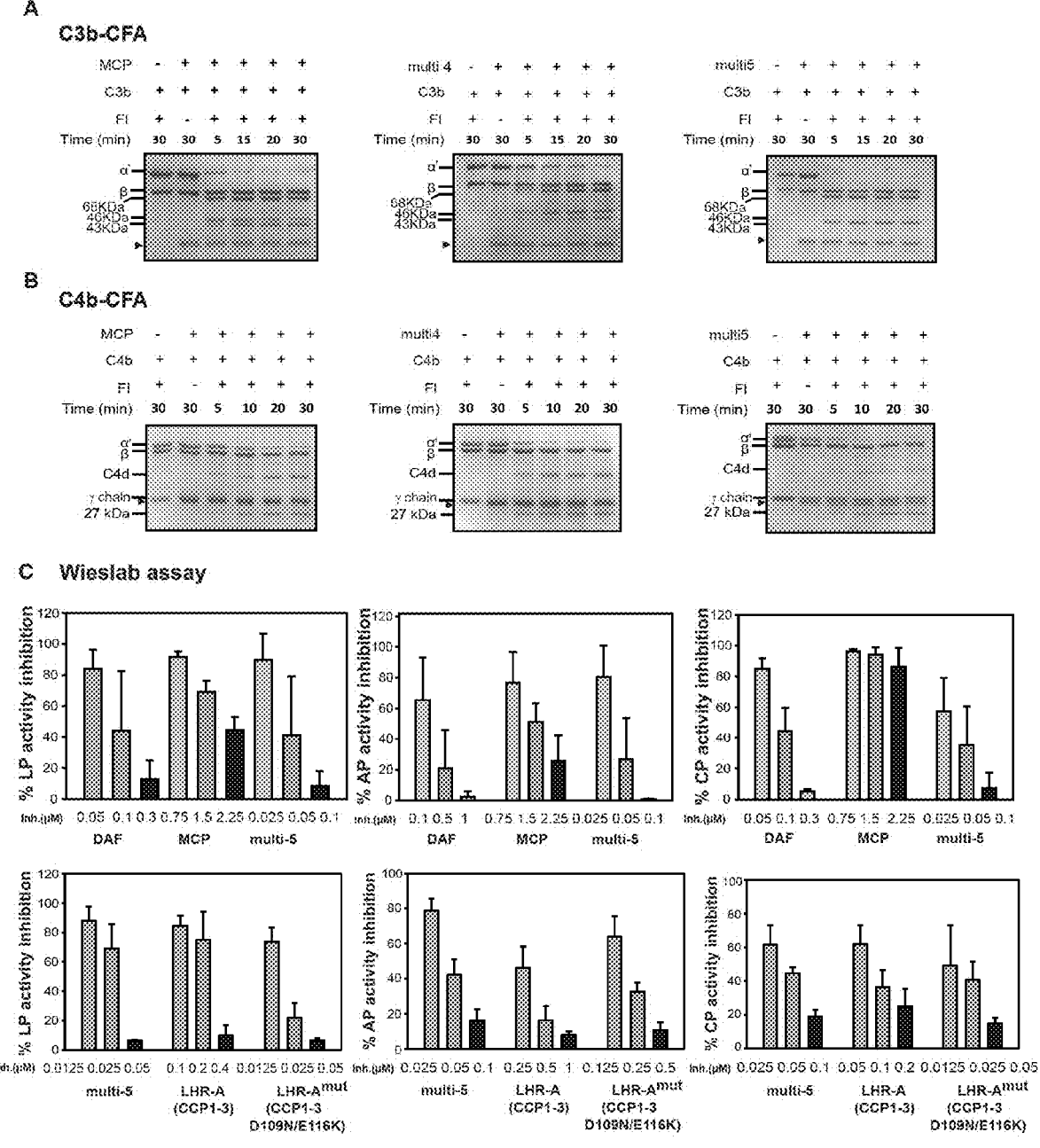

FIG. 12 depicts the comparison of cofactor activity of the multi-residue mutants of D2D3M3M4 with MCP, and their effect on classical, alternative and lectin pathways. FIG. 12A shows C3b-CFA. FIG. 12B C4b-CFA. FIG. 12C shows relative effect of DAF, MCP, CR1 LHR-A (CCP1-3), CR1 LHR-A$^{mut}$ (CCP1-3 D109N/E116K) and the multi-residue mutants of D2D3M3M4 on the classical, alternative and lectin pathways.

Figure 13A:
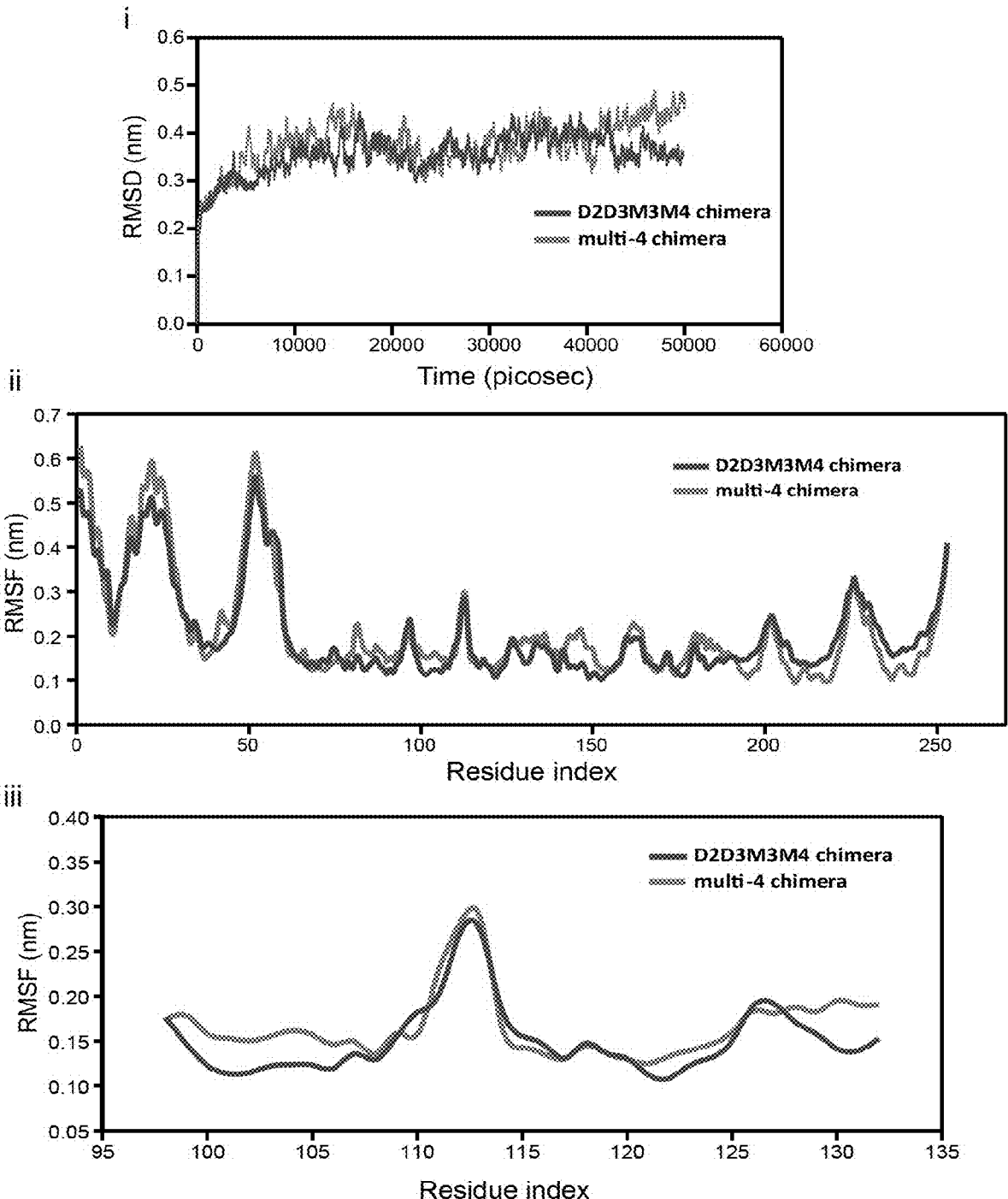
Figure 13B:
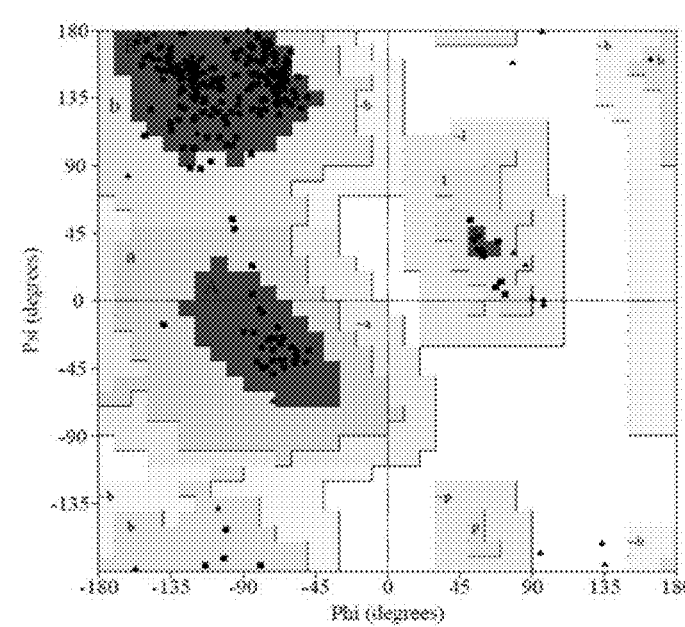

FIG. 13 depicts RMSD and RMSF plots of C3b-multi4-FI complex (13A) and further illustrates the Validation of the D2D3M3M4 chimera model (13B). FIG. 13A: (i) Backbone RMSD of C3b-multi4-FI complex for 50 ns simulation. (ii) Root mean square fluctuation (RMSF) of chimera residues for the entire simulation time. (iii) Plot showing the RMSF of the multi-4 mutant residues located in the region where gain-of-function mutations have been identified. FIG. 13B illustrates the validation of the D2D3M3M4 chimera model using Ramachandran plots for D2D3M3M4 chimera and multi-4 mutant.

Figure 14:
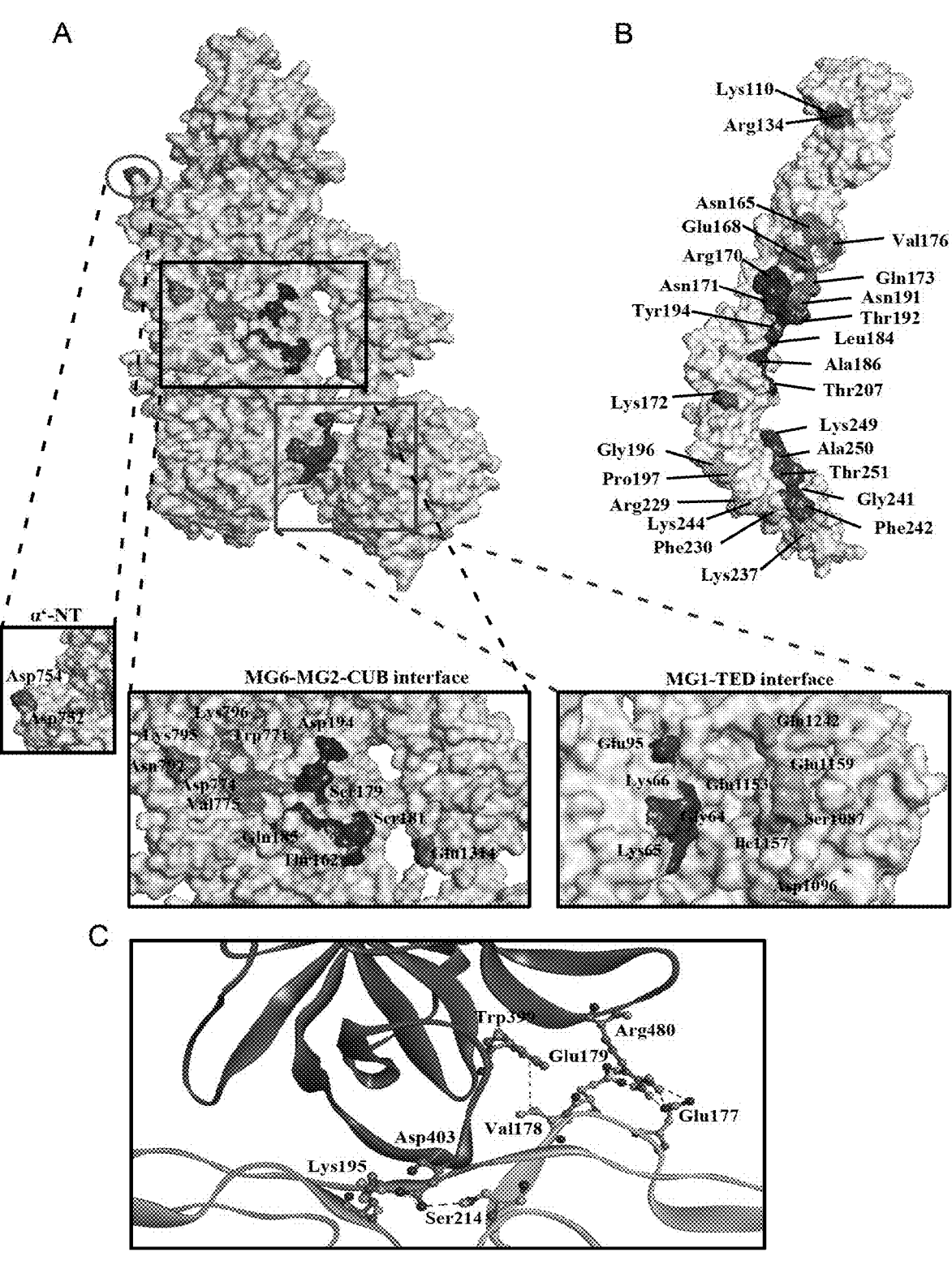

FIG. 14 depicts the mapping of interaction of multi-4 mutant with C3b and FI in C3b-multi-4 mutant-FI complex. FIG. 14A depicts DAF (D2-D3) as well as MCP domains (M3-M4) of multi-4 mutant show interaction with C3b. FIG. 14B depicts C3b interacting residues of multi-4 mutant. FIG. 14C depicts the Interactions of the M3 domain residues with FI. Glu177 and Glu179 show strong charge interactions with Arg480 of FI.

Figure 15A:
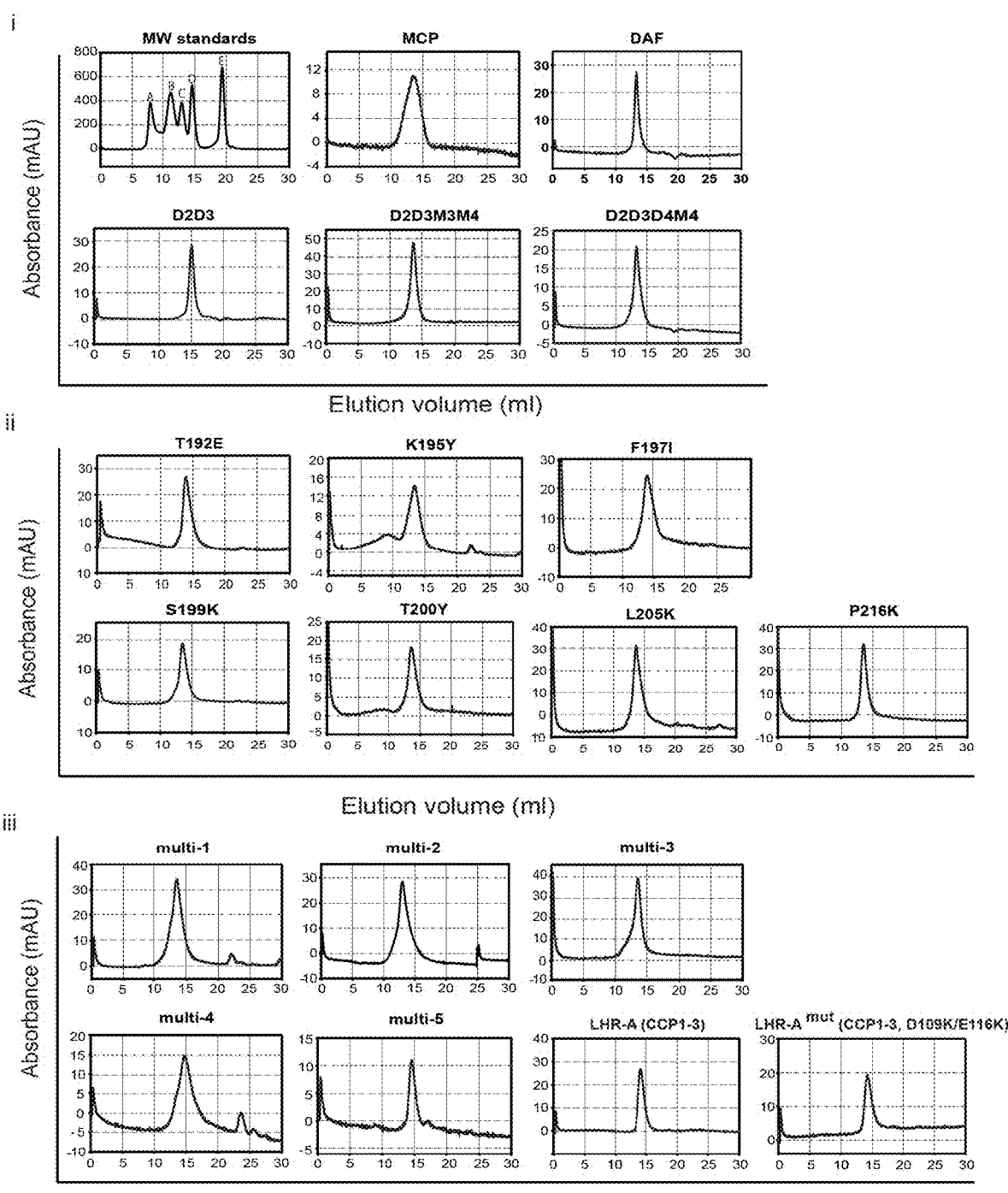
Figure 15B:
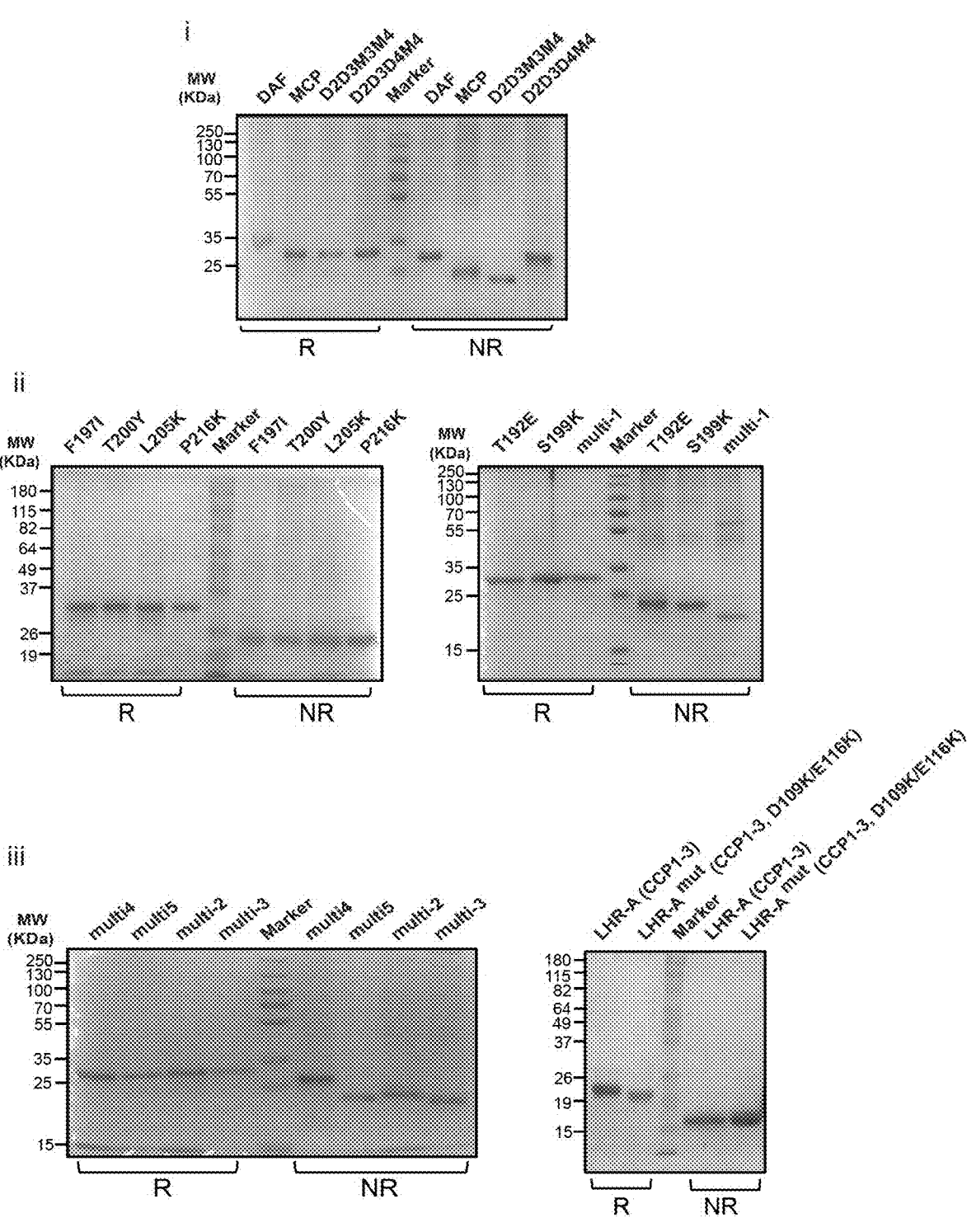

FIG. 15A depicts size exclusion chromatography analysis of DAF, MCP, D2D3, the DAF-MCP chimeras D2D3M3M4 and D2D3D4M4, the single and multiresidue mutants of D2D3M3M4. FIG. 15B shows SDS-PAGE analysis of purified DAF, MCP, the DAF-MCP chimeras D2D3M3M4 and D2D3D4M4, and the single and multi-residue mutants of D2D3M3M4.

FIG. 16 shows putative gain-of-function mutants of D2M2-4 chimera. (A) Sequence of D2M2-4 showing all the CCP domains and the linkers (underlined). Invariant cysteine residues are highlighted in yellow. Residues that were mutated for gain in AP-DAA are marked by arrows (residues in red and marked by blue arrows). D2—Seq ID. No. 64; M2—Seq ID. No. 65; M3—Seq ID. No. 66; M4—Seq ID. No. 67. (B) SDS-PAGE analysis of the single amino acid substitution mutants of D2M2-4. (C) The table shows the list of all the mutations and their location. These mutations were based on the earlier mutagenesis data on human (DAF, CR1) as well as viral regulators (SPICE, sCCPH, and Kaposica).

Figure 17:
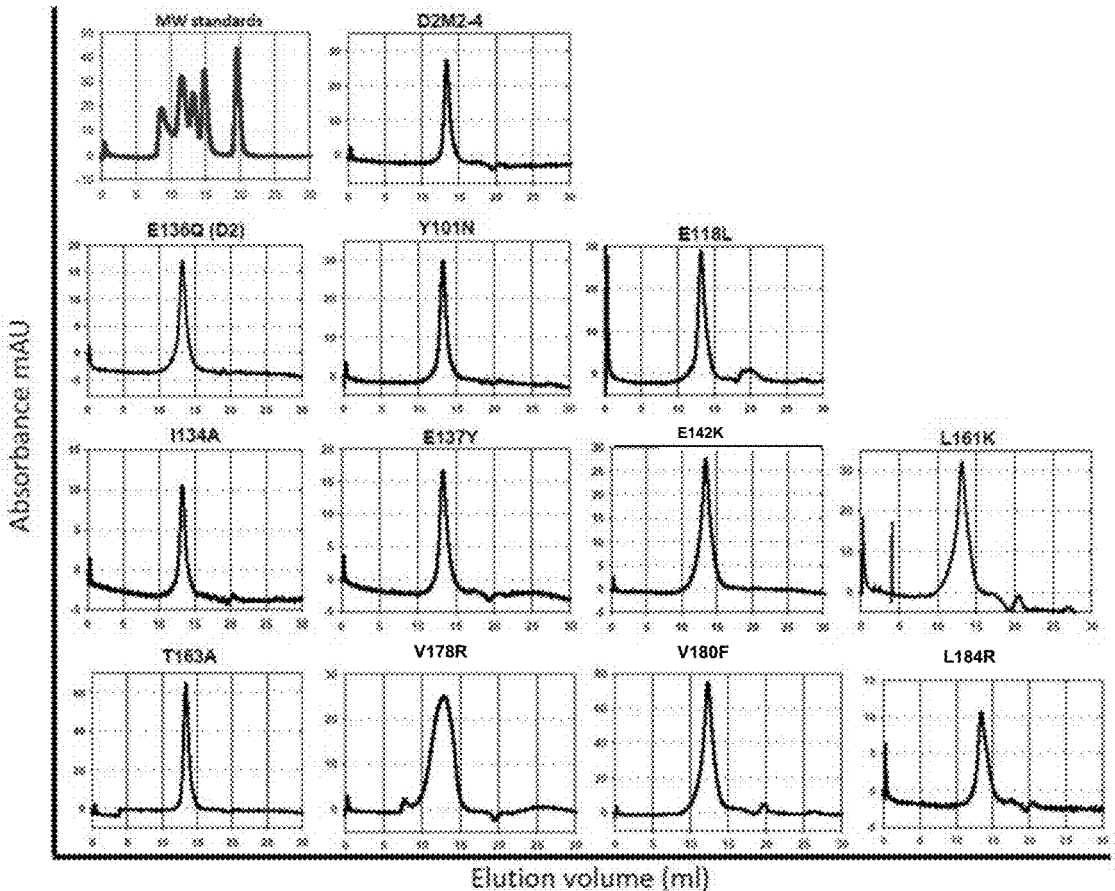

FIG. 17 depicts size exclusion chromatography analysis of D2M2-4 and putative gain-of-function mutants of D2M2-4. The D2M2-4 chimera and the single amino acid substitution mutants of D2M2-4 were loaded onto SUPEROSE-12™ column (GE Healthcare Life Sciences) pre-equilibrated with PBS (pH 7.4). The gel filtration standards (Bio-Rad) used were: A, Thyroglobulin (670,000 Da); B, Gamma globulin (158,000 Da); C, Ovalbumin (44,000 Da); D, Myoglobin (17,000 Da); E, Vitamin B-12 (1,350 Da).

Figure 18:
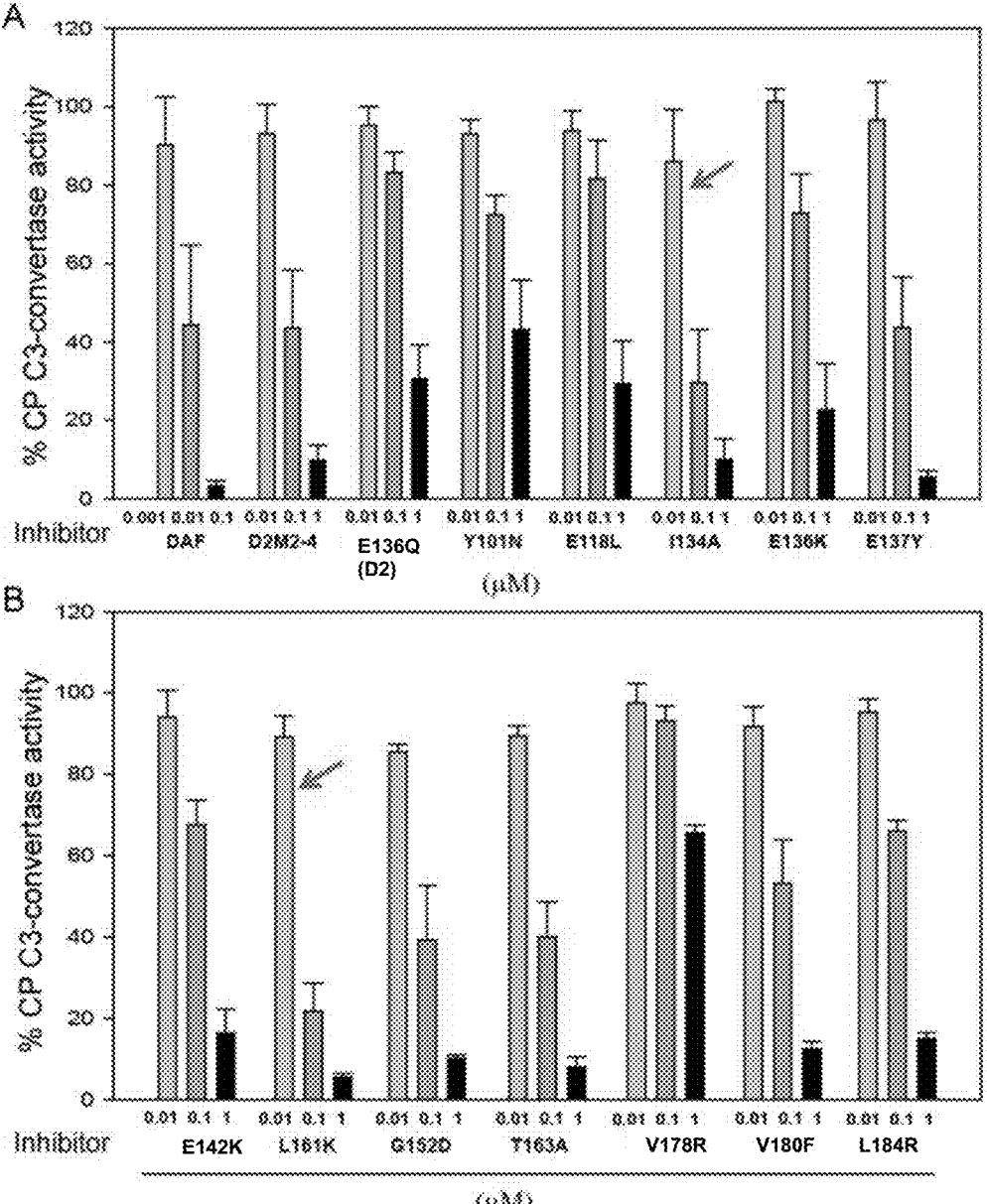

FIG. 18 depicts the CP-DAA measurements of DAF, D2M2-4, and its putative gain-of-function mutants. CP-DAA of the respective protein was measured by evaluating their ability to decay the pre-formed CP C3-convertase (C4b2a). The data were normalized by considering the 100% C3-convertase activity to be equal to the activity without the inhibitor. Arrows indicate the mutants with gain in CP-DAA. Data shown are mean±SD of three independent experiments.

Figure 19:
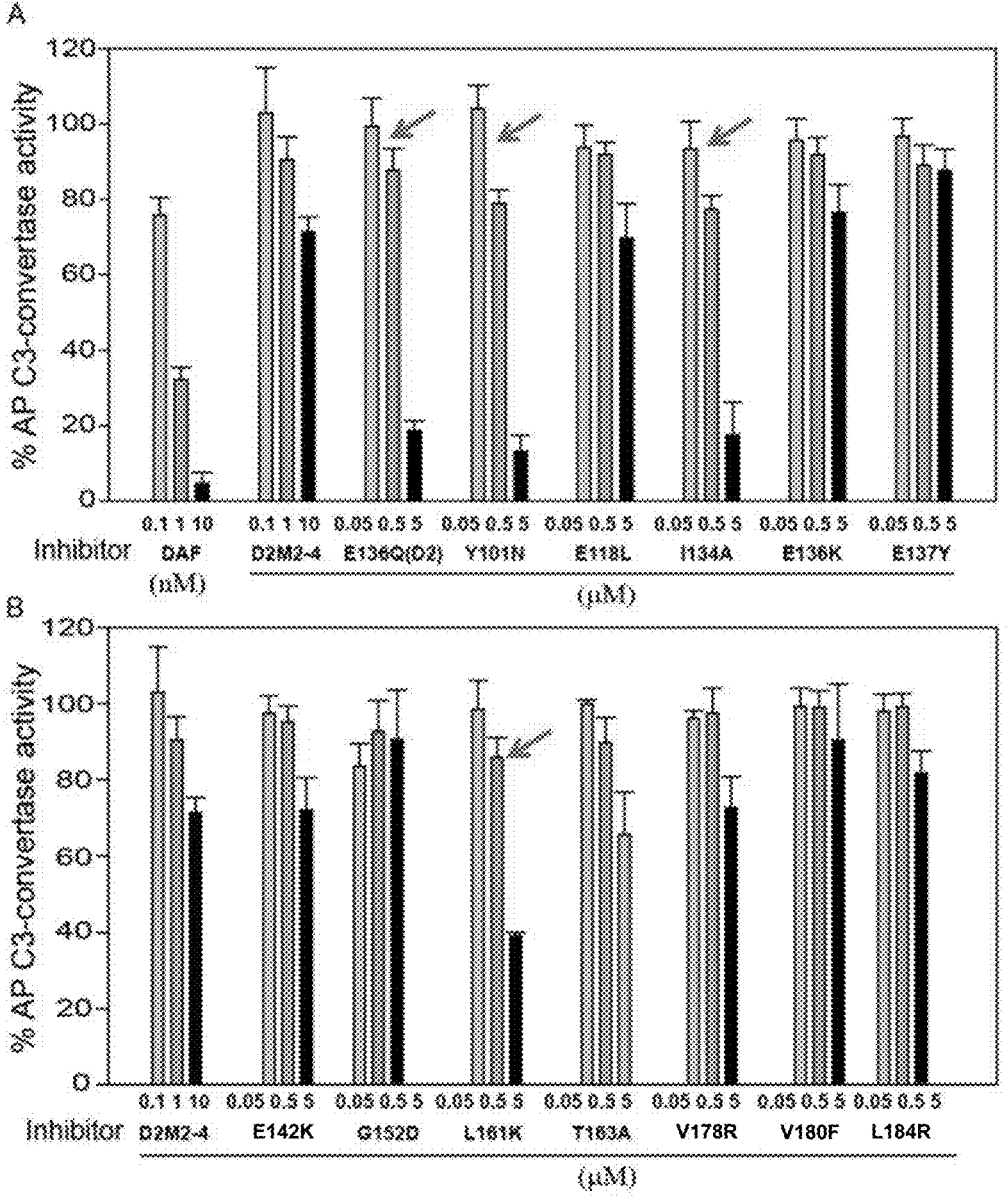

FIG. 19 depicts the AP-DAA measurements of DAF, D2M2-4, and its putative gain-of-function mutants. AP-DAA of the respective proteins was measured by evaluating their ability to decay the pre-formed AP C3-convertase (C3bBb). The data were normalized by considering the 100% C3-convertase activity to be equal to the activity without the inhibitor. Arrows indicate the mutants with gain in AP-DAA. Data shown are mean±SD of three independent experiments.

FIG. 20 depicts the binding of DAF, D2M2-4 and its putative gain-of-function mutants to C3b and C4b. Sensogram overlay plots showing the interaction of DAF, D2M2-4 and its mutants with C3b (A) and C4b (B). Briefly, all the proteins were flown at 1 μM concentration over the immobilized biotin labelled C3b/C4b. Residues which affects the CP-DAA and AP-DAA are highlighted in red fonts.

Figure 21:
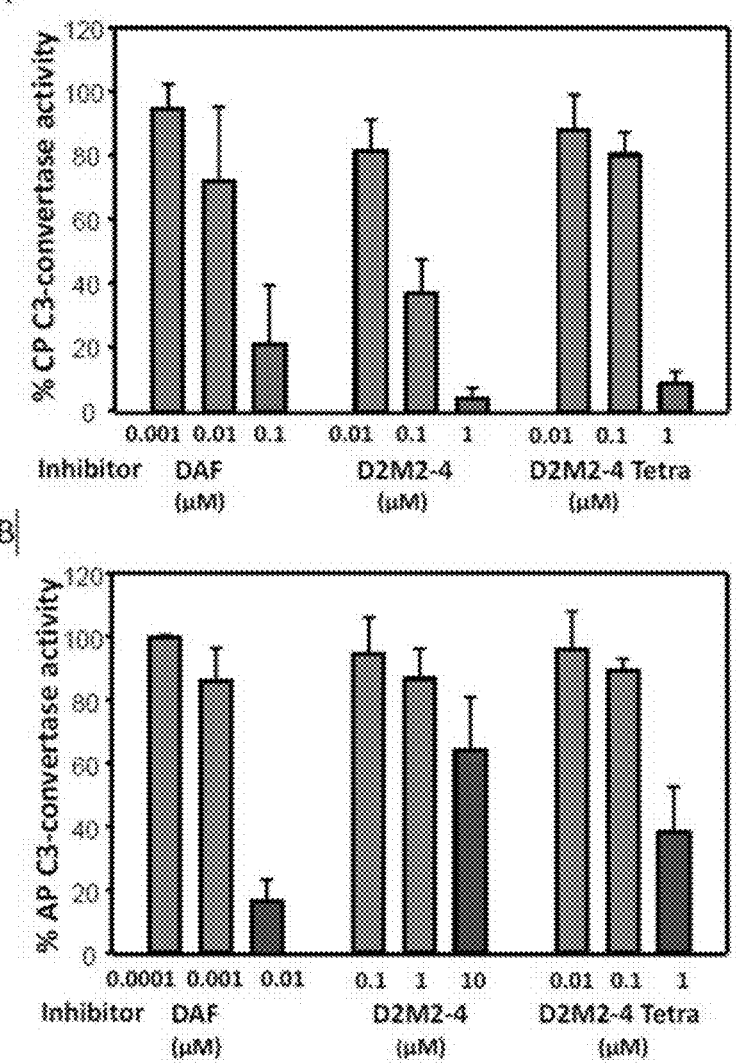

FIG. 21 depicts the CP-DAA and AP-DAA measurements of DAF, D2M2-4 and the tetra mutant of D2M2-4. (A) CP-DAA of the respective proteins was measured by evaluating their ability to decay the pre-formed CP C3-convertase (C4b2a). (B) AP-DAA of the respective proteins was measured by evaluating their ability to decay the pre-formed AP C3-convertase (C3bBb). The data was normalized by considering the 100% C3-convertase activity to be equal to the activity without the inhibitor. Data shown are mean f SD of three independent experiments.

FIG. 22 depicts the cofactor activity measurements of D2M2-4 and the tetra mutant of D2M2-4. The cofactor activity of these proteins was measured by incubating them with C3b (A) or C4b (B) and factor I at 37° C. for the indicated time in PBS. The cleavage products of C3b/C4b were observed by running them on SDS-PAGE (9% for C3b and 10% for C4b) under reducing conditions. In C3b-CFA, the α'-chain is cleaved into N-terminal 68-kDa and C-terminal 46-kDa fragments amongst which the 46-kDa fragment is further cleaved into 43-kDa fragment. In C4b-CFA, the α'-chain is cleaved into N-terminal 27-kDa, central C4d and C-terminal 16-kDa fragments; the C-terminal fragment is not visualized on the gel.

|

DETAILED DESCRIPTION OF THE INVENTION

The present application contains a Sequence Listing which has been submitted in PATENTIN and is hereby incorporated by reference in its entirety. Said PATENTIN-3.5 version, created in the name of Sequence listing.txt and is 20 kilobytes in size.

The present invention provides the protein sequence Ids of DAF (Seq. ID. No. 1), and MCP (Seq ID. No.2). The present invention also provides the protein Sequence Id No.3 pertaining to D2D3, which demonstrated inhibition of CP-DAA. It was observed that D2D3 does not provide adequate effect in AP-DAA. This protein has been used as a control in the example(s) as appropriate and disclosed herein, The present invention also provides for chimeric proteins D2M2-4 (Seq. ID. No. 4); D2M2-4 (ML) (Seq. ID. No. 5); D2D3M3M4 (Seq. ID. No. 6); D2D3D4M4 (Seq. ID. No. 7); D2D3M3M4 (T192E) (Seq. ID. No. 8); D2D3M3M4 (K195Y) (Seq. ID. No. 9); D2D3M3M4 (F197I) (Seq. ID. No. 10); D2D3M3M4 (S199K)) (Seq. ID. No. 11); D2D3M3M4 (T200Y)) (Seq. ID. No. 12); (D2D3M3M4 (L205K)) (Seq. ID. No. 13); D2D3M3M4 (P216K) (Seq. ID. No. 14); D2D3M3M4 (Multi-1) (Seq. ID. No. 15); D2D3M3M4 (Multi-2) (Seq. ID. No. 16); D2D3M3M4 (Multi-3) (Seq. ID. No. 17); D2D3M3M4 (Multi-4) (Seq. ID. No. 18); D2D3M3M4 (Multi-5) or DCP (Seq. ID. No. 19); D2M2-4 (E136Q) (D2) (Seq. ID. No. 20); (D2M2-4 (Y101N) (Seq. ID. No. 21); (D2M2-4 (E118L) (Seq. ID. No. 22); D2M2-4 (I134A) (Seq. ID. No. 23); D2M2-4 (E136K) (Seq. ID. No. 24); (D2M2-4 (E137Y)) (Seq. ID. No. 25); (D2M2-4 (E142K) (Seq. ID. No. 26); D2M2-4 (G152D) (Seq. ID. No. 27); D2M2-4 (L161K) (Seq. ID. No. 28); D2M2-4 (T163A) (Seq. ID. No. 29); D2M2-4 (V178R) (Seq. ID. No. 30); (D2M2-4 (V180F) (Seq. ID. No. 31); D2M2-4 (L184R) (Seq. ID. No. 32); D2M2-4 (Tetra) (Seq. ID. No. 33).

The engineered chimeric proteins of the present invention comprise domains selected from D1, D2, D3 and D4 domains of Decay-Accelerating Factor (DAF) and domains selected from M1, M2, M3 and M4 of membrane cofactor protein (MCP), optionally along with linkers.

The present invention discloses a chimeric protein D2D3M3M4 (Multi-5) or DCP (Seq. ID. No. 19).

The engineered chimeric protein D2D3M3M4 (Multi-5) or DCP (Seq. ID. No. 19) having D2 and D3 domains of Decay-Accelerating Factor (DAF) and M3, and M4 of membrane cofactor protein (MCP), along with linkers and specific mutations.

Figure 1:
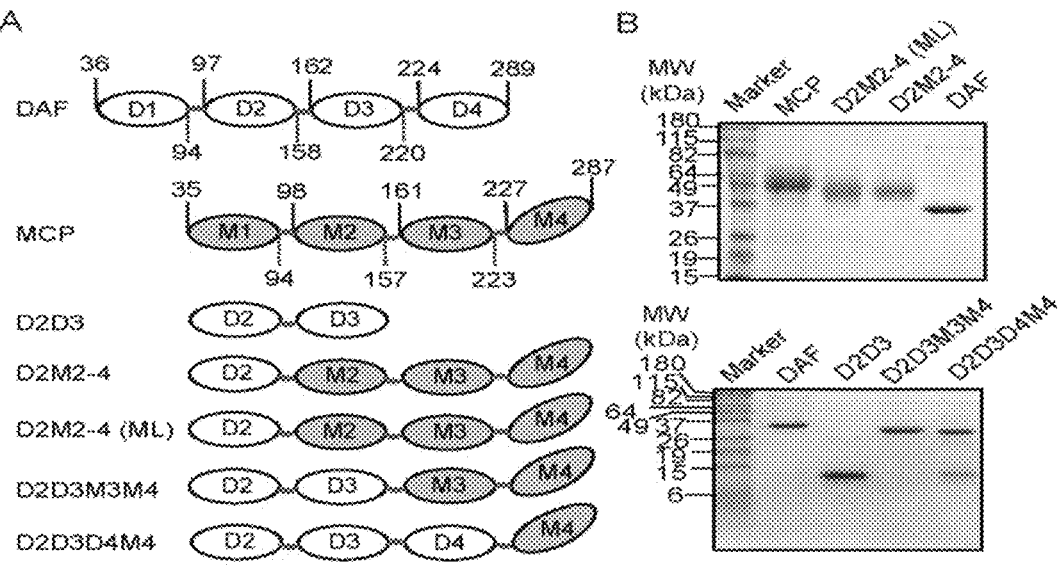
FIG. 1 depicts the construction of various DAF-MCP chimeras.

The present invention discloses novel modified four domain DAF-MCP chimeric proteins with dual-activity regulation and further modified for enhancing interaction with factor I and C3b/C4b and the sequence ID 19 (DCP). The diagrammatic representations of DAF, MCP and the DAF-MCP chimeras and SDS-PAGE analysis are at FIGS. 1(A) and (B).

The present invention discloses the engineered four domain protein having domains D2, D3 and/or D4 from human DAF protein and M2, M3, and/or M4 domains from human MCP protein resulting in proteins/mutants/chimeras D2M2-4, D2M2-4 with MCP linker, D2D3M3M4, D2D3D4M4; the engineered protein D2D3M3M4 further modified with gain-of function mutations in the domains with single amino acid substitutions, multiple amino acid substitutions and combinations of single and multiple amino acid residues; and the D2D3M3M4 modified with two mutations in domain D3 (F197I and P216K) and one multi-residue mutation (multi-1, i.e., linker substitution mutations—219ECREIY224 (Seq. ID. No. 100) to ICEKVL (Seq. ID. No. 101)) was collectively substituted to create Multi-5 (DCP). In DCP both two N-terminal modules of DAF were substituted.

To obtain DCP further mutations were carried out for increasing the interaction with Factor I in the D2D3M3M4 being selected from T192E, K195Y, F197I, S199K, T200Y, L205K and P216K and 3 multi-residue Multi-1, Multi-2 and Multi-3.

In an embodiment, the present invention discloses a process that to engineer an obtain the four domain DAF-MCP chimeric protein (DCP) having dual-activity regulation and enhanced interaction with factor I and C3b/C4b resulting in mutant Multi-5 (DCP) using recombinant techniques and introduction of mutations comprising the steps of:

i. domains of the RCA proteins DAF and MCP and their respective linkers were swapped to study and identify functional aspects and to obtain chimeric proteins;

ii. D2D3M3M4 chimera was selected and further modifications and mutations were introduced to create mutants with increased CFA;

iii. creation of D2D3M3M4 mutants having both increased DAA and CFA;

iv. resultant chimeric mutants D2M2-4, D2D3M3M4 and D2D3D4M4, and the single and multi-residue mutants of D2D3M3M4, and D2M2-4.

v. expression of mutants of step (iv) in bacterial and/or yeast expression vectors.

The process of the present invention resulted in then engineered chimeric protein for inhibition of complement pathways selected from the group comprising D2M2-4 (Seq. ID. No. 4); D2M2-4 (ML) (Seq. ID. No. 5); D2D3M3M4 (Seq. ID. No. 6); D2D3D4M4 (Seq. ID. No. 7); D2D3M3M4 (T192E) (Seq. ID. No. 8); D2D3M3M4 (K195Y) (Seq. ID. No. 9); D2D3M3M4 (F197I) (Seq. ID. No. 10); D2D3M3M4 (S199K)) (Seq. ID. No. 11); D2D3M3M4 (T200Y)) (Seq. ID. No. 12); (D2D3M3M4 (L205K)) (Seq. ID. No. 13); D2D3M3M4 (P216K) (Seq. ID. No. 14); D2D3M3M4 (Multi-1) (Seq. ID. No. 15); D2D3M3M4 (Multi-2) (Seq. ID. No. 16); D2D3M3M4 (Multi-3) (Seq. ID. No. 17); D2D3M3M4 (Multi-4) (Seq. ID. No. 18); D2D3M3M4 (Multi-5) or DCP (Seq. ID. No. 19); D2M2-4 (E136Q) (D2) (Seq. ID. No. 20); (D2M2-4 (Y101N) (Seq. ID. No. 21); (D2M2-4 (E118L) (Seq. ID. No. 22); D2M2-4 (I134A) (Seq. ID. No. 23); D2M2-4 (E136K) (Seq. ID. No. 24); (D2M2-4 (E137Y)) (Seq. ID. No. 25); (D2M2-4 (E142K) (Seq. ID. No. 26); D2M2-4 (G152D) (Seq. ID. No. 27); D2M2-4 (L161K) (Seq. ID. No. 28); D2M2-4 (T163A) (Seq. ID. No. 29); D2M2-4 (V178R) (Seq. ID. No. 30); (D2M2-4 (V180F) (Seq. ID. No. 31); D2M2-4 (L184R) (Seq. ID. No. 32); D2M2-4 (Tetra) (Seq. ID. No. 33).

The process of the present invention provided the protein D2D3M3M4 (Multi-5) or DCP (Seq. ID. No. 19).

Without being limited by theory, it is submitted that process of the present invention introduces modifications and mutations to increase CFA, AP-DAA and CP-DAA activities.

i. The Process to the Manufacture the Modified Four Domain DAF-MCP Chimeric Protein (DCP) of the Present Invention is Disclosed Here: The Domains of the RCA Proteins DAF and MCP and their Respective Linkers were Swapped to Study and Identify Functional Aspects—

The domains and respective linkers of the DAF and MCP were swapped using the domain swap technology to identify the essential domains and the linkers for the best DAA (CP-DAA and AP-DAA) and CFA (C3b-CFA and C4b-CFA) activity. It was found that CCP2-3 of DAF induce both CP-DAA and AP-DAA, while CCP4 aid by serving as a C3b binding domain; and CCP2-3 are required for DAA in DAF and one or more of MCP's domains (M1-M3) and the linkers with the homologous domains of DAF (D2-D4) and the associated linkers were swapped as MCP lacks DAA, the resulting proteins/mutants were tested for gain-of-function; the significance of the linker between D2-D3 (i.e., KKKS; net positive charge+3) in DAA was tested before swapping the next domain. Proteins/mutants were created where the D2D3 protein have the D2D3 domains along with the D2D3 linker. The D2M2-4_protein was created having D2 domain with D2-D3 linker, M2M3M4 domains with their respective M2M3M4 linkers this substitution alone was enough to impart CP-DAA, though the protein/mutant was 30-fold less active compared to DAF. This protein, however, displayed diminished AP-DAA highlighting the crucial role of other modules in the activity. The D2M2-4 (ML) protein/mutant was created where the D2-D3 linker in D2M2-4 was replaced with the neutral linker (YRET) of MCP; Therefore, resultant mutant/protein (D2M2-4-ML), unlike that of D2M2-4, showed no gain in CP-DAA. The D2M2-4 protein with MCP linker (D2M2-4-ML) also showed a considerable loss in binding to C3b and C4b compared to D2M2-4 protein with DAF linker (D2M2-4). The D2D3M3M4 mutant/protein where the two N-terminal modules of DAF along with the associated linkers in MCP (D2D3M3M4) was substituted and the DAA of this protein was assessed and it was observed that the protein demonstrated CP-DAA as well as AP-DAA equal to that of DAF and substitution of three domains of DAF along with the linkers in MCP (D2D3D4M4) did not result in any further increase in DAA. Further the data suggested that the slower off-rate affects the regulator's recycle rate for AP C3 convertase complexes, which results in its reduced AP-DAA, these indicated that decay is induced only by CCP2-3 of DAF; it was determined that the D4 module in DAF merely plays a role of C3b binding domain, and its function can be substituted by M3-M4; the possible interactions of D2D3 modules in the D2D3M3M4 chimera with the AP C3 convertase subunits (i.e., C3b and Bb) were studied and C3b-D2D3M3M4-Bb complex was modelled, further, interface analysis showed that D2 and D3 interact with both C3b as well as Bb and that D2 and the D2-D3 linker formed contacts with α7-helix of Von Willebrand factor type-A (VWA) domain in Bb, while D3 formed contacts with α7-helix, and α6-βF and α5-βE loops of VWA domain in Bb, the present modelling data show that D2 and D3 majorly interact with α6-βF and α5-βE loops in addition to the α7-helix and therefore, interaction of D2-D3 with these loops is important for allosteric changes in the MIDAS site leading to decay of Bb from C3b; the Factor I interaction sites on M2 as well as M3 required for optimum CFA of MCP was determined and it was found that FI interaction site present on M3 alone can contribute functionally to CFA; the DAA of these D2D3M3M4 mutants were evaluated particularly in the chimeras that showed a gain in CFA, it was determined that coexistence of strong CFA and DAA in a structural framework of four CCPs is achievable, the residues that provide gain of CFA were determined by sequence alignment of various RCA proteins; a four CCP DAF-MCP protein displaying DAA and CFA as robust as the parent molecules was engineered. The D2D3D4M4 protein/mutant was created having respective linkers of domains D2D3D4 and linker of M4 between domains D4 and M4. The created proteins were tested and studied for their DAA and CFA and further mutations were introduced, tested and studied to increase the regulatory activity of the mutant/chimera proteins.

ii. The D2D3M3M4 Chimera was Selected and Further Modifications and Mutations were Introduced to Study and Create Mutants with Increased CFA—

The CFA of this D2D3M3M4 protein/mutant was increased by substituting the FI interaction site in the D3 domain (homologous to M2) and the D3-M3 liker without affecting its DAA. The substitution of putative FI interacting residues in D3 and the attached linker (D3-M3 linker) of D2D3M3M4 protein was performed based on the earlier mutagenesis studies on the viral and human RCA proteins. A total of 7 single (T192E, K195Y, F197I, S199K, T200Y, L205K and P216K) and 3 multi-residue (Multi-1, Multi-2 and Multi-3) mutants of D2D3M3M4 were generated. These mutations reside between Cys2-Cys4 region of D3 and the D3-M3 linker (ECREIY; Seq. ID. No. 100) as the earlier swapping of this region of DAF with the homologous region of MCP resulted in the incorporation of CFA in DAF. Biochemical analysis of the single and multi-residue mutants showed varying results—a complete loss to 28-fold gain in CFA. Substitutions that showed a >2-fold gain in C3b CFA included single amino acid mutants like S199K, and P216K, and multi-residue mutant like multi-1 (linker substitution mutant—219ECREIY224 (Seq. ID. No. 100) to ICEKVL (Seq. ID. No. 101)), multi-2 (linker substitution+ S199K) and multi-3 (215DPL217 to PKA). Likewise, mutations that showed >2-fold gain in C4b CFA included F197I, S199K, P216K, multi-2 and multi-3. The mutants (three single-residue mutants (F197I, S199K, P216K) and one multi-residue mutant (multi-1, i.e., linker substitution mutant) with increased CFA were selected.

iii. The D2D3M3M4 Mutants/Proteins with Increased CFA were Further Studied and Modified to Create Mutants/Proteins with Intact DAA—

The DAA of these D2D3M3M4 mutants were studied for the loss in DAA, particularly in the mutants that showed a gain in CFA. Some mutants that exhibited a gain in CFA showed a loss in DAA. However, three mutants (F197I, P216K and multi-1) showed little or no loss in AP-DAA and none of the gain in CFA mutants showed >2-fold loss in CP-DAA. Therefore, this data supported the premise that coexistence of strong CFA and DAA in a structural framework of four CCPs is achievable. The sequence alignment of various RCA proteins was performed to examine whether residues that provided gain in CFA are conserved in other RCA proteins that show CFA. It was observed that 5 of 10 residues that are associated with a gain in activity are conserved in position in other proteins with CFA.

iv. The D2D3M3M4 Mutants Having Both Increased DAA and CFA were Created—

Mutant Multi-4 was created when D2D3M3M4 mutant was substituted with three single-residue mutations (F197I, S199K, P216K) in the D3 domain and one multi-residue mutation (multi-1, i.e., linker substitution mutant) in the D3M3 linker. Multi-5 was created when the D2D3M3M4 mutant was substituted with two single-residue mutations (F197I and P216K) in the D3 domain and one multi-residue mutation (multi-1, i.e., linker substitution mutant) in the D3M3 linker. The multi-4 and multi-5 mutants were studied and the successful design of a four CCP molecule with efficient CFA and DAA (DCP) was created which is more potent than LHR-A (CCP1-3) in inhibiting the lectin and alternative pathways and more potent than LHR-A$^{mut}$ in inhibiting the alternative pathway. It is similar to LHR-A$^{mut}$ in inhibiting the classical and lectin pathways. The molecular dynamics simulations of the C3b-multi-4 mutant-FI complex were studied and experimentation revealed information on interactions of mutated residues in the chimera with FI and overall, the interaction patterns of the linker and associated regions of the chimera/protein with FI are congruent with experimental study and data, and the domain-specific interactions were found to be similar to DAF and MCP.

v. The Chimeric Proteins were Expressed in Bacterial and Yeast Expression Vectors and Studied—

Human DAF, MCP, DAF-MCP chimeras/protein and substitution mutants of D2D3M3M4 and CR1 LHR-A (CCP1-3) and its mutant were constructed by amplifying from their respective cDNAs and cloned into either the yeast expression vector pPICZα and/or the bacterial expression vector pET-28b. The DAF-MCP proteins were constructed using the gene splicing and overlap extension method and then cloned either into the yeast expression vector pPICZα or into the bacterial expression vector pET-28b. The CR1 LHR-A (CCP1-3) was amplified from CR1 cDNA and cloned in the pET-28b for its expression. The primer sets were used to amplify the required regions of DAF, MCP and CR1; the substitution mutants of D2D3M3M4 and CR1 LHR-A (CCP1-3) were constructed using the QUICK-CHANGE™ site-directed mutagenesis kit II and cloned into the bacterial expression vector pET-28b, the DAF deletion mutant D2-D3 was amplified from DAF cDNA and cloned into pET-28b; following cloning, all the constructs were validated by DNA sequencing and the cloned mutants were expressed in *Pichia pastoris* and mutants cloned into pET-28b were transformed into *Escherichia coli* BL21 cells.

Expression and purification of Human DAF, MCP, DAF-MCP protein/mutants namely D2M2-4 (chimera/protein containing the DAF linker between D2-D3) and D2M2-4-ML (chimera/protein containing the linker between M1-M2). These were expressed in *P. pastoris*, purified, dialyzed and concentrated; Similarly, Human DAF and MCP were also expressed in *E. coli* along with other mutants including the DAF mutant D2D3, DAF-MCP mutants/proteins D2D3M3M4 and D2D3D4M4, and substitution mutants of D2D3M3M4, the CR1 LHR-A (CCP1-3) and its mutant CR1 LHR-A$^{mut}$ (CCP1-3, D109N/E116K). They were purified and refolded.

The classical/lectin and alternative pathway C3-convertase decay-accelerating activity of DAF, DAF-MCP chimeras and the mutants of D2D3M3M4 was measured using hemolytic assays. The enzyme was allowed to decay in the presence of a regulator and the activity of the remaining convertases was estimated; the cofactor activity of MCP, DAF-MCP chimeras and the mutants of D2D3M3M4 was measured by fluid phase cleavage assay; binding measurements of DAF, MCP, DAF-MCP chimeras and substitution mutants of D2D3M3M4 to C3b and C4b were performed by Biacore assay and the specific binding response was derived; the relative complement pathway-specific inhibitory activity of the multi-5 mutant with that of MCP, DAF, CR1 LHR-A (CCP1-3) and CR1 LHR-A$^{mut}$ (CCP1-3, D109N/E116K) was tested by WIESLAB® total complement ELISA assay and the level of serum activity in the presence of regulatory proteins was expressed as percent of activity measured without the proteins; the sequence of DAF and MCP were retrieved from UniProt (DAF ID: P08174 and MCP ID: P15529) and the D2D3M3M4 protein/mutant sequence was subjected to homology modeling based on DAF and MCP template structures (PDB id: 5FOA and 5F08 respectively)

using Modeller 9.11; the single best model was selected on the basis of the DOPE score; the naturally occurring residues of the chimera were mutated with mutant residues derived from experimental evidence; the mutation energy and its stability of the individual mutant structure of a chimera was calculated; ternary DAA complex (C3b-D2D3M3M4-Bb) was constructed and its interface analyzed; and the ternary complex (C3b-multi-4 mutant-FI) was constructed and used for MD simulations.

The present invention discloses a four domain DAF-MCP chimeric protein (DCP) having dual-activity regulation and enhanced affinity towards factor I and avidity towards C3b/C4b resulting in a mutant Multi-5 (DCP). DCP can be used as a lead molecule for designing further RCA-based therapeutics for treating pathological conditions involving the complement system.

The present invention discloses novel modified four domain DAF-MCP chimeric proteins with dual-activity regulation and further modified for enhancing interaction with factor I and C3b/C4b and the sequence ID 19 (DCP).

Another embodiment of the present invention discloses the engineered DAF-MCP chimeras having different combinations of DAF and MCP domains resulting in chimeric proteins having domains D2D3D4 from human DAF protein and M2M3M4 domains from MCP protein resulting in chimeric/mutants/proteins D2M2-4 with DAF linker, D2M2-4 with MCP linker, D2D3M3M4, and D2D3D4M4; the engineered protein D2D3M3M4 was further modified with gain-of function mutations for factor I interaction. The introduced mutations were 219ECREIY224 (Seq. ID. No. 100) to 219ICEKVL224 (Seq. ID. No. 101) and single amino acid substitutions F197I and P216K.

The engineered chimeric proteins of Seq Id Nos. 4 to 33 have dual-activity regulation, i.e., both DAA and CFA.

The present invention provides an optimal framework for a dual-activity protein having robust CP- and AP-DAA as well as C3b- and C4b-CFA activity and therefore potent inhibitory activity towards classical pathway (CP), alternative pathway (AP) and lectin pathway (LP).

Additionally, the dual activity regulator generated here (DCP, Seq. Id. No.19) may serve as a lead molecule for developing regulators of complement activation (RCA)-based therapeutics for treating pathological conditions involving the complement system. Due to the dual-activity protein and effectiveness of the chimeras of the present invention, they can also be used as reagents to inhibit CP, AP and LP activation in vitro and ex vivo assay systems. In addition, the specificity of these chimeras to AP, CP and LP makes them very useful in further elucidating the importance of different pathways in vivo in different disease conditions and inhibiting the pathology mediated by these pathways and hence for its use in elucidating and identifying specific conformational features required to provide dual activity and thereby effect on CP, AP and LP.

The chimeric proteins can be used in elucidating the different pathways in vitro and in vivo in different disease conditions and inhibiting the pathology mediated by these pathways. The chimeric proteins of the present invention, especially SEQ ID NOs: 4 to 33 may be useful to identify specific conformational features required to provide dual activity and thereby effect on CP, AP and LP.

It will be appreciated by those of skill in the art that a polypeptide mimic may serve equally well for the purpose of providing the specific backbone conformation and side-chain functionalities required for dual inhibition of CP, AP and LP. Accordingly, it is contemplated as being within the scope of the present invention to produce dual inhibitors, through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified polypeptides to inhibit complement activation In an embodiment, the engineered proteins of the present invention can be modified by the addition of polyethylene glycol (PEG) components to the peptide. As is well known in the art, PEGylation can increase the half-life of therapeutic peptides and proteins in vivo. In one embodiment, the PEG has an average molecular weight of about 1,000 to about 50,000. In another embodiment, the PEG has an average molecular weight of about 1,000 to about 20,000. In another embodiment, the PEG has an average molecular weight of about 1,000 to about 10,000. In an exemplary embodiment, the PEG has an average molecular weight of about 5,000. The polyethylene glycol may be a branched or straight chain, and preferably is a straight chain. The engineered proteins of the present invention can be covalently bonded to PEG via a linking group.

In an aspect, the polypeptide may be present in the pharmaceutical composition in the form of a physiologically acceptable ester or salt, or any such as in combination with a physiologically acceptable cation or anion, as is well known in the art. The polypeptide may also be derivatized before formulating it into a composition In an embodiment, the composition of the present invention may be administered as a composition. Such a pharmaceutical composition may consist of the engineered polypeptide of the present invention alone, in a form suitable for administration to a subject, or the pharmaceutical composition may comprise the active ingredient and one or more pharmaceutically acceptable carriers, one or more additional ingredients, or some combination of these.

The composition of the present invention may be administered in any one of the routes such as intravenously, orally, intraperitoneally, intradermally, intramuscularly, intranasally, subcutaneously, intranasally, intraspinal, intratracheal and intracranial.

The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In an embodiment, the novel engineered protein of the present invention is useful as therapeutics in diseases involving complement-mediated damage. Examples of complement-mediated diseases include, but are not limited to, paroxysmal nocturnal hemoglobinuria (PNH), age-related macular degeneration (AMD), atypical hemolytic uremic syndrome (aHUS), and dense deposit disease (DDD), autoimmune diseases such as experimental allergic neuritis, type II collagen-induced arthritis, myasthenia gravis, hemolytic anemia, glomerulonephritis, and immune complex-induced vasculitis, adult respiratory distress syndrome, stroke, heart attack, xenotransplantation, multiple sclerosis, burn injuries, extracorporeal dialysis and blood oxygenation.

In another embodiment the chimeric proteins described herein may be used for inhibiting complement activation in the serum, tissues or organs of a patient (human or animal), which can facilitate treatment of certain diseases or conditions, including but not limited to, age-related macular degeneration, rheumatoid arthritis, spinal cord injury, Parkinson's disease, Alzheimer's disease, cancer, and respiratory disorders such as asthma, chronic obstructive pulmonary disease (COPD), allergic inflammation, emphysema, bronchitis, bronchiecstasis, cyctic fibrosis, tuberculosis, pneumonia, respiratory distress syndrome (RDS-neonatal and adult), rhinitis and sinusitis. The engineered protein of the present invention may also be used for inhibition of complement-mediated pathologies in various diseases, expression on non-human cells and tissues to confer resistance to human complement-mediated damage during xeno-transplatation, inhibition of complement during extracorporeal circulation, complement inhibition for cancer therapy, expression on gene-therapy vectors (e.g., adeno-associated virus vector) for their protection from the human complement.

The proteins of the present invention may be used for inhibiting complement activation that occurs during cell or organ transplantation, or in the use of artificial organs or implants (e.g., by coating or otherwise treating the cells, organs, artificial organs or implants with a peptide of the invention). The proteins of the present invention may be used for inhibiting complement activation that occurs during extracorporeal shunting of physiological fluids.

EXAMPLES

The examples here below are provided for better understanding of the present invention and does not limit the scope of this invention.

Figure 2:
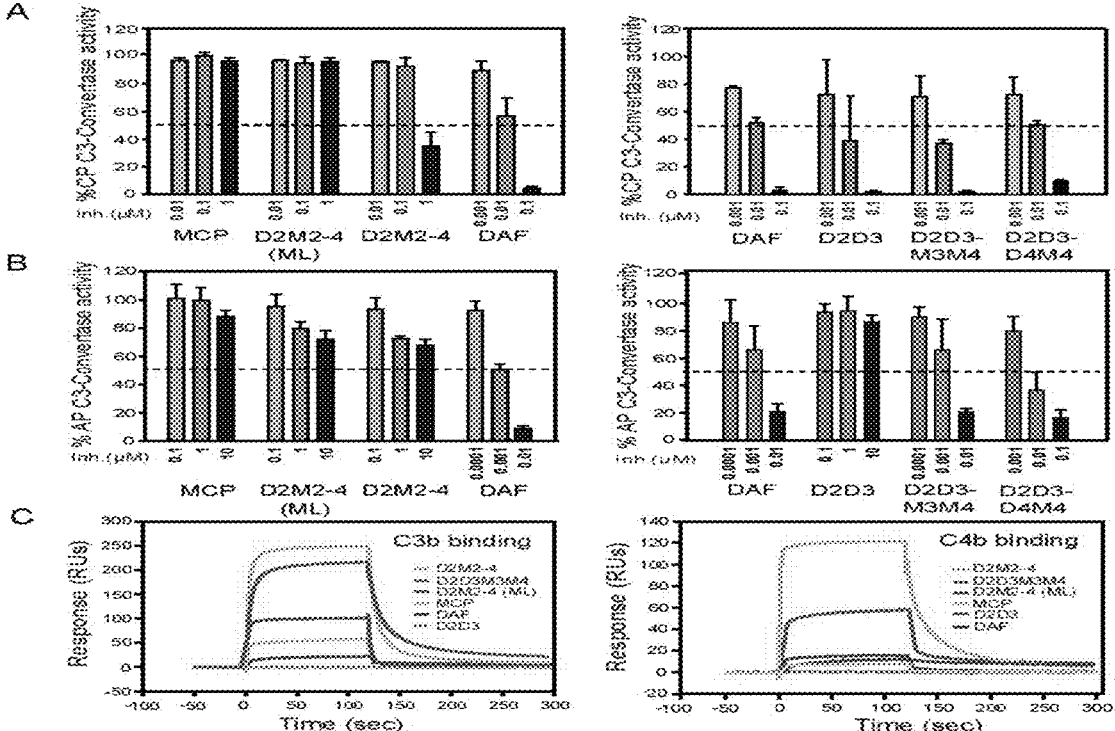
FIG. 2 depicts decay-accelerating activity and binding analysis of DAF-MCP chimeras.

Example 1. CCP2-3 of DAF Induce Decay, while CCP4 Aid by Serving as a C3b Binding Domain The role of each of the domains of DAF were determined using the domain swap strategy and mutants were created and tested. DAF is composed of four CCP modules and CCP2-4 are required for DAA. Further, swapping of one or more of MCP domains (M1-M3) and the linkers with the homologous domains of DAF (D2-D4) and the associated linkers [refer FIG. 1, The domains are numbered, and the boundaries are marked by the vertical lines. The numbers associated with the vertical lines represent the boundary residues and are according to uniprot numbering. The linkers connecting the DAF domains are marked in red, while the linkers connecting the MCP domains are marked in blue; the same colour scheme is used to depict the linkers in the DAF-MCP chimeras. D2M2-4 (ML) represents the chimera with the M1-M2 inter-domain linker.]) were swapped as MCP lacks DAA. The resulting mutants were tested for gain-of-function (refer FIG. 2). First, M1 was swapped and the attached inter-modular linker with D2 and the associated linker (mutant D2M2-4). Intriguingly, this substitution alone was sufficient to impart CP-DAA, though the mutant was ~30-fold less active compared to DAF. Further, the mutant displayed diminished AP-DAA highlighting the crucial role of other modules in the activity (refer FIGS. 2A & B, left panels). In FIG. 2A, Inh.' denotes inhibitor concentration. Data shown are mean±SD of three independent experiments summarized in Table S1. The dotted line denotes 50% activity.

TABLE S1

Summary of the complement regulatory activities of DAF, MCP and various DAF-MCP chimeric mutants

| Wild type/ Mutant | C3b CFA Time (min.) for 50% cleavage of C3b α'-chain | Relative C3b CFA | C4b CFA Time (min.) for 50% cleavage of C4b α-chain | C4b CFA | AP-DAA IC50 (nM) | Relative AP-DAA | CP-DAA IC50 (nM) | Relative CP-DAA |
|---|---|---|---|---|---|---|---|---|
| a. DAF-MCP chimeras | | | | | | | | |
| DAF | NA | NA | NA1 | NA 1 | 1.1 ± 0.3 | 1 | 14.5 ± 6.5 | 1 |
| MCP | 3.5 ± 1.7 | — | 16.5 ± 4.9 | — | NA | NA | NA | NA |
| D2M2-4 | ND | ND | ND | ND | >10 | <0.1 | 456.7 ± 60.3 | 0.03 |
| D2M2-4 (MCP linker) | ND | ND | ND | ND | >10 | <0.1 | >1000 | <0.01 |
| DAF | NA | NA | NA | NA | 2.3 ± 1.6 | 1 | 2.6 ± 2.6 | 1 |
| MCP | 2.1 ± 0.2 | 1 | 12 ± 6.8 | 1 | NA | NA | NA | NA |
| D2D3M3M4 | 80.7 ± 2.5 | 34 | 428.6 ± 77.8 | 35 | 2.4 ± 1.6 | 1 | 5.1 ± 4.5 | 0.5 |
| D2D3D4M4 | ND | ND | ND | ND | 5.6 ± 3.2 | 0.4 | 5.7 ± 8.0 | 0.4 |
| D2D3 | ND | ND | ND | ND | >10 | <0.2 | 10.9 ± 4.7 | <0.3 |
| b. Gain-of-function mutants of D2D3M3M4 | | | | | | | | |
| D2D3M3M4 | 82.6 ± 4.6 | 1 | 464.7 ± 65.4 | 1 | 2.1 ± 0.30 | 1 | 15.9 ± 6.7 | 1 |
| T192E | 74.3 ± 22.3 | 1.1 | 268 ± 61.6 | 1.7 | 2.3 ± 0.3 | 0.9 | 15.3 ± 6.7 | 1.0 |
| K195Y | complete loss | complete loss | >540 | <0.85 | >10 | 0.2 | >100 | 0.2 |
| F197I | 49.8 ± 15.2 | 1.7 | 66.7 ± 22 | 7 | 4.4 ± 1.6 | 0.5 | 30.7 ± 8.0 | 0.5 |
| S199K | 18.9 ± 2.6 | 4.4 | 181.3 ± 37.1 | 2.5 | 6.6 ± 2.3 | 0.3 | 21.7 ± 14.2 | 0.7 |
| T200Y | 103.3 ± 11.0 | 0.8 | 513.3 ± 46.2 | 0.9 | 3.7 ± 0.20 | 0.56 | 17.7 ± 6.4 | 0.9 |
| L205K | 103.6 ± 10.2 | 0.8 | 433.3 ± 94.5 | 1.07 | >10 | 0.2 | 9.2 ± 5.8 | 1.7 |
| P216K | 30.1 ± 4.1 | 2.7 | 93 ± 15.2 | 5 | 3.4 ± 0.5 | 0.6 | 21 ± 12 | 0.75 |
| multi-1 | 27.3 ± 3.2 | 3 | 443.3 ± 117.1 | 1.07 | 1.9 ± 0.6 | 1.1 | 22.6 ± 10.2 | 0.7 |
| Multi-2 | 4.3 ± 0.52 | 19.2 | 44.3 ± 17 | 10.5 | >10 | 0.2 | 5.8 ± 3.3 | 2.7 |
| multi-3 | 3.8 ± 2.1 | 22 | 16.7 ± 0.6 | 28 | 8.5 ± 1.6 | 0.24 | 12.3 ± 7.2 | 1.3 |
| c. Multi mutants of D2D3M3M4 | | | | | | | | |
| MCP | 4.5 ± 0.5 | 0.25 | 9.3 ± 1.2 | 1 | NA | NA | NA | NA |
| Multi-4 | 17.5 ± 5.5 | 0.25 | 5.5 ± 2.0 | 1.7 | >10 | <0.3 | 39.3 ± 7.8 | 0.4 |
| Multi-5 | 3.3 ± 0.5 | 1.3 | 3.1 ± 0.3 | 3 | 2.4 ± 0.4 | 1.3 | 12.7 ± 6.5 | 1.3 |
| DAF | NA | NA | 16.5 ± 4.9 | 1 | NA | NA | 16.5 ± 3.4 | 1 |

Boldface indicates the mutants and data with a >3-fold difference in activity, which was considered significant.
NA = No activity, ND = not determined.
Data are reported as mean ± SD of three independent experiments.
multi-2: linker substitution + S199K, multi-3: linker substitution + P216K + F197I.

Furthermore, the significance of the linker between D2-D3 (i.e., KKKS; net positive charge +3) in DAA was tested before swapping the next domain. Also, the recent DAF-C3b complex structure illustrated that the linker residues interact with C3b and besides positive electrostatic potential around the N-terminal CCP has been shown to enhance the initial recognition of C3b/C4b. Therefore, the D2-D3 linker in D2M2-4 was replaced with the neutral linker (YRET) of MCP present at the homologous position and the resultant mutant (D2M2-4-ML), showed no gain in CP-DAA (refer FIG. 2A, left panel). Further, the D2M2-4 mutant with MCP linker (D2M2-4-ML) also showed a considerable loss in binding to C3b and C4b compared to D2M2-4 mutant with DAF linker (D2M2-4) (refer FIG. 2C and FIG. 6A [The bar graphs represent RUs achieved at the steady state following binding of the respective protein (1p M) to C3b and C4b. The amount of C3b and C4b-biotin immobilised were 3330 RUs and 1630 RUs, respectively. The data is presented as mean±SD of three independent experiments]. The graph in FIG. 2C represents the sensogram overlays of binding interactions shown as response units on the y-axis. Binding was measured by flowing 1 µM of the respective proteins over the C3b-(Flow cell-2) and C4b-biotin (Flowcell-3) immobilised on a streptavidin chip. Data shown here is one of the three independent experiments shown in FIG. 6A.

The next mutant made was where the two N-terminal modules of DAF along with the associated linkers in MCP (D2D3M3M4) was substituted and the DAA of this mutant was assessed. It was observed that the mutant demonstrated CP-DAA as well as AP-DAA equal to that of DAF. The substitution of three domains of DAF along with the linkers in MCP (D2D3D4M4) did not result in any further increase in DAA and on the contrary, there was ~10-fold reduction in AP-DAA compared to DAF (refer FIG. 2B, right panel). The SPR data showed that the off-rate of this mutant for C3b is much slower than D2D3M3M4; its off-rate did not change for C4b [refer FIG. 6B (Data shown here is one of the three independent experiments shown in panel 6C)]. The data suggested that the slower off-rate affects the regulator's recycle rate for AP C3 convertase complexes, which results in its reduced AP-DAA. Together the above examples indicate that decay is induced only by CCP2-3 of DAF. It is therefore apparent that the D4 module in DAF merely plays a role of C3b binding domain, and its function can be substituted by M3-M4.

To gain further insight into the possible interactions of D2D3 modules in the D2D3M3M4 chimera with the AP C3 convertase subunits (i.e., C3b and Bb), the C3b-D2D3M3M4-Bb complex was modelled. Upon interface analysis, it was found that D2 and D3 interact with both C3b as well as Bb. Namely, D2 and D3 formed interfaces with α' N-terminal region (α'-NT) and macroglobulin-6 (MG6) domain of C3b (refer FIG. 7A). In addition, D2 and the D2-D3 linker formed contacts with α7-helix of Von Wille-brand factor type-A (VWA) domain in Bb, while D3 formed contacts with α7-helix, and α6-βF and α5-βE loops of VWA domain in Bb (refer FIG. 7B). It is known in previous studies that suggest that a stable conformation of the metal ion-dependent adhesion site (MIDAS site; formed by βA-α1, α3-α4 and βD-α5 loops) is critical for maintenance of a high-affinity conformation of VWA and the stability of the AP C3 convertase. Further, it was also proposed that α7-he-lix is allosterically coupled to the MIDAS site. The present modelling data show that D2 and D3 majorly interact with α6-βF and α5-βE loops in addition to the α7-helix. It is therefore likely that interaction of D2-D3 with these loops is important for allosteric changes in the MIDAS site leading to decay of Bb from C3b. FIG. 7 depicts the interface of the chimera with C3b and Bb in the modelled structure C3b-D2D3M3M4-Bb complex, which was analyzed by protein interface analysis program PISA, www.ebi.ac.uk/msd-srv/prot_int/pistart.html. The residues in the D2-D3 domains of D2D3M3M4 chimera that are at the interface of C3b (A) and Bb (B) are shown as vertical bars (which indicates buried surface area (BSA) score) and are indicated. The regions of Bb and C3b that interact with these residues of chimera are also marked above the vertical bars. The star marks repre-sent the residues which have been identified earlier by mutagenesis as important for DAA.

Figure 8:
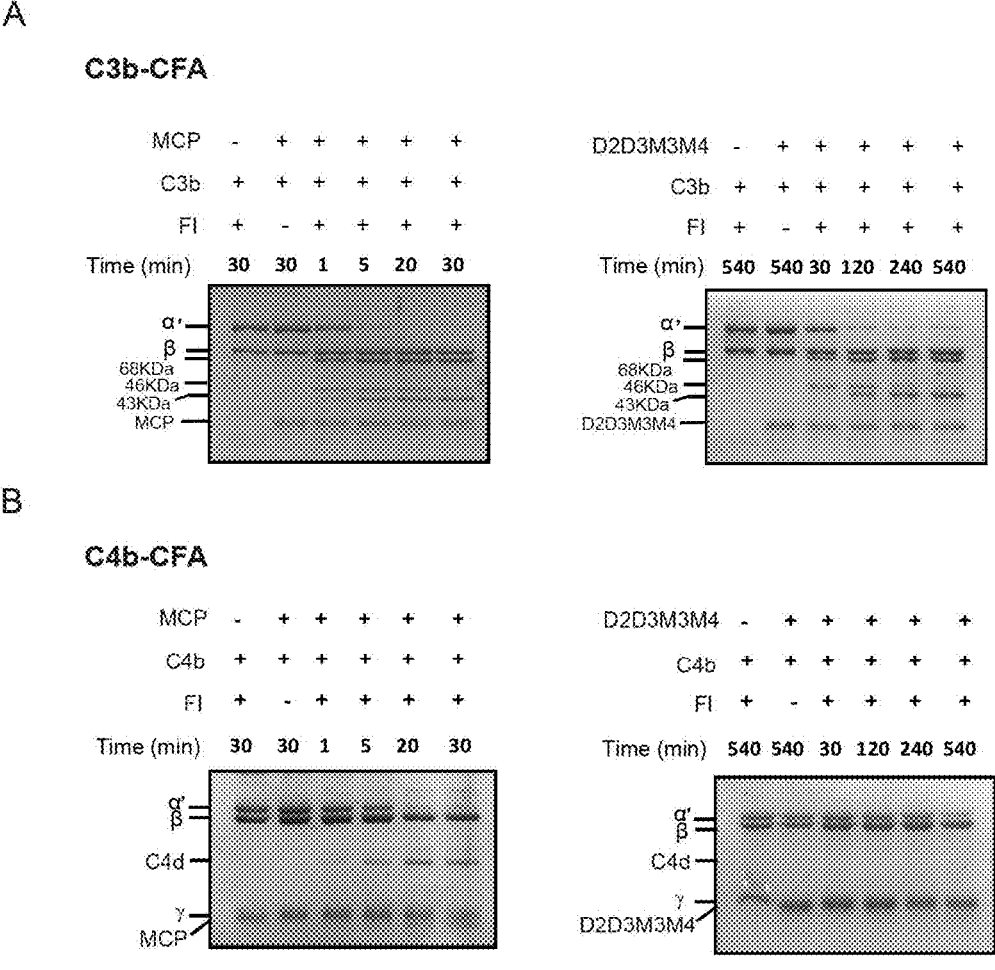
FIG. 8 depicts cofactor activity measurements of MCP and the DAF-MCP chimera D2D3M3M4.

Example 2. Factor I Interaction Sites on M2 as Well as M3 are Required for Optimum CFA of MCP The recently solved crystal structure of the complex of human C3b, mini FH, and FI showed that along with C3b both CCP2 and CCP3 of FH (homologous to M2 and M3 modules of MCP) make contact with FI. Further, CCP2-3 of viral RCA regulators (Kaposica and HVS CCPH) have been shown to drive CFA. These data suggested that FI interac-tion sites are likely conserved in CCP2 and CCP3 of human and viral RCA proteins. The relative importance of these sites in CFA, however, was not clear. It was not studied whether the FI site on M3 alone is sufficient to drive CFA in MCP. Hence, the CFA of D2D3M3M4 chimera, which lacks the M2 domain of MCP was examined. Remarkably, the chimera displayed CFA for C3b as well as C4b, although the CFA for C3b and C4b was 34- and 35-fold less, respectively, compared to that of MCP [FIG. 3A and FIG. 8 (The cofactor activity of these proteins was measured by incubating them with C3b (A) or C4b (B) and factor I at 37° C. for the indicated time in PBS. The cleavage products of C3b/C4b were observed by running them on SDS-PAGE (9% for C3b and 10% for C4b) under reducing conditions. In C3b-CFA, the α'-chain is cleaved into N-terminal 68-kDa and C-ter-minal 46-kDa fragments amongst which the 46-kDa frag-ment is further cleaved into 43-kDa fragment. In C4b-CFA, the α'-chain is cleaved into N-terminal 27-kDa, central C4d and C-terminal 16-kDa fragments; the C-terminal fragment is not visualized on the gel)]. These results, therefore, show that the FI interaction site present on M3 alone can contrib-ute functionally to CFA.

Figure 3:
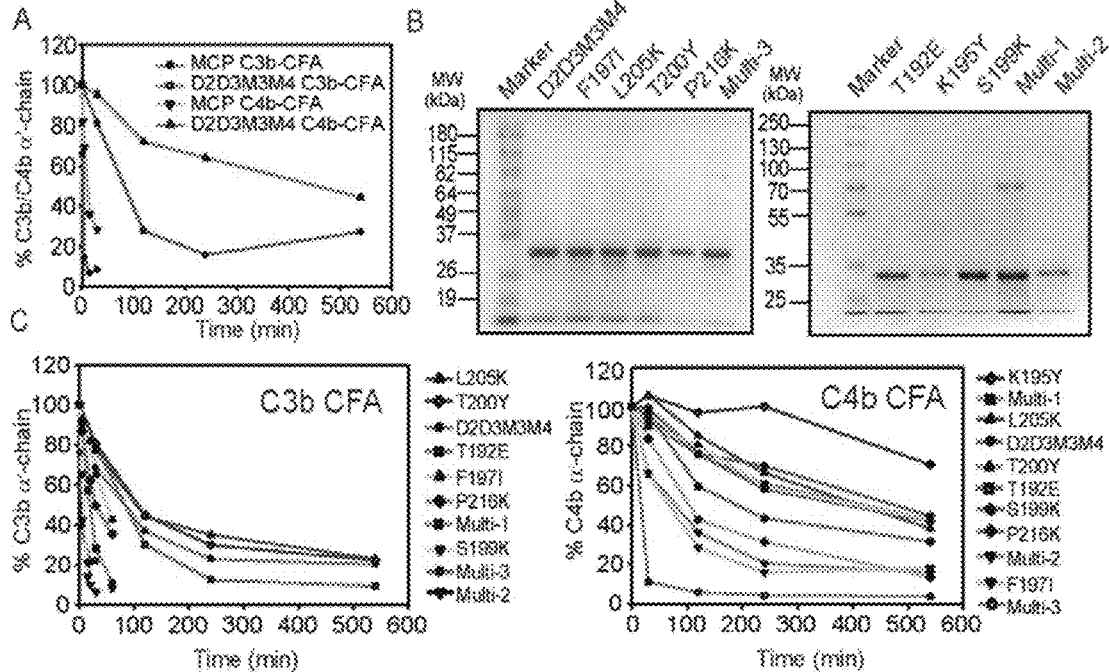
FIG. 3 depicts Cofactor activity (CFA) of D2D3M3M4 and its substitution mutants.

Having seen CFA in the D2D3M3M4 chimera, it was studied whether the CFA of this chimera can be enhanced by substituting the FI interaction site in the D3 domain (ho-mologous to M2), but without affecting its DAA. In other words, can potent DAA and CFA towards both the classical and alternative pathway C3 convertases coexist in a four CCP regulator? To answer this, the substitution of putative FI interacting residues in D3 was performed and the attached linker of D2D3M3M4 mutant based on the earlier mutagen-esis studies on the viral and human RCA proteins [FIG. 9 (Structure-based sequence alignment of CCP1-4 of DCP (multi-5 mutant) with homologous domains of various complement regulators. The modelled structure of DCP was aligned with experimental structures of DAF (PDB:1OJV), MCP (PDB:3O8E), Factor H (PDB:2WII), CR1 (PDB:1GKG), and SPICE (PDB:5FOB), and the modelled struc-tures of Kaposica and HVS CCPH based on CRRY (PDB:2XRB) using the PROMALS3D tool (http://prodata.swmed.edu/promals3d/). Blue arrows indicate the mutations (F197I, S199K, P216K, 219ECREIY224 (Seq. ID. No. 100) to ICEKVL (Seq. ID. No. 101)) that enhanced CFA in D2D3M3M4 chimera and orange arrows indicate the mutations (T192E, K195Y, T200Y, L205K) that did not enhance CFA. The highlighted residues indicate interfaces of the respective protein with C3b and factor I. The red boxes indicate previous mutations that resulted in loss in CFA and violet boxes indicate the mutations that resulted in loss in DAA. The numbering of the domains (shown in the beginning of each CCP sequence) is made according to the uniprot numbering)]. Herein, a total of 7 single and 3 multiresidue mutants of D2D3M3M4 [FIG. 3B (SDS-PAGE analysis of D2D3M3M4 and it's single and multiresidue mutants expressed in *E. coli*)] were generated. These muta-tions reside between Cys2-Cys4 region of D3 and the D3-M3 linker (ECREIY; Seq. ID. No. 100) as the earlier swapping of this region of DAF with the homologous region of MCP resulted in the incorporation of CFA in DAF. Biochemical analysis of the single and multiresidue mutants showed varying results—a complete loss to 28-fold gain in CFA [FIG. 3C (The order of the symbol key from top to bottom corresponds to the order of the lines (i.e., least to most active). Data shown in the graphs are mean of three independent experiments summarized in Table S1)]. Substi-tutions that showed a >2-fold gain in C3b CFA included single amino acid mutants like S199K, and P216K, and multiresidue mutant like multi-1 (linker substitution mutant—219ECREIY224 (Seq. ID. No. 100) to ICEKVL (Seq. ID. No. 101)), multi-2 (linker substitution+S199K) and multi-3 (215DPL217 to PKA; FIG. 10A). Likewise, mutations that showed >2-fold gain in C4b CFA included F197I, S199K, P216K, multi-2 and multi-3 (FIG. 3C, FIG. 10B and Table S1).

Next, the DAA of these D2D3M3M4 mutants was evalu-ated and looked for the loss in DAA, particularly in the mutants that showed a gain in CFA [FIG. 11 ((A) CP-DAA of the respective protein was measured by evaluating their ability to decay the pre-formed CP C3-convertase (C4b2a). (B) AP-DAA of the respective proteins was measured by evaluating their ability to decay the pre-formed AP C3-con-vertase (C3bBb). The data was normalized by considering the 100% C3-convertase activity to be equal to the activity without the inhibitor (Inh). Data shown are mean SD of three independent experiments) and Table S1]. Our results dem-onstrated that three mutants that exhibited a gain in CFA showed a loss in DAA. For example, >2-fold loss in AP-DAA was observed in S199K, and multi-2 and muti-3 mutants. The other three mutants (F197I, P216K and multi- 1) showed little or no loss in AP-DAA. Additionally, none of the gain in CFA mutants showed >2-fold loss in CP-DAA. These data, therefore, support the premise that coexistence of strong CFA and DAA in a structural framework of four CCPs is achievable.

Figure 9:
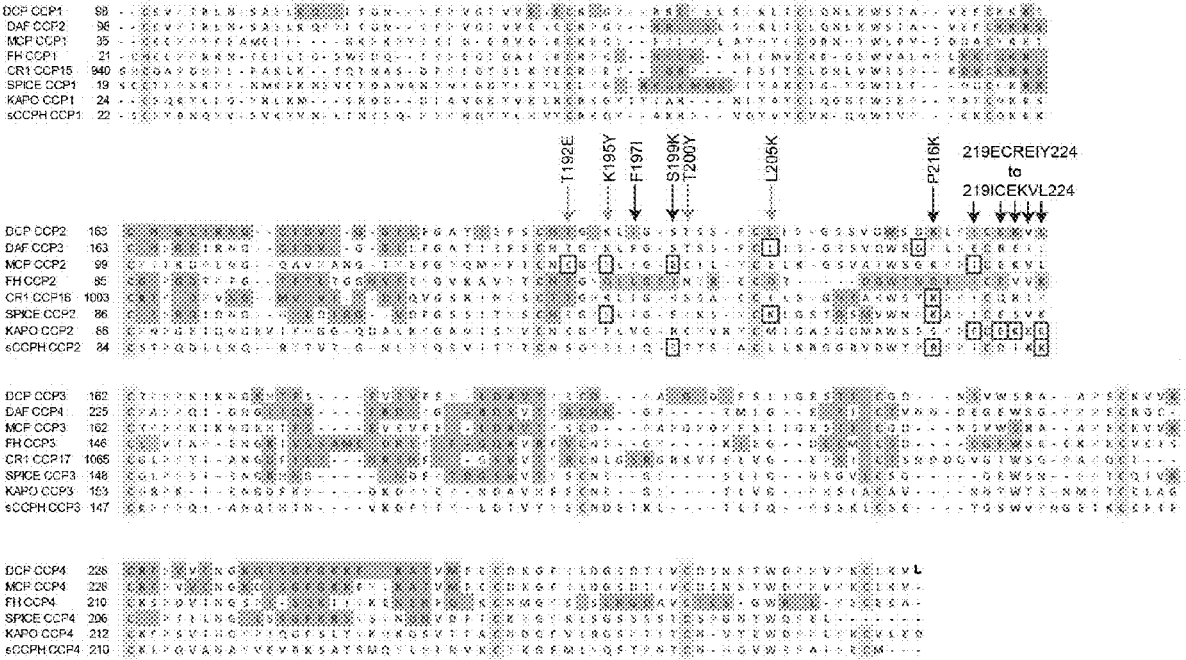
FIG. 9 depicts structure-based sequence alignment of CCP1-4 of DCP (multi-5 mutant) with homologous domains of various complement regulators. The blue arrows indicate the gain in CFA mutations, while the orange arrows indicate mutations that did not gain CFA.

To examine whether residues that provided gain in CFA are conserved in other RCA proteins that show CFA, the sequence alignment of various RCA proteins was performed (FIG. 9). It was observed that 5 of 10 residues that are associated with a gain in activity are conserved in position in other proteins with CFA. For example, a conserved isoleucine was seen at positions comparable with F197 and E219 of DAF. Similarly, positively charged residues were present at positions comparable with P216 and E222 of DAF, and negatively charged residues were present at the position analogous to R221 of DAF. Among these residues, mutation of isoleucine in MCP (19) at a position collinear to E219 of DAF, and of positively charged residues in CR1, SPICE, Kaposica and CCPH at positions corresponding to P216 and/or E222 of DAF have shown a loss in CFA (FIG. 9).

Example 3. Molecular Engineering of a Four CCP DAF-MCP Chimera Displaying DAA And CFA as Robust as the Parent Molecules In the above exercise, three single-residue mutants (F197I, S199K, P216K) and one multiresidue mutant (multi- (C4b-CFA) of MCP, multi-4 and multi-5,]. It was also determined if these mutations have any effect on the DAA of these mutants. The multi-4 mutant showed a complete loss in AP-DAA and ~2.5-fold loss in CP-DAA, while multi-5 displayed AP- and CP-DAA equivalent to DAF (FIGS. 4C & D and Table S1). Consistent with the loss in AP-DAA of multi-4 mutant, it's binding to C3b but not C4b, was found to be perturbed in comparison to D2D3M3M4 [FIG. 6C (The data is mean: SD of three independent experiments)].

Next, the regulatory activity of multi-5 mutant was tested on all the three major pathways of complement using WIESLAB® complement screen ELISA and compared it with DAF and MCP. The multi-5 was 2- to 7.5-fold more active than DAF and 35- to 225-fold more active than MCP in inhibiting the various pathways (FIG. 12C and Table S2A). Thus, the successful design of a four CCP molecule with efficient CFA and DAA was described. Based on the strong CFA and DAA of multi-5, this molecule is named as DCP (decay-cofactor protein). A comparison of the inhibitory potential of DCP with CR1 inhibitors such as LHR-A (CCP1-3) and its improved variant LHR-A$^{mut}$ (CCP1-3, D109N/E116K) showed that DCP was more potent than LHR-A (CCP1-3) in inhibiting the lectin and alternative pathways and more potent than LHR-A$^{mut}$ in inhibiting the alternative pathway (FIG. 12C and Table S2B). It, however, was more similar to LHR-A$^{mut}$ in inhibiting the classical and lectin pathways.

TABLE S2

| Comparison of complement regulatory activities of multi-5 (DCP) with DAF, MCP, LHR-A (CCP1-3), LHR-A (CCP1-3, D109N/E116K) | | | | | | |
| --- | --- | --- | --- | --- | --- | --- |
| Wild type/ Mutant | Inhibition of AP activity IC50 (μM) | Relative AP activity | Inhibition of LP activity IC50 (μM) | Relative LP activity | Inhibition of CP activity IC50 (μM) | Relative CP activity |
| DAF | 0.3 ± 0.2 | 1 | 0.11 ± 0.07 | 1 | 0.05 ± 0.02 | 1 |
| MCP | 1.4 ± 0.4 | 0.21 | 2.0 ± 0.3 | 0.05 | >2.25 | <0.02 |
| multi-5 (DCP) | 0.04 ± 0.01 | 7.5 | 0.05 ± 0.02 | 2.2 | 0.01 ± 0.02 | 5 |
| CR1 LHR-A (CCP1-3) | 0.64 ± 0.09 | 1 | 0.08 ± 0.04 | 1 | 0.06 ± 0.02 | 1 |
| CR1 LHR-A (CCP1-3, D109N/E116K) | 0.17 ± 0.02 | 3.8 | 0.015 ± 0.002 | 5.3 | 0.02 ± 0.005 | 3 |
| multi-5 (DCP) | 0.06 ± 0.008 | 10.6 | 0.02 ± 0.004 | 4 | 0.04 ± 0.02 | 1.5 |

Boldface indicates the mutants and data with a >2-fold difference in activity, which was considered significant.
Data are reported as mean ± SD of three independent experiments.
AP, alternative pathway;
CP, classical pathway;
LP, lectin pathway.

1, i.e., linker substitution mutant) showed moderate to a considerable increase in CFA (FIG. 3C and Table S1, FIGS. 10A and 10B). It was therefore conceivable that collective substitution of these residues in D2D3M3M4 chimera is likely to result in the generation of a molecule with DAA and CFA as strong as DAF and MCP. Thus two multi-variants of D2D3M3M4 were generated: one where all the above mutations were incorporated in D2D3M3M4 (multi-4), and the other where all, but S199K, were incorporated in D2D3M3M4 (multi-5) as this mutation increases CFA, but decreases AP-DAA (Table S1). Examination of CFA of these two mutants showed that both the mutants have good C3b CFA, but multi-5 was equivalent to MCP (FIG. 4A and FIG. 12A). Both the mutants however displayed better C4b CFA (~2- to 3-fold) compared to MCP (FIG. 4B and FIG. 12B [FIG. 12 (A) depicts C3b cofactor activity (C3b-CFA) of MCP, multi-4 and multi-5, (B) depicts C4b cofactor activity

Example 4. Molecular Dynamics Simulations of the C3b-Multi-4 Mutant-FI Complex Reveal Information on Interactions of Mutated Residues in the Chimera with FI The exercise detailed above clearly identified the residues that impart gain in CFA when substituted in the D2D3M3M4 mutant. To decipher the influence of these residues on molecular interactions with FI and C3b, a structural model of a ternary complex of C3b-multi-4 mutant-FI was generated by replacing FH with the chimera in the C3b-FH-FI structure. The predicted ternary complex was subjected to molecular dynamics simulations (for 50 ns) to highlight the effects of these mutations on the stability and their role in interactions with FI and C3b (refer FIG. 5). The RMSD was calculated to characterize structural variations in the protein for the entire simulation period (refer to FIG. 13Ai). The RMSD was found to be stable for the entire simulation period with small drifts and plateaus. The RMSF plot was calculated for the chimera to understand the residue-wise fluctuation. The RMSF plot revealed a similar fluctuation pattern between the D2D3M3M4 chimera and multi-4 mutant structure (FIG. 13Aii & FIG. 13Aiii) ((i) Backbone RMSD of C3b-multi4-FI complex for 50 ns simulation. (ii) Root mean square fluctuation (RMSF) of chimera residues for the entire simulation time. (iii) Plot showing the RMSF of the multi-4 mutant residues located in the region where gain-of-function mutations have been identified).

The interactions of the chimera with C3b and FI evaluated in the simulated structure showed that I197 and I219 of the chimera are accommodated in a hydrophobic pocket of FI formed by residues W393, P402, L404, I407, V408, I409, and Y411. Similarly, L224 (linker residue) sits in the adjacent hydrophobic pocket of FI formed by residues I357, G362, I363, A360, V396, V397, W399, and I400 (refer FIG. 5B (Left panel, I197 and I219 sit in the upper hydrophobic pocket formed by the residues W393, P402, L404, I407, V408, I409, and Y411, while L224 sits in a lower hydrophobic pocket formed by residues I357, G362, I363, A360, V396, V397, W399 and I400. Right panel, the hydrophobic pockets shown on the left panel are shown again and marked with circles)). Thus, the hydrophobic interactions of these residues seem crucial to enhance the stability of the chimera and FI, as reported previously for FH-FL. Furthermore, residues K216 and Glu221 located in the linker region interact with residues D438 and K358 of FI through salt bridge interactions. The mutant residues K199 and K222 do not show any interaction as sidechain orientations are away from the FI interface. This explains as to why the reversion of K199 to Ser (in multi-5) has no significant effect on CFA. The S199 residue, however, has a high BSA score with respect to contact with α7 and α 6-βF loops of the VWA domain of Bb (refer FIG. 7B) The interface of the chimera with C3b and Bb in the modelled structure C3b-D2D3M3M4-Bb complex was analysed by protein interface analysis program PISA, www.ebi.ac.uk/msd-srv/prot_int/pistart.html. The residues in the D2-D3 domains of D2D3M3M4 chimera that are at the interface of C3b (A) and Bb (B) are shown as vertical bars (which indicates buried surface area (BSA) score). The regions of Bb and C3b that interact with these residues of chimera are also marked above the vertical bars. The star marks represent the residues which have been identified earlier by mutagenesis as important for DAA and, therefore, possibly accounts for a major gain in AP-DAA following K199S reversion. Interestingly, D403 of FI acts as bridging residue by forming hydrogen bonds with K195 of D3 and S214 of M3 and might be involved in D3-M3 domain coordination of the chimera (refer FIG. 14C (note—Lys195 show charge interaction with Asp403 of FI which is helped by its hydrogen bond with Ser214 of the M3 domain. V178 display a pi-alkyl bond with Trp399 of FI)). Additionally, residues E179 and E177 form salt bridge network with residue R480 of FI. The residue V178 of chimera forms pi-alkyl interaction with W399 of FI (refer FIG. 14C). Overall, the interaction patterns of the linker and associated regions of the chimera with FI are congruent with our experimental study. The interaction of the multi-4 mutant with the C3b domain is depicted in FIG. 14A (The zoomed views show interacting residues in α'-NT, MG6, MG2, CUB, MG1, and TED domains) & FIG. 14B (The C3b interacting residues of multi-4 mutant is according to the C3b domains with which it interacts.). The domain-specific interactions were found to be similar to DAF and MCP.

Example 5. Construction of DAF, MCP, DAF-MCP Chimeras and Substitution Mutants of D2D3M3M4 and CR1 LHR-A (CCP1-3)

Human DAF (D1-D4) and MCP (M1-M4) were amplified from their respective cDNAs and cloned into the yeast expression vector pPICZα (Invitrogen, Carlsbad, CA) as well as the bacterial expression vector pET-28b. The DAF-MCP chimeras were constructed using the gene splicing and overlap extension method as described and then cloned either into the yeast expression vector pPICZα or into the bacterial expression vector pET-28b. The CR1 LHR-A (CCP1-3) was amplified from CR1 cDNA and cloned in the pET-28b for its expression. The primer sets used to amplify the required regions of DAF, MCP and CR1 are listed in Table S3. The substitution mutants of D2D3M3M4 and CR1 LHR-A (CCP1-3) were constructed using the QUICK-CHANGE™ site-directed mutagenesis kit II (Stratagene, La Jolla, CA) and cloned into the bacterial expression vector pET-28b. The mutagenic primers utilized for the site-directed mutagenesis are listed in Table S3. The DAF deletion mutant D2-D3 was amplified from DAF cDNA and cloned into pET-28b; primer sets used are listed in Table S3. Following cloning, all the constructs were validated by DNA sequencing (1st Base Laboratories Sdn Bhd, Malaysia). For expression, the proteins/mutants cloned into pPICZα were integrated into *Pichia pastoris* as per the manufacturer's protocol, whereas those cloned into pET-28b were transformed into *Escherichia coli* BL21 (DE3) cells.

TABLE S3

| Primers used for the cloning of wild-type DAF, MCP and DAF-MCP region swap mutants | | | |
|---|---|---|---|
| Wild type/Mutant | Amplified product | Primer | Sequence |
| DAF-pichia | D1-D4 | Forward | ggAATTCgACTGTggCCTTCCCCCAgATg (Seq. ID. No. 34) |
| DAF-pichia | D1-D4 | Reverse | gCTCTAgA TTATCTgCATTCAggTggTgggCC (Seq. ID. No. 35) |
| DAF | D1-D4 | Forward | ggAATTCCATATggACTgTggCCTTCCCCCAgATg (Seq. ID. No. 36) |
| DAF | D1-D4 | Reverse | CCgCTCgAgTCTgCATTCAggTggTgggCCAC (Seq. ID. No. 37) |
| MCP-pichia | M1-M4 | Forward | ggAATTCgCCTgTgAggAgCCACCAAC (Seq. ID. No. 38) |
| MCP-pichia | M1-M4 | Reverse | gCTCTAgATTAAAgACACTTTggAACTggggg (Seq. ID. No. 39) |

TABLE S3-continued

Primers used for the cloning of wild-type DAF, MCP and DAF-MCP region swap
mutants

| Wild type/Mutant | Amplified product | Primer | Sequence |
|---|---|---|---|
| MCP | M1-M4 | Forward | CATgCCATgggCAAgTgTgAggAgCCACCAACATTTgAAgCTATggAgCTCATTggTAAACCAAAACCC (Seq. ID. No. 40) |
| MCP | M1-M4 | Reverse | CGCAAGCTTAAGACACTTTGGAACTGGG (Seq. ID. No. 41) |
| D2D3 | D2D3 | Forward | CCCAAgCTTTgCgAggTgCCAACAAggCTAAATTC (Seq. ID. No. 42) |
| D2D3 | D2D3 | Reverse | CCgCTCgAgATAAATTTCTCTgCACTCTggCAACgg (Seq. ID. No. 43) |
| D2M2-4 | D2 | Forward | ggAATTCTgCgAggTgCCAACAAggC (Seq. ID. No. 44) |
| D2M2-4 | D2 | Reverse | CCCgTATATATggACATgATTTCTTTTTACAAAATTCgACTg (Seq. ID. No. 45) |
| D2M2-4 | M2M3M4 | Forward | CgAATTTTgTAAAAgAAATCATgTCCATATATACgggATCCTTTAAATgg (Seq. ID. No. 46) |
| D2M2-4 | M2M3M4 | Reverse | gCTCTAgAgCAAgACACTTTggAACTgggggg (Seq. ID. No. 47) |
| D2M2-4 (ML) | D2 (ML) | Forward | ggAATTCTgCgAggTgCCAACAAggC (Seq. ID. No. 48) |
| D2M2-4 (ML) | D2 (ML) | Reverse | ggACATgTTTCTCTATAACAAAATTCgACTgCTgTggACC (Seq. ID. No. 49) |
| D2M2-4(ML) | M2M3M4 | Forward | CAgCAgTCgAATTTTgTTATAgAgAAACATgTCCATATATACg (Seq. ID. No. 50) |
| D2M2-4(ML) | M2M3M4 | Reverse | gCTCTAgAgCAAgACACTTTggAACTgggggg (Seq. ID. No. 51) |
| D2D3M3M4 | D2D3 | Forward | CATgCCATgggCTgCgAggTCCCAACAAgg (Seq. ID. No. 52) |
| D2D3M3M4 | D2D3 | Reverse | ggAggTggTgTACAATAAATTTCTCTgCACTCTggC (Seq. ID. No. 53) |
| D2D3M3M4 | M3M4 | Forward | gTgCAgAgAAATTTATTgTACACCACCTCCAAAAATAAAAAATgg (Seq. ID. No. 54) |
| D2D3M3M4 | M3M4 | Reverse | CGCAAGCTTAAgACACTTTggAACTggg (Seq. ID. No. 55) |
| D2D3D4M4 | D2D3D4 | Forward | CATgCCATgggCTgCgAggTICCCAACAAgg (Seq. ID. No. 56) |
| D2D3D4M4 | D2D3D4 | Reverse | gACATTTgACCACTTTgCATTCAggTggTgggCCAC (Seq. ID. No. 57) |
| D2D3D4M4 | M4 (ML) | Forward | ggACCACCTgAATgCAAAgTggTCAAATgTCgATTTCC (Seq. ID. No. 58) |
| D2D3D4M4 | M4 (ML) | Reverse | CgCAAgCTTAAgACACTTTggAACTggg (Seq. ID. No. 59) |
| LHR-A(CR1CCP1-3D109N) | — | Forward | CATgCATCATCTCAggTAACACTgTCATTTgggATAAT (Seq. ID. No. 60) |
| | — | Reverse | ATTATCCCAAATgCACAgTgTTACCTgAgATgATgCATg (Seq. ID. No. 61) |
| LHR-A(CR1CCP1-3E116K) | — | Forward | CTgTCATTTgggATAATAAAACACCTATTTgTgACA (Seq. ID. No. 62) |
| | — | Reverse | CTgCACAAATAggTgTTTTATTATCCCAAATgACAg (Seq. ID. No. 63) |

* CCP Domains of DAF and MCP are denoted by D and M, respectively, and numbers denote the respective regulator.
* Restriction sites are underlined. Boldface region indicates the overlapping region of primer with the cloning region/linker at 5' and/or 3' regions. Italics letters represent the mutation.
* Pichia indicates the proteins were cloned in pPICZA vector. All other proteins were cloned in pET-28b vector.

Example 6. Expression and Purification of DAF, MCP, DAF-MCP Chimeras and Substitution Mutants of D2D3M3M4

Human DAF, MCP and the DAF-MCP chimeras namely D2M2-4 (chimera containing the DAF linker between D2-D3) and D2M2-4-ML (chimera containing the linker between M1-M2) were expressed in *P. pastoris* as described and purified as below. Firstly, all the expressed proteins were concentrated by ultrafiltration and precipitated using 80% ammonium sulphate on ice. The pellets obtained were then dissolved in PBS and processed further. For purification of DAF, the pellet dissolved in PBS was mixed with 500 mM NaCl and loaded onto a DEAE-SEPHACEL™ column (Sigma, St. Louis, Mo.) pre-equilibrated with PBS containing 500 mM NaCl. The flow-through obtained was then passed through a PD-10 column (GE Healthcare Life Sciences, Pittsburgh, PA) for buffer exchange and loaded onto a MONO Q™ column in 20 mM Tris, pH 8.0. Elution of the bound DAF was achieved by passing a linear gradient of 0 to 500 mM NaCl. For purification of MCP and the chimeras (D2M2-4-DL and D2M2-4-ML), the pellet dissolved in PBS was subjected to buffer exchange against 10 mM sodium phosphate, pH 7.4 and loaded onto a DEAE-SEPHACEL™ column in the same buffer. The bound proteins were eluted with a linear gradient of 0-500 mM NaCl. The fractions containing MCP or the respective chimera were pooled, exchanged into 20 mM Tris, pH 8.0, loaded onto MONO Q™ column and eluted with a linear gradient of 0-500 mM NaCl. Eluted fractions in all the above purifications were subjected to SDS-PAGE and Western blot analysis using the appropriate antibody (refer FIGS. 15A and 15B). All the purified proteins were dialyzed in PBS and concentrated by ultrafiltration; purity of all the proteins exceeded 95% as determined by SDS-PAGE (In FIG. 15A (i) DAF, MCP and the DAF-MCP chimeras. (ii) Single residue mutants of D2D3M3M4. (iii) Multi-residue mutants of D2D3M3M4—multi-1, multi-2, multi-3, multi-4 and multi-5 along with CR1 LHR-A (CCP1-3) and it's double mutant CR1 LHR-A (CCP1-3 D109N/E116K) and (Proteins were loaded onto SUPEROSE-12™ column (GE Healthcare Life Sciences) pre-equilibrated with PBS (pH 7.4). The gel filtration standards (Bio-Rad) used were: a, Thyroglobulin (670,000 Da); b, Gamma globulin (158,000 Da); c, Ovalbumin (44,000 Da); d, Myoglobin (17,000 Da); e, Vitamin B-12 (1,350 Da)) and 15B (i) DAF, MCP and the DAF-MCP chimeras. (ii) Single and multi-residue (multi-1) mutants of D2D3M3M4. (iii) multi-residue mutants of D2D3M3M4 (iv) CR1 LHR-A CCP(1-3) and its double mutant CR1 LHR-A (CCP1-3 D109N/E116K) and (All the proteins were run on 9% SDS-PAGE under reducing (R) and non-reducing (NR) conditions and were stained with Coomassie blue)).

Human DAF and MCP were also expressed in *E. coli*. Other mutants that were expressed in *E. coli* include the DAF mutant D2D3, DAF-MCP chimeras D2D3M3M4 and D2D3D4M4, and substitution mutants of D2D3M3M4. The CR1 LHR-A (CCP1-3) and its mutant CR1 LHR-A$^{mut}$ (CCP1-3, D109N/E116K) were also expressed in *E. coli*. Expression of these proteins was performed essentially as described earlier. In brief, proteins were purified using Ni-NTA column in the presence of urea as they were present in the inclusion bodies. They were then subjected to refolding by rapid dilution method and passed through gel filtration column (SUPEROSE-12™; GE Healthcare Life Sciences). All the proteins refolded properly as judged by the presence of a monodisperse population in the size exclusion chromatography profiles, and mobility differences on SDS- PAGE under reducing and non-reducing conditions (an indication of disulfide bond formation) (FIGS. 15A and 15B). The purity of all the *E. coli* expressed proteins exceeded 95% as determined by SDS-PAGE.

Example 7. CP and AP C3-Convertase Decay-Accelerating Activity Assay

Figure 4:
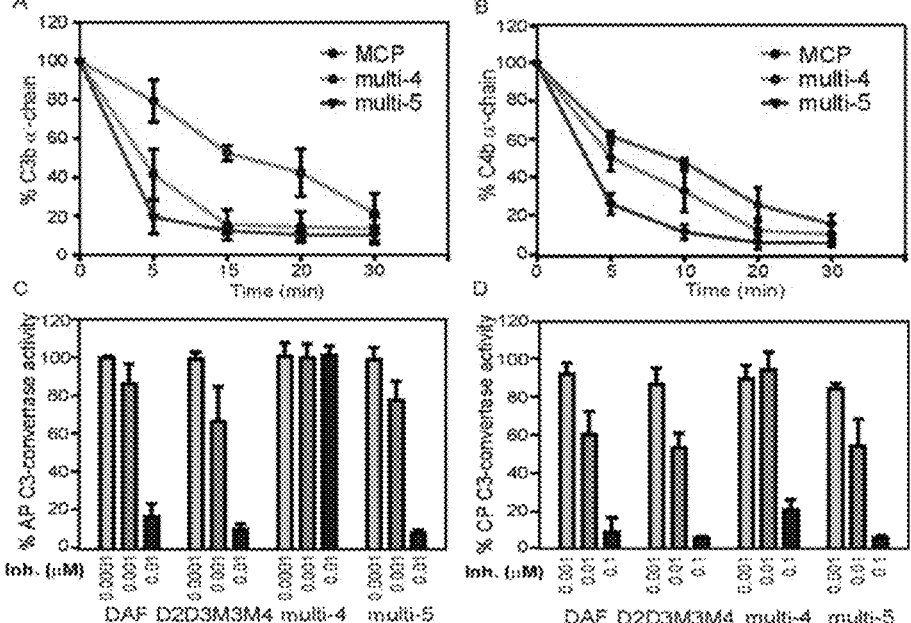
FIG. 4 depicts substitution of the putative factor I interaction sites in D3 domain of D2D3M3M4 generates a molecule with CP- and AP-DAA, and C3b- and C4b-CFA.

The classical/lectin and alternative pathway C3-convertase decay-accelerating activity of DAF, DAF-MCP chimeras and the mutants of D2D3M3M4 was measured using hemolytic assays as previously described. Briefly, the respective convertases were formed on erythrocytes using purified complement components and allowed to decay in the presence or absence of a regulator. The activity of the remaining convertases was estimated by incubating the erythrocytes with guinea pig sera containing 40 mM EDTA (a source of C3-C9) and measuring lysis. The data obtained were normalized by considering 100% C3-convertase activity equal to the lysis that occurred in the absence of an inhibitor. The activity obtained was then plotted against the concentration to determine the inhibitor concentration required to inhibit 50% of enzyme activity (IC$_{50}$). Each of the inhibitors was tested at various concentrations to determine the concentration range at which it inhibits and then it was tested at three specific concentrations to determine the IC$_{50}$ as performed earlier (FIGS. 2, 4, 11).

Example 8. C3b and C4b Cofactor Activity Assay

The cofactor activity of MCP, DAF-MCP chimeras and the mutants of D2D3M3M4 was measured by incubating each of the regulator with C3b (purified as described) or C4b (Complement Technology, Inc., Tyler, TX) and serine protease factor I in PBS and measuring C3b/C4b cleavage. Briefly, C3b (10 μg) or C4b (15 μg) was mixed with 1 μM (for C3b) or 2 μM (for C4b) of the regulator and 250 ng (for C3b) or 500 ng (for C4b) of factor I in a total reaction volume of 75 μl and incubated at 37° C. Aliquots of 15 μl were then taken out at the indicated time periods, mixed with the sample buffer containing DTT and ran on either 9% (for C3b) or 10% (for C4b) SDS-PAGE gels for determining cleavage of α'-chain of C3b/C4b. The percentage of α'-chain cleaved was calculated by densitometric analysis using the QUANTITY ONE™ software (Bio-Rad); the amount of α'-chain was normalized to β-chain (loading control). A plot of percent cleavage of the α'-chain of C3b/C4b against time provided the 50% cleavage of α'-chain of C3b/C4b. Activity differences of >3-fold were considered significant Table S1).

Example 9. Surface Plasmon Resonance Measurements

Figure 6:
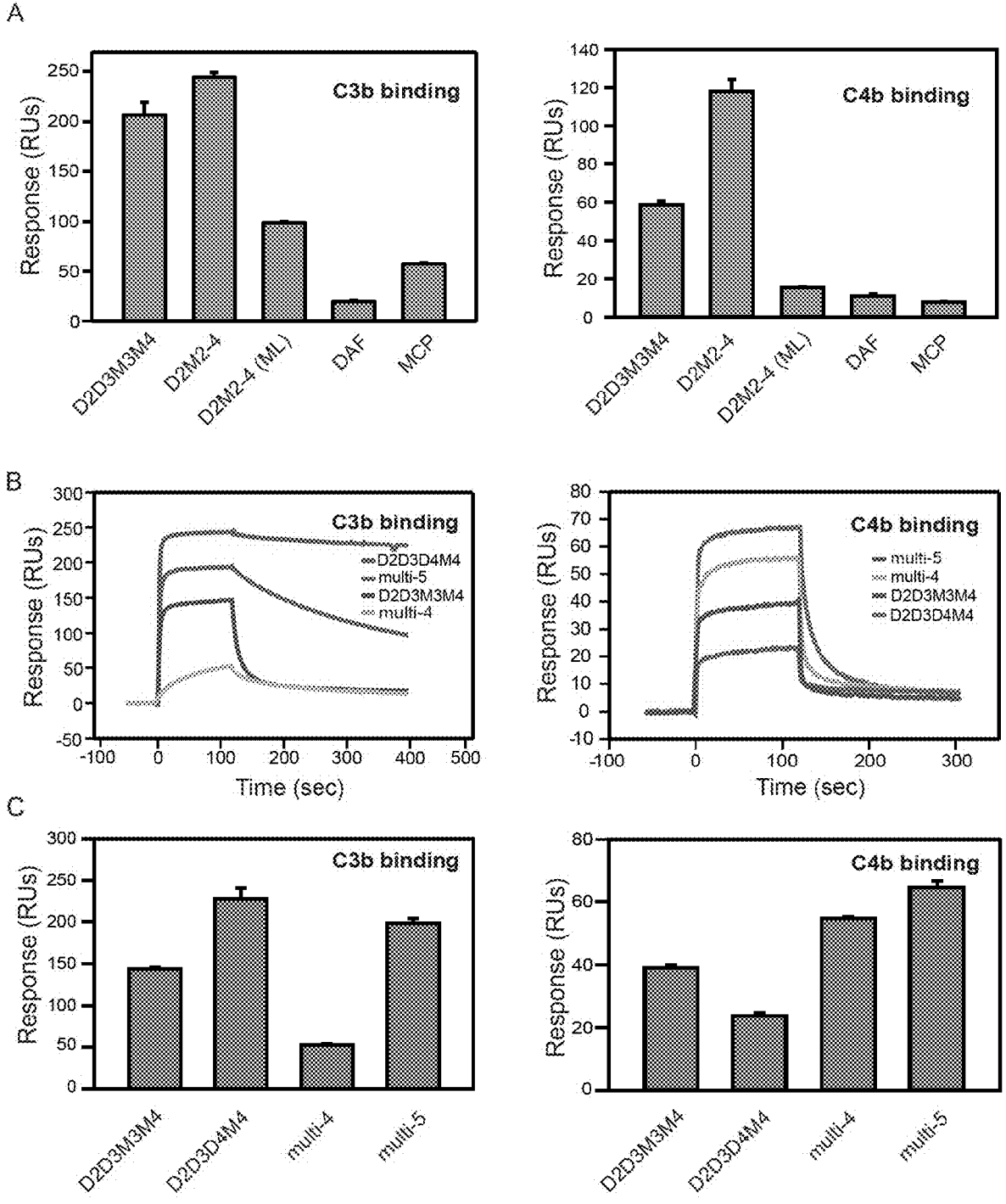
FIG. 6 depicts binding analysis of DAF, MCP and the DAF-MCP chimeras to C3b and C4b.

Binding measurements of DAF, MCP, DAF-MCP chimeras and substitution mutants of D2D3M3M4 to C3b and C4b were performed on BIACORE 2000™ (Biacore AB, Uppsala, Sweden). First, the target proteins C3b and C4b biotinylated at their free —SH groups using EZ-LINK™ PEO-maleimide-activated biotin (Pierce, Rockford, IL), were immobilized on flow cells 2 and 3 of a streptavidin chip (Sensor Chip SA; Biacore AB). The flow cell-1 immobilized with biotinylated bovine serum albumin (BSA) served as the control flow cell. Next, each of the analytes (DAF, MCP and DAF-MCP chimeras and the mutants of D2D3M3M4) in PBS-T was flowed over the chip at 50 μl/min at 25° C. to measure binding. The association and dissociation of the analyte was measured for 120 and 180 s, respectively, and chip regeneration was achieved by 30 s pulses of 0.2 M sodium carbonate, pH 9.5. The specific binding response was derived by subtracting the control flow cell data from the target protein immobilized flow cell data (FIGS. 2C & 6B).

Example 10. ELISA for Measurement of Effect on CP, AP and LP

The WIESLAB® complement system screen ELISA assay (Euro-Diagnostica, Malmo, Sweden) was employed to test the relative complement pathway-specific inhibitory activity of the multi-5 mutant with that of MCP, DAF, CR1 LHR-A (CCP1-3) and CR1 LHR-A$^{mut}$(CCP1-3, D109N/E116K). Herein, the graded concentrations of each of the test proteins were made in the pathway-specific diluent and mixed with a fixed percentage of normal human serum concentration as detailed in the manual. The reaction mixtures (100 μl) were then added to the microtiter wells coated with pathway-specific activators and kept for 60 min at 37° C. Thereafter, wells were washed three times with the washing solution supplied in the kit and incubated for 30 min at room temperature with an antibody against C5b-9 (100 μl) labelled with alkaline-phosphatase. The wells were again washed three times with the washing solution and incubated for 30 min at room temperature with the substrate (100 μl). The absorbance was read at 405 nm on a microplate reader. The level of serum activity in the presence of regulatory proteins was expressed as percent of activity measured without the proteins (FIG. 12C).

Example 11. Modelling of D2D3M3M4 Chimera

Figure 5:
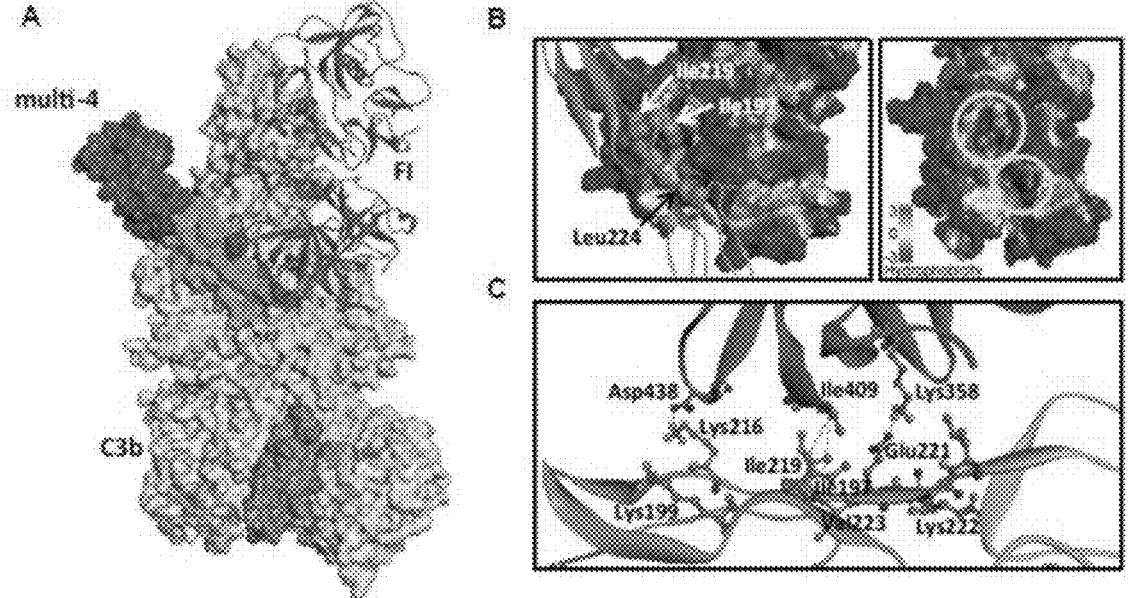
FIG. 5 depicts mapping of factor I interaction sites in the C3b-multi-4 mutant-FI trimolecular complex.

The sequence of DAF (UniProt ID: P08174) and MCP (UniProt ID: P15529) were retrieved from the UniProt Protein sequence database. The sequence of D2D3 extracted from DAF and M3M4 from MCP to construct chimera sequence. The structural co-ordinates of DAF and MCP were separated from co-crystal structures of C3b-DAF (PDB id: 5FOA) and C3b-MCP (PDB id: 5FO8) respectively. The structure of chimera (D2D3M3M4) based on DAF and MCP template structures was modelled using Modeller 9.11 implemented in Discovery Studio v 3.5; Dassault Systèmes BIOVIA 2016). Subsequently, a loop modelling option was used to model the loop regions. The single best model was selected on the basis of the DOPE score. The stereochemical quality of the predicted model was evaluated using PRO-CHECK and PROSA-Web servers. Then, using Discovery studio, naturally occurring residues of the chimera were mutated with mutant residues derived from experimental evidence as described in the main text. The individual mutant structure of a chimera was then subjected to a calculation of its mutational energy and its stability (FIG. 5).

Example 12. Construction of Ternary DAA Complex (C3b-D2D3M3M4-Bb) and its Interface Analysis The DAA ternary complex with chimera D2D3M3M4 as the regulator was modelled by using the template structures of DAF-C3b (PDB id: 5FOA) and C3bBb (PDB id: 2WIN) along with the above-modelled structure of chimera D2D3M3M4. Briefly, the D2D3M3M4 chimera was superimposed to DAF in the C3b-DAF structure to make the D2D3M3M4-C3b complex. The D2D3M3M4-C3b and C3bBb were then superimposed together with reference to C3b molecule to generate a ternary model of C3b-

D2D3M3M4-Bb. The final ternary complex was subjected to energy minimization by the steepest descent method. The interface analysis of the ternary complex was performed by PISA (Protein interface analysis program, www.ebi.ac.uk/msd-srv/prot_int/pistart.html) to understand the interaction between C3b and D2D3M3M4 as well as Bb and D2D3M3M4 (FIG. 7).

Example 13. Construction of Ternary Complex (C3b-Multi-4 Mutant-FI) and MD Simulation The ternary complex of C3b-FH-FI (PDB id: 5032) was retrieved from PDB and the model of the multi-4 mutant was superimposed against the FH molecule of the complex. The coordinates of FH were removed and a ternary complex of C3b-multi-4 mutant-FI was generated using UCSF Chimera. The generated ternary complex of C3b-multi-4 mutant-FI was then subjected to MD simulation with OPLS-AA force field using the GROMACS 5.0.4 package. The protein was solvated with simple point charge (SPC) water model and neutralized with NA+ counter ions. The solvated structure was minimized by steepest descent energy minimization followed by 500 ps equilibration in NVT ensemble with position restraints applied to protein. Subsequently, the system was equilibrated for 2 ns using NPT ensemble. Finally, each ternary complex system was subjected to 50 ns production run in the NPT ensemble. A time step of 2 fs was used throughout simulation with periodic boundary conditions. The LINCS algorithm was used to restrain all bonds to the hydrogen atom, permitting a time step of 2 fs. The long-range electrostatic interactions were calculated using the PME algorithm with a cutoff distance 1.2 nm. Structural clustering was performed on the whole trajectory with RMSD cutoff 2.0 Å using g cluster tool implemented in GROMACS. The single representative conformation was extracted from the highest populated cluster of each system. The trajectory was analyzed using VMD and simulation images were generated using Discovery Studio; Dassault Systèmes BIOVIA 2016) (FIGS. 5 and 13A).

Example 14. Construction and Cloning of the Gain-of-Function Mutants of D2M2-4

The construction of D2M2-4 chimera (with DAF-linker) and its biochemical characterization showed that this molecule has both cofactor as well as decay-acceleration activities. Further, although it showed optimum C3b-CFA and C4b-CFA, it demonstrated only partial CP-DAA and diminished AP-DAA. However, overall, the molecule acted on all the three pathways (AP/CP/LP) and its inhibitory activity was comparable to DAF for LP and AP; it showed ~3.7-fold less inhibitory activity as compared to DAF for the CP. Thus, the D2M2-4 molecule was also a good candidate to generate a molecule with optimum CFA and DAA.

Thus, the optimization of AP-DAA of the D2M2-4 chimera was sought. The tacit assumption here was that the functional sites for CFA and DAA are spatially conserved over the four-CCP structure in a non-overlapping manner. The 13 residues in the D2, M2 and M3 domains of the chimera were substituted. These residues were shown to be critical for the AP-DAA in DAF and other RCA regulators (FIG. 16). To be specific, our mutagenesis studies were guided by the mutagenesis in human regulators as well as viral regulators (FIG. 16C). The generation of single amino acid substitution mutants was achieved by the site-directed mutagenesis approach. The location of 13 substitutions and the basis of mutation is shown in FIG. 16A.

For generating the mutants, the mutation was first introduced in D2M2-4 construct cloned in pGEMT. These mutations were introduced by using a commercially available QUICK-CHANGE™ site-directed mutagenesis kit from Stratagene (same as that utilized for generating D2D3M3M4 mutants). The pGEMT clones having the desired mutations were confirmed by restriction digestion as well as by sequencing. Following validation, all the clones were subcloned in the pET-28b expression vector and re-validated by restriction digestion and sequencing.

Example 15. Expression, Purification and Refolding of D2M2-4 Mutants

The pET clones of gain-of-function mutants of D2M2-4 were transformed into *Escherichia coli* BL21 cells and induced for expression. The mutants expressed were then purified from the inclusion bodies in the denaturing conditions using urea by subjecting to Ni-NTA column chromatography. The purified proteins were refolded by a rapid dilution method and loaded onto gel filtration chromatography to remove aggregates and obtain their mono-disperse population. The purity of all the mutants exceeded 95% as observed from the SDS-PAGE analysis (FIG. 16B). Following the gel filtration of the re-folded mutants, the purified proteins were expected to have mono-dispersed population and to validate the same, analytical runs on the SUPEROSE-12™ gel filtration column (GE Healthcare Life Sciences) were performed. All the proteins displayed a mono-dispersed population on the gel filtration (profiles as shown in FIG. 17).

Example 16 Characterization of Classical Pathway Decay-Accelerating Activity of the D2M2-4 Substitution Mutants The above single amino acid substitution mutants of D2M2-4 were expected to gain the AP-DAA. However, from the previous data, we know that some of the residues which are shown to be important for the AP-DAA in DAF are also important for the CP-DAA. Thus, gain in CP- as well as AP-DAA was expected in some mutants. The CP-DAA of all the 13 D2M2-4 mutants was measured, and 2 mutants (I134A and L161K) showed about 2-fold increase in the activity. The I134A mutation was based on DAF mutation data which showed that mutation of F to A at this position increased its CP-DAA by 183%. On the other hand, the L161K mutation was based on DAF and Kaposica mutation data which revealed that removal of positive charge at this position reduces its CP-DAA (FIG. 18). Apart from these gain-of-function mutants, some mutants which either did not show gain or showed loss in CP-DAA were also present suggesting local environment significantly affect the interactions.

Example 17. Characterization of Alternative Pathway Decay-Accelerating Activity of the D2M2-4 Substitution Mutants As stated earlier, the rationale for designing these mutants was to gain AP-DAA and, therefore, all of the site directed mutants planned above were for the enhancement of the AP-DAA of the D2M2-4 chimera. The AP-DAA of these mutants was evaluated, four of the mutants viz., E136Q (D2), Y101N, I134A and L161K, showed a significant improvement in the AP C3-convertase decay activity (FIG. 19). Thus, the gain-of-function of AP-DAA in the D2M2-4 chimera was achieved. E136Q (D2) and Y101N mutations showed 5.6- and 7.2-fold increase in the AP-DAA as compared to D2M2-4. The E136Q (D2) mutation was created based on DAF as E/Q change in DAF at similar position led to 154% increase in the DAA. The Y101N mutation was made based on mutagenesis data on DAF and CR1 as presence of N at the collinear position in these proteins was shown to be crucial for their AP-DAA. The other two gain in AP-DAA mutations, I134A and L161K, also showed 6.7- and 3.4-fold gain in AP-DAA compared to D2M2-4. These mutations were designed based DAF/Kaposica. Importantly, these mutations also showed gain in CP-DAA. In sum, this exercise resulted in identification of four residues that significantly enhance the AP-DAA of D2M2-4. None of the mutations, however, showed a robust gain that can be compared to the AP-DAA of DAF molecule.

Example 18 Characterization of Real-Time Binding of the D2M2-4 Mutants to the C3 Convertase Subunit C3b and C4b It has been documented earlier that DAF interacts with both the subunits of the C3 convertases, i.e., C3b/C4b and Bb/C2a. Further, it was also suggested that such dual interaction of DAF is important for its ability to decay C3-convertases. The binding of D2M2-4 mutants to C3b/C4b was measured by employing an SPR assay. In this assay, C3b or C4b was immobilized on a streptavidin sensor chip by labelling their free —SH group with biotin. Such labelling oriented them on the chip in their physiological orientation. Next, 1 M of D2M2-4 was flowed and each of its mutants over the chip to measure binding. The binding response was measured as response units (RUs). It was plotted against time (sensogram) and compared. Binding of MCP and DAF to C3b and C4b was low as compared to D2M2-4 mutant indicating that substitution of D2 domain along with its associated linker significantly enhances the binding of MCP to C3b and C4b. Next, when the binding response of the mutants was analyzed, none of the mutants that showed gain in either AP-DAA (E136Q (D2), Y101N, I134A and L161K) or CP-DAA (I134A and L161K) showed any increase in binding to C3b or C4b as compared to D2M2-4 molecule (FIG. 20). It is therefore likely that increase in DAA of these mutants is owing to better binding to the other subunit of the convertase, i.e., Bb/C2a.

Example 19. Optimizing the Activity of D2M2-4 Chimera for AP-DAA

Examination of the AP-DAA of putative gain-of-function mutants identified four D2M2-4 mutants with gain in activity. These mutants were E136Q (D2), Y101N, I134A and L161K. These mutants though showed a gain in activity, their activity was much lower in comparison to that of DAF. Hence, to optimize the AP-DAA of D2M2-4, a tetra-mutant which encompasses all the four mutations in it was constructed. Assessment of AP-DAA of the tetra-mutant showed a robust 12.5-fold increase in activity compared to D2M2-4; its CP-DAA, however, did not show any increase (FIG. 21). Having said the above, the AP-DAA of the tetra-mutant was still 138-fold less as compared to the DAF molecule. The results, therefore, indicate that other residues which are crucial for AP-DAA in DAF molecule are missing in D2M2-4 tetra-mutant.

Without being limited by theory, the present invention suggests that functional sites for DAA and CFA are spatially conserved and are non-overlapping. The present invention also determines if the tetra-mutant retained its CFA. Measurement of its CFA displayed that its C3b-CFA and C4b-CFA are comparable to that of D2M2-4 chimera (FIG. 22). Therefore, it was shown here that both CFA (C3b-CFA and C4b-CFA) and DAA (CP-DAA and AP-DAA) can coexist in a single four CCP molecule. The molecule, however, had optimum C3b-CFA, C4b-CFA and CP-DAA, but not AP-DAA, which was observed in DCP.

It is proposed that the chimeric protein of the present invention may be mutated to increase its potency. The chimeric proteins of the preset invention may be modified further by addition of tags, CCPs or peptide/protein for targeting to complement activation site; modifications to increase its in-vitro and in vivo half-life, modifications for membrane or intracellular targeting.

---

We claim:

1. An engineered chimeric protein for inhibition of complement pathways consisting of domains of Decay-Accelerating Factor (DAF) and membrane cofactor protein (MCP) joined by linkers, wherein domains of DAF are selected from D2, D3 and D4 and domains of MCP are selected from M2, M3 and M4, and wherein the engineered chimeric protein is selected from the group consisting of the proteins set forth in SEQ ID NOs: 4-33.

2. The engineered chimeric protein of claim 1, wherein the engineered chimeric protein is the protein set forth in SEQ ID NO: 19.

3. A process to obtain the engineered chimeric protein according to claim 1 comprising expressing the engineered chimeric protein according to claim 1 from a bacterial and/or yeast expression vector.

4. A method of treating paroxysmal nocturnal hemoglobinuria (PNH); age-related macular degeneration (AMD); atypical hemolytic uremic syndrome (aHUS); dense deposit disease (DDD); or an autoimmune disease selected from the group consisting of experimental allergic neuritis, type II collagen-induced arthritis, myasthenia gravis, hemolytic anemia, glomerulonephritis, and immune complex-induced vasculitis; adult respiratory distress syndrome; stroke; heart attack; multiple sclerosis; and burn injuries; comprising administering a therapeutically-effective amount of the engineered chimeric protein according to claim 3 to a subject in need thereof, wherein said engineered chimeric protein has dual activity by enhancing affinity towards factor 1 and avidity towards C3b/C4b by inactivating the C3/C5 convertase.

5. A composition consisting of the engineered chimeric protein according to claim 1, along with pharmaceutically acceptable excipients.

6. The composition according to claim 5, wherein the composition is formulated for administration by a route selected from the group consisting of intravenous, oral, intraperitoneal, intradermal, intramuscular, intranasal, subcutaneous, intraspinal, intratracheal and intracranial administration.

7. The composition according to claim 5, wherein the composition has inhibitory activity towards classical pathway (CP), alternative pathway (AP) and lectin pathway (LP).

8. The composition according to claim 5, which is used for treating complement-mediated diseases, autoimmune diseases, and a disorder selected from the group consisting of age-related macular degeneration, rheumatoid arthritis, spinal cord injury, Parkinson's disease, Alzheimer's disease, cancer, and respiratory disorders conferring resistance to human complement-mediated damage, experimental allergic neuritis, type II collagen-induced arthritis, myasthenia gravis, hemolytic anemia, glomerulonephritis, and immune complex-induced vasculitis.

9. The composition according to claim 8, wherein the respiratory disorders are selected from the group consisting of chronic obstructive pulmonary disease (COPD), allergic inflammation, emphysema, bronchitis, bronchiecstasis, cyctic fibrosis, tuberculosis, pneumonia, neonatal respiratory distress syndrome (RDS), adult RDS, rhinitis and sinusitis.

10. A gene therapy vector for protection from the human complement, consisting of a gene encoding an engineered chimeric protein according to claim 1.

\* \* \* \* \*

SEQUENCE LISTING

```
<160> NUMBER OF SEQ ID NOS: 101

<210> SEQ ID NO 1
<211> LENGTH: 252
<212> TYPE: PRT
<213> ORGANISM: Homo sapiens

<400> SEQUENCE: 1

Cys Gly Leu Pro Pro Asp Val Pro Asn Ala Gln Pro Ala Leu Glu Gly
1               5                   10                  15

Arg Thr Ser Phe Pro Glu Asp Thr Val Ile Thr Tyr Lys Cys Glu Glu
                20                  25                  30

Ser Phe Val Lys Ile Pro Gly Glu Lys Asp Ser Val Ile Cys Leu Lys
            35                  40                  45

Gly Ser Gln Trp Ser Asp Ile Glu Glu Phe Cys Asn Arg Ser Cys Glu
        50                  55                  60

Val Pro Thr Arg Leu Asn Ser Ala Ser Leu Lys Gln Pro Tyr Ile Thr
65                  70                  75                  80

Gln Asn Tyr Phe Pro Val Gly Thr Val Val Glu Tyr Glu Cys Arg Pro
                85                  90                  95

Gly Tyr Arg Arg Glu Pro Ser Leu Ser Pro Lys Leu Thr Cys Leu Gln
            100                 105                 110

Asn Leu Lys Trp Ser Thr Ala Val Glu Phe Cys Lys Lys Lys Ser Cys
            115                 120                 125

Pro Asn Pro Gly Glu Ile Arg Asn Gly Gln Ile Asp Val Pro Gly Gly
        130                 135                 140

Ile Leu Phe Gly Ala Thr Ile Ser Phe Ser Cys Asn Thr Gly Tyr Lys
145                 150                 155                 160

Leu Phe Gly Ser Thr Ser Ser Phe Cys Leu Ile Ser Gly Ser Ser Val
                165                 170                 175

Gln Trp Ser Asp Pro Leu Pro Glu Cys Arg Glu Ile Tyr Cys Pro Ala
            180                 185                 190

Pro Pro Gln Ile Asp Asn Gly Ile Ile Gln Gly Glu Arg Asp His Tyr
            195                 200                 205

Gly Tyr Arg Gln Ser Val Thr Tyr Ala Cys Asn Lys Gly Phe Thr Met
        210                 215                 220

Ile Gly Glu His Ser Ile Tyr Cys Thr Val Asn Asn Asp Glu Gly Glu
225                 230                 235                 240

Trp Ser Gly Pro Pro Pro Glu Cys Arg Gly Lys Ser
                245                 250

<210> SEQ ID NO 2
<211> LENGTH: 253
<212> TYPE: PRT
<213> ORGANISM: Homo sapiens

<400> SEQUENCE: 2

Cys Glu Glu Pro Pro Thr Phe Glu Ala Met Glu Leu Ile Gly Lys Pro
1               5                   10                  15
```

-continued

```
Lys Pro Tyr Tyr Glu Ile Gly Glu Arg Val Asp Tyr Lys Cys Lys Lys
        20                  25                  30

Gly Tyr Phe Tyr Ile Pro Pro Leu Ala Thr His Thr Ile Cys Asp Arg
        35                  40                  45

Asn His Thr Trp Leu Pro Val Ser Asp Asp Ala Cys Tyr Arg Glu Thr
    50                  55                  60

Cys Pro Tyr Ile Arg Asp Pro Leu Asn Gly Gln Ala Val Pro Ala Asn
65                  70                  75                  80

Gly Thr Tyr Glu Phe Gly Tyr Gln Met His Phe Ile Cys Asn Glu Gly
                85                  90                  95

Tyr Tyr Leu Ile Gly Glu Glu Ile Leu Tyr Cys Glu Leu Lys Gly Ser
        100                 105                 110

Val Ala Ile Trp Ser Gly Lys Pro Pro Ile Cys Glu Lys Val Leu Cys
        115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
        195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250
```

```
<210> SEQ ID NO 3
<211> LENGTH: 127
<212> TYPE: PRT
<213> ORGANISM: Homo sapiens

<400> SEQUENCE: 3
```

```
Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
        20                  25                  30

Arg Pro Gly Tyr Arg Arg Glu Pro Ser Leu Ser Pro Lys Leu Thr Cys
        35                  40                  45

Leu Gln Asn Leu Lys Trp Ser Thr Ala Val Glu Phe Cys Lys Lys Lys
    50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Leu Ile Ser Gly Ser
        100                 105                 110

Ser Val Gln Trp Ser Asp Pro Leu Pro Glu Cys Arg Glu Ile Tyr
        115                 120                 125
```

```
<210> SEQ ID NO 4
<211> LENGTH: 254
<212> TYPE: PRT
<213> ORGANISM: Homo sapiens

<400> SEQUENCE: 4

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Glu Leu Lys Gly
                100                 105                 110

Ser Val Ala Ile Trp Ser Gly Lys Pro Pro Ile Cys Glu Lys Val Leu
            115                 120                 125

Cys Thr Pro Pro Pro Lys Ile Lys Asn Gly Lys His Thr Phe Ser Glu
            130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
                180                 185                 190

Val Lys Cys Arg Phe Pro Val Val Glu Asn Gly Lys Gln Ile Ser Gly
            195                 200                 205

Phe Gly Lys Lys Phe Tyr Tyr Lys Ala Thr Val Met Phe Glu Cys Asp
        210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250

<210> SEQ ID NO 5
<211> LENGTH: 254
<212> TYPE: PRT
<213> ORGANISM: Homo sapiens

<400> SEQUENCE: 5

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Tyr Arg Glu
        50                  55                  60

Thr Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
```

-continued

```
                    85                90                95

Gly Tyr Tyr Leu Ile Gly Glu Glu Ile Leu Tyr Cys Glu Leu Lys Gly
            100                105                110

Ser Val Ala Ile Trp Ser Gly Lys Pro Pro Ile Cys Glu Lys Val Leu
            115                120                125

Cys Thr Pro Pro Lys Ile Lys Asn Gly Lys His Thr Phe Ser Glu
            130                135                140

Val Glu Val Phe Glu Tyr Leu Asp Ala Val Thr Tyr Ser Cys Asp Pro
145                150                155                160

Ala Pro Gly Pro Asp Pro Phe Ser Leu Ile Gly Glu Ser Thr Ile Tyr
                165                170                175

Cys Gly Asp Asn Ser Val Trp Ser Arg Ala Ala Pro Glu Cys Lys Val
            180                185                190

Val Lys Cys Arg Phe Pro Val Val Glu Asn Gly Lys Gln Ile Ser Gly
            195                200                205

Phe Gly Lys Lys Phe Tyr Tyr Lys Ala Thr Val Met Phe Glu Cys Asp
            210                215                220

Lys Gly Phe Tyr Leu Asp Gly Ser Asp Thr Ile Val Cys Asp Ser Asn
225                230                235                240

Ser Thr Trp Asp Pro Pro Val Pro Lys Cys Leu Lys Val Leu
                245                250
```

<210> SEQ ID NO 6
<211> LENGTH: 253
<212> TYPE: PRT
<213> ORGANISM: Homo sapiens

<400> SEQUENCE: 6

```
Cys Glu Val Pro Thr Arg Leu Asn Ser Ala Ser Leu Lys Gln Pro Tyr
1                5                10                15

Ile Thr Gln Asn Tyr Phe Pro Val Gly Thr Val Val Glu Tyr Glu Cys
                20                25                30

Arg Pro Gly Tyr Arg Arg Glu Pro Ser Leu Ser Pro Lys Leu Thr Cys
            35                40                45

Leu Gln Asn Leu Lys Trp Ser Thr Ala Val Glu Phe Cys Lys Lys Lys
        50                55                60

Ser Cys Pro Asn Pro Gly Glu Ile Arg Asn Gly Gln Ile Asp Val Pro
65                70                75                80

Gly Gly Ile Leu Phe Gly Ala Thr Ile Ser Phe Ser Cys Asn Thr Gly
                85                90                95

Tyr Lys Leu Phe Gly Ser Thr Ser Ser Phe Cys Leu Ile Ser Gly Ser
            100                105                110

Ser Val Gln Trp Ser Asp Pro Leu Pro Glu Cys Arg Glu Ile Tyr Cys
            115                120                125

Thr Pro Pro Pro Lys Ile Lys Asn Gly Lys His Thr Phe Ser Glu Val
            130                135                140

Glu Val Phe Glu Tyr Leu Asp Ala Val Thr Tyr Ser Cys Asp Pro Ala
145                150                155                160

Pro Gly Pro Asp Pro Phe Ser Leu Ile Gly Glu Ser Thr Ile Tyr Cys
                165                170                175

Gly Asp Asn Ser Val Trp Ser Arg Ala Ala Pro Glu Cys Lys Val Val
            180                185                190

Lys Cys Arg Phe Pro Val Val Glu Asn Gly Lys Gln Ile Ser Gly Phe
            195                200                205
```

-continued

```
Gly Lys Lys Phe Tyr Tyr Lys Ala Thr Val Met Phe Glu Cys Asp Lys
    210             215                 220

Gly Phe Tyr Leu Asp Gly Ser Asp Thr Ile Val Cys Asp Ser Asn Ser
225             230                 235                 240

Thr Trp Asp Pro Pro Val Pro Lys Cys Leu Lys Val Leu
            245             250

<210> SEQ ID NO 7
<211> LENGTH: 250
<212> TYPE: PRT
<213> ORGANISM: Homo sapiens

<400> SEQUENCE: 7

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
    50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Leu Ile Ser Gly Ser
            100                 105                 110

Ser Val Gln Trp Ser Asp Pro Leu Pro Glu Cys Arg Glu Ile Tyr Cys
        115                 120                 125

Pro Ala Pro Pro Gln Ile Asp Asn Gly Ile Ile Gln Gly Glu Arg Asp
    130                 135                 140

His Tyr Gly Tyr Arg Gln Ser Val Thr Tyr Ala Cys Asn Lys Gly Phe
145                 150                 155                 160

Thr Met Ile Gly Glu His Ser Ile Tyr Cys Thr Val Asn Asn Asp Glu
                165                 170                 175

Gly Glu Trp Ser Gly Pro Pro Pro Glu Cys Arg Gly Lys Ser Cys Arg
                180                 185                 190

Phe Pro Val Val Glu Asn Gly Lys Gln Ile Ser Gly Phe Gly Lys Lys
            195                 200                 205

Phe Tyr Tyr Lys Ala Thr Val Met Phe Glu Cys Asp Lys Gly Phe Tyr
    210                 215                 220

Leu Asp Gly Ser Asp Thr Ile Val Cys Asp Ser Asn Ser Thr Trp Asp
225                 230                 235                 240

Pro Pro Val Pro Lys Cys Leu Lys Val Leu
            245                 250

<210> SEQ ID NO 8
<211> LENGTH: 253
<212> TYPE: PRT
<213> ORGANISM: Homo sapiens

<400> SEQUENCE: 8

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30
```

```
Arg Pro Gly Tyr Arg Arg Glu Pro Ser Leu Ser Pro Lys Leu Thr Cys
        35              40              45

Leu Gln Asn Leu Lys Trp Ser Thr Ala Val Glu Phe Cys Lys Lys Lys
    50              55              60

Ser Cys Pro Asn Pro Gly Glu Ile Arg Asn Gly Gln Ile Asp Val Pro
65              70              75              80

Gly Gly Ile Leu Phe Gly Ala Thr Ile Ser Phe Ser Cys Asn Glu Gly
            85              90              95

Tyr Lys Leu Phe Gly Ser Thr Ser Ser Phe Cys Leu Ile Ser Gly Ser
            100             105             110

Ser Val Gln Trp Ser Asp Pro Leu Pro Glu Cys Arg Glu Ile Tyr Cys
        115             120             125

Thr Pro Pro Pro Lys Ile Lys Asn Gly Lys His Thr Phe Ser Glu Val
    130             135             140

Glu Val Phe Glu Tyr Leu Asp Ala Val Thr Tyr Ser Cys Asp Pro Ala
145             150             155             160

Pro Gly Pro Asp Pro Phe Ser Leu Ile Gly Glu Ser Thr Ile Tyr Cys
            165             170             175

Gly Asp Asn Ser Val Trp Ser Arg Ala Ala Pro Glu Cys Lys Val Val
            180             185             190

Lys Cys Arg Phe Pro Val Val Glu Asn Gly Lys Gln Ile Ser Gly Phe
        195             200             205

Gly Lys Lys Phe Tyr Tyr Lys Ala Thr Val Met Phe Glu Cys Asp Lys
    210             215             220

Gly Phe Tyr Leu Asp Gly Ser Asp Thr Ile Val Cys Asp Ser Asn Ser
225             230             235             240

Thr Trp Asp Pro Pro Val Pro Lys Cys Leu Lys Val Leu
            245             250
```

<210> SEQ ID NO 9  
<211> LENGTH: 253  
<212> TYPE: PRT  
<213> ORGANISM: Homo sapiens

<400> SEQUENCE: 9

```
Cys Glu Val Pro Thr Arg Leu Asn Ser Ala Ser Leu Lys Gln Pro Tyr
1               5               10              15

Ile Thr Gln Asn Tyr Phe Pro Val Gly Thr Val Val Glu Tyr Glu Cys
            20              25              30

Arg Pro Gly Tyr Arg Arg Glu Pro Ser Leu Ser Pro Lys Leu Thr Cys
        35              40              45

Leu Gln Asn Leu Lys Trp Ser Thr Ala Val Glu Phe Cys Lys Lys Lys
    50              55              60

Ser Cys Pro Asn Pro Gly Glu Ile Arg Asn Gly Gln Ile Asp Val Pro
65              70              75              80

Gly Gly Ile Leu Phe Gly Ala Thr Ile Ser Phe Ser Cys Asn Thr Gly
            85              90              95

Tyr Tyr Leu Phe Gly Ser Thr Ser Ser Phe Cys Leu Ile Ser Gly Ser
            100             105             110

Ser Val Gln Trp Ser Asp Pro Leu Pro Glu Cys Arg Glu Ile Tyr Cys
        115             120             125

Thr Pro Pro Pro Lys Ile Lys Asn Gly Lys His Thr Phe Ser Glu Val
    130             135             140

Glu Val Phe Glu Tyr Leu Asp Ala Val Thr Tyr Ser Cys Asp Pro Ala
145             150             155             160
```

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
                195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 10
<211> LENGTH: 253
<212> TYPE: PRT
<213> ORGANISM: Homo sapiens

<400> SEQUENCE: 10

Cys Glu Val Pro Thr Arg Leu Asn Ser Ala Ser Leu Lys Gln Pro Tyr
1                 5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Ile Gly Ser Thr Ser Ser Phe Cys Leu Ile Ser Gly Ser
                100                 105                 110

Ser Val Gln Trp Ser Asp Pro Leu Pro Glu Cys Arg Glu Ile Tyr Cys
                115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
                195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 11
<211> LENGTH: 253
<212> TYPE: PRT

```
<213> ORGANISM: Homo sapiens

<400> SEQUENCE: 11

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Lys Thr Ser Ser Phe Cys Leu Ile Ser Gly Ser
                100                 105                 110

Ser Val Gln Trp Ser Asp Pro Leu Pro Glu Cys Arg Glu Ile Tyr Cys
                115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
                195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 12
<211> LENGTH: 253
<212> TYPE: PRT
<213> ORGANISM: Homo sapiens

<400> SEQUENCE: 12

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Tyr Ser Ser Phe Cys Leu Ile Ser Gly Ser
```

-continued

```
                    100                 105                 110

Ser Val Gln Trp Ser Asp Pro Leu Pro Glu Cys Arg Glu Ile Tyr Cys
            115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
            195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 13
<211> LENGTH: 253
<212> TYPE: PRT
<213> ORGANISM: Homo sapiens

<400> SEQUENCE: 13

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
        35                  40                  45

Leu Gln Asn Leu Lys Trp Ser Thr Ala Val Glu Phe Cys Lys Lys Lys
    50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Lys Ile Ser Gly Ser
            100                 105                 110

Ser Val Gln Trp Ser Asp Pro Leu Pro Glu Cys Arg Glu Ile Tyr Cys
            115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
            195                 200                 205

Gly Lys Lys Phe Tyr Tyr Lys Ala Thr Val Met Phe Glu Cys Asp Lys
        210                 215                 220
```

```
Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 14
<211> LENGTH: 253
<212> TYPE: PRT
<213> ORGANISM: Homo sapiens

<400> SEQUENCE: 14

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Leu Ile Ser Gly Ser
                100                 105                 110

Ser Val Gln Trp Ser Asp Lys Leu Pro Glu Cys Arg Glu Ile Tyr Cys
                115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
        195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 15
<211> LENGTH: 253
<212> TYPE: PRT
<213> ORGANISM: Homo sapiens

<400> SEQUENCE: 15

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45
```

-continued

```
Leu Gln Asn Leu Lys Trp Ser Thr Ala Val Glu Phe Cys Lys Lys Lys
    50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Leu Ile Ser Gly Ser
                100                 105                 110

Ser Val Gln Trp Ser Asp Pro Leu Pro Ile Cys Glu Lys Val Leu Cys
                115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
                195                 200                 205

Gly Lys Lys Phe Tyr Tyr Lys Ala Thr Val Met Phe Glu Cys Asp Lys
    210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250
```

```
<210> SEQ ID NO 16
<211> LENGTH: 253
<212> TYPE: PRT
<213> ORGANISM: Homo sapiens

<400> SEQUENCE: 16
```

```
Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45

Leu Gln Asn Leu Lys Trp Ser Thr Ala Val Glu Phe Cys Lys Lys Lys
    50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Phe Gly Ser Thr Ser Ser Phe Cys Leu Ile Ser Gly Ser
                100                 105                 110

Ser Val Gln Trp Ser Pro Lys Ala Pro Glu Cys Arg Glu Ile Tyr Cys
                115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175
```

```
Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
            195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 17
<211> LENGTH: 253
<212> TYPE: PRT
<213> ORGANISM: Homo sapiens

<400> SEQUENCE: 17

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
            85                  90                  95

Tyr Lys Leu Phe Gly Lys Thr Ser Ser Phe Cys Leu Ile Ser Gly Ser
            100                 105                 110

Ser Val Gln Trp Ser Asp Pro Leu Pro Ile Cys Glu Lys Val Leu Cys
        115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
            195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 18
<211> LENGTH: 253
<212> TYPE: PRT
<213> ORGANISM: Homo sapiens

<400> SEQUENCE: 18
```

-continued

```
Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Ile Gly Lys Thr Ser Ser Phe Cys Leu Ile Ser Gly Ser
            100                 105                 110

Ser Val Gln Trp Ser Asp Lys Leu Pro Ile Cys Glu Lys Val Leu Cys
            115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
            195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250
```

<210> SEQ ID NO 19
<211> LENGTH: 253
<212> TYPE: PRT
<213> ORGANISM: Homo sapiens

<400> SEQUENCE: 19

```
Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Pro Gly Glu Ile Arg Asn Gly Gln Ile Asp Val Pro
65                  70                  75                  80

Gly Gly Ile Leu Phe Gly Ala Thr Ile Ser Phe Ser Cys Asn Thr Gly
                85                  90                  95

Tyr Lys Leu Ile Gly Ser Thr Ser Ser Phe Cys Leu Ile Ser Gly Ser
            100                 105                 110

Ser Val Gln Trp Ser Asp Lys Leu Pro Ile Cys Glu Lys Val Leu Cys
```

```
            115                 120                 125

Thr Pro Pro Pro Lys Ile Lys Asn Gly Lys His Thr Phe Ser Glu Val
        130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
                180                 185                 190

Lys Cys Arg Phe Pro Val Val Glu Asn Gly Lys Gln Ile Ser Gly Phe
                195                 200                 205

Gly Lys Lys Phe Tyr Tyr Lys Ala Thr Val Met Phe Glu Cys Asp Lys
        210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu
                245                 250

<210> SEQ ID NO 20
<211> LENGTH: 254
<212> TYPE: PRT
<213> ORGANISM: Homo sapiens

<400> SEQUENCE: 20

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Gln Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Glu Leu Lys Gly
                100                 105                 110

Ser Val Ala Ile Trp Ser Gly Lys Pro Pro Ile Cys Glu Lys Val Leu
            115                 120                 125

Cys Thr Pro Pro Pro Lys Ile Lys Asn Gly Lys His Thr Phe Ser Glu
        130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
                180                 185                 190

Val Lys Cys Arg Phe Pro Val Val Glu Asn Gly Lys Gln Ile Ser Gly
                195                 200                 205

Phe Gly Lys Lys Phe Tyr Tyr Lys Ala Thr Val Met Phe Glu Cys Asp
        210                 215                 220

Lys Gly Phe Tyr Leu Asp Gly Ser Asp Thr Ile Val Cys Asp Ser Asn
225                 230                 235                 240
```

```
Ser Thr Trp Asp Pro Pro Val Pro Lys Cys Leu Lys Val Leu
            245             250

<210> SEQ ID NO 21
<211> LENGTH: 254
<212> TYPE: PRT
<213> ORGANISM: Homo sapiens

<400> SEQUENCE: 21

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser Cys Pro Asn Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Glu Leu Lys Gly
            100                 105                 110

Ser Val Ala Ile Trp Ser Gly Lys Pro Pro Ile Cys Glu Lys Val Leu
            115                 120                 125

Cys Thr Pro Pro Pro Lys Ile Lys Asn Gly Lys His Thr Phe Ser Glu
        130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
                180                 185                 190

Val Lys Cys Arg Phe Pro Val Val Glu Asn Gly Lys Gln Ile Ser Gly
            195                 200                 205

Phe Gly Lys Lys Phe Tyr Tyr Lys Ala Thr Val Met Phe Glu Cys Asp
        210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
            245             250

<210> SEQ ID NO 22
<211> LENGTH: 254
<212> TYPE: PRT
<213> ORGANISM: Homo sapiens

<400> SEQUENCE: 22

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60
```

```
Ser Cys Pro Tyr Ile Arg Asp Pro Leu Asn Gly Gln Ala Val Pro Ala
65              70              75              80

Asn Gly Thr Tyr Leu Phe Gly Tyr Gln Met His Phe Ile Cys Asn Glu
                85              90              95

Gly Tyr Tyr Leu Ile Gly Glu Glu Ile Leu Tyr Cys Glu Leu Lys Gly
            100             105             110

Ser Val Ala Ile Trp Ser Gly Lys Pro Pro Ile Cys Glu Lys Val Leu
        115             120             125

Cys Thr Pro Pro Pro Lys Ile Lys Asn Gly Lys His Thr Phe Ser Glu
        130             135             140

Val Glu Val Phe Glu Tyr Leu Asp Ala Val Thr Tyr Ser Cys Asp Pro
145             150             155             160

Ala Pro Gly Pro Asp Pro Phe Ser Leu Ile Gly Glu Ser Thr Ile Tyr
                165             170             175

Cys Gly Asp Asn Ser Val Trp Ser Arg Ala Ala Pro Glu Cys Lys Val
                180             185             190

Val Lys Cys Arg Phe Pro Val Val Glu Asn Gly Lys Gln Ile Ser Gly
            195             200             205

Phe Gly Lys Lys Phe Tyr Tyr Lys Ala Thr Val Met Phe Glu Cys Asp
        210             215             220

Lys Gly Phe Tyr Leu Asp Gly Ser Asp Thr Ile Val Cys Asp Ser Asn
225             230             235             240

Ser Thr Trp Asp Pro Pro Val Pro Lys Cys Leu Lys Val Leu
                245             250
```

```
<210> SEQ ID NO 23
<211> LENGTH: 254
<212> TYPE: PRT
<213> ORGANISM: Homo sapiens

<400> SEQUENCE: 23

Cys Glu Val Pro Thr Arg Leu Asn Ser Ala Ser Leu Lys Gln Pro Tyr
1               5               10              15

Ile Thr Gln Asn Tyr Phe Pro Val Gly Thr Val Val Glu Tyr Glu Cys
                20              25              30

Arg Pro Gly Tyr Arg Arg Glu Pro Ser Leu Ser Pro Lys Leu Thr Cys
            35              40              45

Leu Gln Asn Leu Lys Trp Ser Thr Ala Val Glu Phe Cys Lys Lys Lys
        50              55              60

Ser Cys Pro Tyr Ile Arg Asp Pro Leu Asn Gly Gln Ala Val Pro Ala
65              70              75              80

Asn Gly Thr Tyr Glu Phe Gly Tyr Gln Met His Phe Ile Cys Asn Glu
                85              90              95

Gly Tyr Tyr Leu Ala Gly Glu Glu Ile Leu Tyr Cys Glu Leu Lys Gly
            100             105             110

Ser Val Ala Ile Trp Ser Gly Lys Pro Pro Ile Cys Glu Lys Val Leu
        115             120             125

Cys Thr Pro Pro Pro Lys Ile Lys Asn Gly Lys His Thr Phe Ser Glu
        130             135             140

Val Glu Val Phe Glu Tyr Leu Asp Ala Val Thr Tyr Ser Cys Asp Pro
145             150             155             160

Ala Pro Gly Pro Asp Pro Phe Ser Leu Ile Gly Glu Ser Thr Ile Tyr
                165             170             175

Cys Gly Asp Asn Ser Val Trp Ser Arg Ala Ala Pro Glu Cys Lys Val
                180             185             190
```

-continued

```
Val Lys Cys Arg Phe Pro Val Val Glu Asn Gly Lys Gln Ile Ser Gly
        195                 200                 205

Phe Gly Lys Lys Phe Tyr Tyr Lys Ala Thr Val Met Phe Glu Cys Asp
        210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250
```

<210> SEQ ID NO 24
<211> LENGTH: 254
<212> TYPE: PRT
<213> ORGANISM: Homo sapiens

<400> SEQUENCE: 24

```
Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
        35                  40                  45

Leu Gln Asn Leu Lys Trp Ser Thr Ala Val Glu Phe Cys Lys Lys Lys
    50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Lys Glu Ile Leu Tyr Cys Glu Leu Lys Gly
            100                 105                 110

Ser Val Ala Ile Trp Ser Gly Lys Pro Pro Ile Cys Glu Lys Val Leu
        115                 120                 125

Cys Thr Pro Pro Pro Lys Ile Lys Asn Gly Lys His Thr Phe Ser Glu
        130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
            180                 185                 190

Val Lys Cys Arg Phe Pro Val Val Glu Asn Gly Lys Gln Ile Ser Gly
        195                 200                 205

Phe Gly Lys Lys Phe Tyr Tyr Lys Ala Thr Val Met Phe Glu Cys Asp
        210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250
```

<210> SEQ ID NO 25
<211> LENGTH: 254
<212> TYPE: PRT
<213> ORGANISM: Homo sapiens

<400> SEQUENCE: 25

```
Cys Glu Val Pro Thr Arg Leu Asn Ser Ala Ser Leu Lys Gln Pro Tyr
1               5                   10                  15
```

```
Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
            50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Tyr Ile Leu Tyr Cys Glu Leu Lys Gly
            100                 105                 110

Ser Val Ala Ile Trp Ser Gly Lys Pro Pro Ile Cys Glu Lys Val Leu
            115                 120                 125

Cys Thr Pro Pro Pro Lys Ile Lys Asn Gly Lys His Thr Phe Ser Glu
            130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
                180                 185                 190

Val Lys Cys Arg Phe Pro Val Val Glu Asn Gly Lys Gln Ile Ser Gly
            195                 200                 205

Phe Gly Lys Lys Phe Tyr Tyr Lys Ala Thr Val Met Phe Glu Cys Asp
            210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250
```

```
<210> SEQ ID NO 26
<211> LENGTH: 254
<212> TYPE: PRT
<213> ORGANISM: Homo sapiens

<400> SEQUENCE: 26

Cys Glu Val Pro Thr Arg Leu Asn Ser Ala Ser Leu Lys Gln Pro Tyr
1                   5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
            50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Lys Leu Lys Gly
            100                 105                 110

Ser Val Ala Ile Trp Ser Gly Lys Pro Pro Ile Cys Glu Lys Val Leu
            115                 120                 125

Cys Thr Pro Pro Pro Lys Ile Lys Asn Gly Lys His Thr Phe Ser Glu
```

-continued

```
            130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                    165                 170                 175

Cys Gly Asp Asn Ser Val Trp Ser Arg Ala Ala Pro Glu Cys Lys Val
                    180                 185                 190

Val Lys Cys Arg Phe Pro Val Val Glu Asn Gly Lys Gln Ile Ser Gly
                    195                 200                 205

Phe Gly Lys Lys Phe Tyr Tyr Lys Ala Thr Val Met Phe Glu Cys Asp
                    210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                    245                 250

<210> SEQ ID NO 27
<211> LENGTH: 254
<212> TYPE: PRT
<213> ORGANISM: Homo sapiens

<400> SEQUENCE: 27

Cys Glu Val Pro Thr Arg Leu Asn Ser Ala Ser Leu Lys Gln Pro Tyr
1                   5                   10                  15

Ile Thr Gln Asn Tyr Phe Pro Val Gly Thr Val Val Glu Tyr Glu Cys
                    20                  25                  30

Arg Pro Gly Tyr Arg Arg Glu Pro Ser Leu Ser Pro Lys Leu Thr Cys
                    35                  40                  45

Leu Gln Asn Leu Lys Trp Ser Thr Ala Val Glu Phe Cys Lys Lys Lys
                    50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                    85                  90                  95

Gly Tyr Tyr Leu Ile Gly Glu Glu Ile Leu Tyr Cys Glu Leu Lys Asp
                    100                 105                 110

Ser Val Ala Ile Trp Ser Asp Lys Pro Pro Ile Cys Glu Lys Val Leu
                    115                 120                 125

Cys Thr Pro Pro Pro Lys Ile Lys Asn Gly Lys His Thr Phe Ser Glu
                    130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                    165                 170                 175

Cys Gly Asp Asn Ser Val Trp Ser Arg Ala Ala Pro Glu Cys Lys Val
                    180                 185                 190

Val Lys Cys Arg Phe Pro Val Val Glu Asn Gly Lys Gln Ile Ser Gly
                    195                 200                 205

Phe Gly Lys Lys Phe Tyr Tyr Lys Ala Thr Val Met Phe Glu Cys Asp
                    210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                    245                 250
```

-continued

```
<210> SEQ ID NO 28
<211> LENGTH: 254
<212> TYPE: PRT
<213> ORGANISM: Homo sapiens

<400> SEQUENCE: 28

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45

Leu Gln Asn Leu Lys Trp Ser Thr Ala Val Glu Phe Cys Lys Lys Lys
            50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                    85                  90                  95

Gly Tyr Tyr Leu Ile Gly Glu Glu Ile Leu Tyr Cys Glu Leu Lys Gly
                100                 105                 110

Ser Val Ala Ile Trp Ser Gly Lys Pro Pro Ile Cys Glu Lys Val Lys
                115                 120                 125

Cys Thr Pro Pro Pro Lys Ile Lys Asn Gly Lys His Thr Phe Ser Glu
            130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                    165                 170                 175

Cys Gly Asp Asn Ser Val Trp Ser Arg Ala Ala Pro Glu Cys Lys Val
                180                 185                 190

Val Lys Cys Arg Phe Pro Val Val Glu Asn Gly Lys Gln Ile Ser Gly
                195                 200                 205

Phe Gly Lys Lys Phe Tyr Tyr Lys Ala Thr Val Met Phe Glu Cys Asp
            210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250

<210> SEQ ID NO 29
<211> LENGTH: 254
<212> TYPE: PRT
<213> ORGANISM: Homo sapiens

<400> SEQUENCE: 29

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
                35                  40                  45

Leu Gln Asn Leu Lys Trp Ser Thr Ala Val Glu Phe Cys Lys Lys Lys
            50                  55                  60

Ser Cys Pro Tyr Ile Arg Asp Pro Leu Asn Gly Gln Ala Val Pro Ala
65                  70                  75                  80
```

```
Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Glu Leu Lys Gly
               100                 105                 110

Ser Val Ala Ile Trp Ser Gly Lys Pro Pro Ile Cys Glu Lys Val Leu
               115                 120                 125

Cys Ala Pro Pro Lys Ile Lys Asn Gly Lys His Thr Phe Ser Glu
           130                 135                 140

Val Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
               180                 185                 190

Val Lys Cys Arg Phe Pro Val Val Glu Asn Gly Lys Gln Ile Ser Gly
               195                 200                 205

Phe Gly Lys Lys Phe Tyr Tyr Lys Ala Thr Val Met Phe Glu Cys Asp
           210                 215                 220

Lys Gly Phe Tyr Leu Asp Gly Ser Asp Thr Ile Val Cys Asp Ser Asn
225                 230                 235                 240

Ser Thr Trp Asp Pro Pro Val Pro Lys Cys Leu Lys Val Leu
                245                 250

<210> SEQ ID NO 30
<211> LENGTH: 254
<212> TYPE: PRT
<213> ORGANISM: Homo sapiens

<400> SEQUENCE: 30

Cys Glu Val Pro Thr Arg Leu Asn Ser Ala Ser Leu Lys Gln Pro Tyr
1                 5                   10                  15

Ile Thr Gln Asn Tyr Phe Pro Val Gly Thr Val Val Glu Tyr Glu Cys
                20                  25                  30

Arg Pro Gly Tyr Arg Arg Glu Pro Ser Leu Ser Pro Lys Leu Thr Cys
           35                  40                  45

Leu Gln Asn Leu Lys Trp Ser Thr Ala Val Glu Phe Cys Lys Lys Lys
       50                  55                  60

Ser Cys Pro Tyr Ile Arg Asp Pro Leu Asn Gly Gln Ala Val Pro Ala
65                  70                  75                  80

Asn Gly Thr Tyr Glu Phe Gly Tyr Gln Met His Phe Ile Cys Asn Glu
                85                  90                  95

Gly Tyr Tyr Leu Ile Gly Glu Glu Ile Leu Tyr Cys Glu Leu Lys Gly
               100                 105                 110

Ser Val Ala Ile Trp Ser Gly Lys Pro Pro Ile Cys Glu Lys Val Leu
               115                 120                 125

Cys Thr Pro Pro Pro Lys Ile Lys Asn Gly Lys His Thr Phe Ser Glu
           130                 135                 140

Arg Glu Val Phe Glu Tyr Leu Asp Ala Val Thr Tyr Ser Cys Asp Pro
145                 150                 155                 160

Ala Pro Gly Pro Asp Pro Phe Ser Leu Ile Gly Glu Ser Thr Ile Tyr
                165                 170                 175

Cys Gly Asp Asn Ser Val Trp Ser Arg Ala Ala Pro Glu Cys Lys Val
               180                 185                 190

Val Lys Cys Arg Phe Pro Val Val Glu Asn Gly Lys Gln Ile Ser Gly
               195                 200                 205
```

-continued

```
Phe Gly Lys Lys Phe Tyr Tyr Lys Ala Thr Val Met Phe Glu Cys Asp
    210             215             220

Lys Gly Phe Tyr Leu Asp Gly Ser Asp Thr Ile Val Cys Asp Ser Asn
225             230             235             240

Ser Thr Trp Asp Pro Pro Val Pro Lys Cys Leu Lys Val Leu
            245             250
```

<210> SEQ ID NO 31
<211> LENGTH: 254
<212> TYPE: PRT
<213> ORGANISM: Homo sapiens

<400> SEQUENCE: 31

```
Cys Glu Val Pro Thr Arg Leu Asn Ser Ala Ser Leu Lys Gln Pro Tyr
1               5               10              15

Ile Thr Gln Asn Tyr Phe Pro Val Gly Thr Val Val Glu Tyr Glu Cys
            20              25              30

Arg Pro Gly Tyr Arg Arg Glu Pro Ser Leu Ser Pro Lys Leu Thr Cys
        35              40              45

Leu Gln Asn Leu Lys Trp Ser Thr Ala Val Glu Phe Cys Lys Lys Lys
    50              55              60

Ser Cys Pro Tyr Ile Arg Asp Pro Leu Asn Gly Gln Ala Val Pro Ala
65              70              75              80

Asn Gly Thr Tyr Glu Phe Gly Tyr Gln Met His Phe Ile Cys Asn Glu
            85              90              95

Gly Tyr Tyr Leu Ile Gly Glu Glu Ile Leu Tyr Cys Glu Leu Lys Gly
            100             105             110

Ser Val Ala Ile Trp Ser Gly Lys Pro Pro Ile Cys Glu Lys Val Leu
        115             120             125

Cys Thr Pro Pro Pro Lys Ile Lys Asn Gly Lys His Thr Phe Ser Glu
    130             135             140

Val Glu Phe Phe Glu Tyr Leu Asp Ala Val Thr Tyr Ser Cys Asp Pro
145             150             155             160

Ala Pro Gly Pro Asp Pro Phe Ser Leu Ile Gly Glu Ser Thr Ile Tyr
            165             170             175

Cys Gly Asp Asn Ser Val Trp Ser Arg Ala Ala Pro Glu Cys Lys Val
            180             185             190

Val Lys Cys Arg Phe Pro Val Val Glu Asn Gly Lys Gln Ile Ser Gly
        195             200             205

Phe Gly Lys Lys Phe Tyr Tyr Lys Ala Thr Val Met Phe Glu Cys Asp
    210             215             220

Lys Gly Phe Tyr Leu Asp Gly Ser Asp Thr Ile Val Cys Asp Ser Asn
225             230             235             240

Ser Thr Trp Asp Pro Pro Val Pro Lys Cys Leu Lys Val Leu
            245             250
```

<210> SEQ ID NO 32
<211> LENGTH: 254
<212> TYPE: PRT
<213> ORGANISM: Homo sapiens

<400> SEQUENCE: 32

```
Cys Glu Val Pro Thr Arg Leu Asn Ser Ala Ser Leu Lys Gln Pro Tyr
1               5               10              15

Ile Thr Gln Asn Tyr Phe Pro Val Gly Thr Val Val Glu Tyr Glu Cys
            20              25              30
```

```
Arg Pro Gly Tyr Arg Arg Glu Pro Ser Leu Ser Pro Lys Leu Thr Cys
        35              40              45
Leu Gln Asn Leu Lys Trp Ser Thr Ala Val Glu Phe Cys Lys Lys Lys
    50              55              60
Ser Cys Pro Tyr Ile Arg Asp Pro Leu Asn Gly Gln Ala Val Pro Ala
65              70              75              80
Asn Gly Thr Tyr Glu Phe Gly Tyr Gln Met His Phe Ile Cys Asn Glu
                85              90              95
Gly Tyr Tyr Leu Ile Gly Glu Glu Ile Leu Tyr Cys Glu Leu Lys Gly
                100             105             110
Ser Val Ala Ile Trp Ser Gly Lys Pro Pro Ile Cys Glu Lys Val Leu
                115             120             125
Cys Thr Pro Pro Pro Lys Ile Lys Asn Gly Lys His Thr Phe Ser Glu
        130             135             140
Val Glu Val Phe Glu Tyr Arg Asp Ala Val Thr Tyr Ser Cys Asp Pro
145             150             155             160
Ala Pro Gly Pro Asp Pro Phe Ser Leu Ile Gly Glu Ser Thr Ile Tyr
                165             170             175
Cys Gly Asp Asn Ser Val Trp Ser Arg Ala Ala Pro Glu Cys Lys Val
                180             185             190
Val Lys Cys Arg Phe Pro Val Val Glu Asn Gly Lys Gln Ile Ser Gly
        195             200             205
Phe Gly Lys Lys Phe Tyr Tyr Lys Ala Thr Val Met Phe Glu Cys Asp
        210             215             220
Lys Gly Phe Tyr Leu Asp Gly Ser Asp Thr Ile Val Cys Asp Ser Asn
225             230             235             240
Ser Thr Trp Asp Pro Pro Val Pro Lys Cys Leu Lys Val Leu
                245             250

<210> SEQ ID NO 33
<211> LENGTH: 254
<212> TYPE: PRT
<213> ORGANISM: Homo sapiens

<400> SEQUENCE: 33

Cys Glu Val Pro Thr Arg Leu Asn Ser Ala Ser Leu Lys Gln Pro Tyr
1               5               10              15
Ile Thr Gln Asn Tyr Phe Pro Val Gly Thr Val Val Glu Tyr Glu Cys
                20              25              30
Arg Pro Gly Tyr Arg Arg Gln Pro Ser Leu Ser Pro Lys Leu Thr Cys
        35              40              45
Leu Gln Asn Leu Lys Trp Ser Thr Ala Val Glu Phe Cys Lys Lys Lys
    50              55              60
Ser Cys Pro Asn Ile Arg Asp Pro Leu Asn Gly Gln Ala Val Pro Ala
65              70              75              80
Asn Gly Thr Tyr Glu Phe Gly Tyr Gln Met His Phe Ile Cys Asn Glu
                85              90              95
Gly Tyr Tyr Leu Ala Gly Glu Glu Ile Leu Tyr Cys Glu Leu Lys Gly
                100             105             110
Ser Val Ala Ile Trp Ser Gly Lys Pro Pro Ile Cys Glu Lys Val Lys
                115             120             125
Cys Thr Pro Pro Pro Lys Ile Lys Asn Gly Lys His Thr Phe Ser Glu
        130             135             140
Val Glu Val Phe Glu Tyr Leu Asp Ala Val Thr Tyr Ser Cys Asp Pro
```

-continued

```
145              150              155              160

Ala Pro Gly Pro Asp Pro Phe Ser Leu Ile Gly Glu Ser Thr Ile Tyr
             165              170              175

Cys Gly Asp Asn Ser Val Trp Ser Arg Ala Ala Pro Glu Cys Lys Val
         180              185              190

Val Lys Cys Arg Phe Pro Val Val Glu Asn Gly Lys Gln Ile Ser Gly
         195              200              205

Phe Gly Lys Lys Phe Tyr Tyr Lys Ala Thr Val Met Phe Glu Cys Asp
     210              215              220

Lys Gly Phe Tyr Leu Asp Gly Ser Asp Thr Ile Val Cys Asp Ser Asn
225              230              235              240

Ser Thr Trp Asp Pro Pro Val Pro Lys Cys Leu Lys Val Leu
             245              250
```

```
<210> SEQ ID NO 34
<211> LENGTH: 29
<212> TYPE: DNA
<213> ORGANISM: Artificial Sequence
<220> FEATURE:
<223> OTHER INFORMATION: Chemically-synthesized primer

<400> SEQUENCE: 34
ggaattcgac tgtggccttc ccccagatg                                      29

<210> SEQ ID NO 35
<211> LENGTH: 32
<212> TYPE: DNA
<213> ORGANISM: Artificial Sequence
<220> FEATURE:
<223> OTHER INFORMATION: Chemically-synthesized primer

<400> SEQUENCE: 35
gctctagatt atctgcattc aggtggtggg cc                                  32

<210> SEQ ID NO 36
<211> LENGTH: 35
<212> TYPE: DNA
<213> ORGANISM: Artificial Sequence
<220> FEATURE:
<223> OTHER INFORMATION: Chemically-synthesized primer

<400> SEQUENCE: 36
ggaattccat atggactgtg gccttccccc agatg                               35

<210> SEQ ID NO 37
<211> LENGTH: 32
<212> TYPE: DNA
<213> ORGANISM: Artificial Sequence
<220> FEATURE:
<223> OTHER INFORMATION: Chemically-synthesized primer

<400> SEQUENCE: 37
ccgctcgagt ctgcattcag gtggtgggcc ac                                  32

<210> SEQ ID NO 38
<211> LENGTH: 27
<212> TYPE: DNA
<213> ORGANISM: Artificial Sequence
<220> FEATURE:
<223> OTHER INFORMATION: Chemically-synthesized primer

<400> SEQUENCE: 38
ggaattcgcc tgtgaggagc caccaac                                        27
```

-continued

```
<210> SEQ ID NO 39
<211> LENGTH: 32
<212> TYPE: DNA
<213> ORGANISM: Artificial Sequence
<220> FEATURE:
<223> OTHER INFORMATION: Chemically-synthesized primer

<400> SEQUENCE: 39
gctctagatt aaagacactt tggaactggg gg                                    32

<210> SEQ ID NO 40
<211> LENGTH: 69
<212> TYPE: DNA
<213> ORGANISM: Artificial Sequence
<220> FEATURE:
<223> OTHER INFORMATION: Chemically-synthesized primer

<400> SEQUENCE: 40
catgccatgg gcaagtgtga ggagccacca acatttgaag ctatggagct cattggtaaa      60
ccaaaaccc                                                              69

<210> SEQ ID NO 41
<211> LENGTH: 28
<212> TYPE: DNA
<213> ORGANISM: Artificial Sequence
<220> FEATURE:
<223> OTHER INFORMATION: Chemically-synthesized primer

<400> SEQUENCE: 41
cgcaagctta agacactttg gaactggg                                         28

<210> SEQ ID NO 42
<211> LENGTH: 35
<212> TYPE: DNA
<213> ORGANISM: Artificial Sequence
<220> FEATURE:
<223> OTHER INFORMATION: Chemically-synthesized primer

<400> SEQUENCE: 42
cccaagcttt gcgaggtgcc aacaaggcta aattc                                 35

<210> SEQ ID NO 43
<211> LENGTH: 36
<212> TYPE: DNA
<213> ORGANISM: Artificial Sequence
<220> FEATURE:
<223> OTHER INFORMATION: Chemically-synthesized primer

<400> SEQUENCE: 43
ccgctcgaga taaatttctc tgcactctgg caacgg                                36

<210> SEQ ID NO 44
<211> LENGTH: 26
<212> TYPE: DNA
<213> ORGANISM: Artificial Sequence
<220> FEATURE:
<223> OTHER INFORMATION: Chemically-synthesized primer

<400> SEQUENCE: 44
ggaattctgc gaggtgccaa caaggc                                           26

<210> SEQ ID NO 45
<211> LENGTH: 42
<212> TYPE: DNA
```

-continued

<213> ORGANISM: Artificial Sequence
<220> FEATURE:
<223> OTHER INFORMATION: Chemically-synthesized primer

<400> SEQUENCE: 45
cccgtatata tggacatgat ttcttttac aaaattcgac tg                           42

<210> SEQ ID NO 46
<211> LENGTH: 51
<212> TYPE: DNA
<213> ORGANISM: Artificial Sequence
<220> FEATURE:
<223> OTHER INFORMATION: Chemically-synthesized primer

<400> SEQUENCE: 46
cgaattttgt aaaagaaat catgtccata tatacgggat cctttaaatg g                 51

<210> SEQ ID NO 47
<211> LENGTH: 31
<212> TYPE: DNA
<213> ORGANISM: Artificial Sequence
<220> FEATURE:
<223> OTHER INFORMATION: Chemically-synthesized primer

<400> SEQUENCE: 47
gctctagagc aagacacttt ggaactgggg g                                      31

<210> SEQ ID NO 48
<211> LENGTH: 26
<212> TYPE: DNA
<213> ORGANISM: Artificial Sequence
<220> FEATURE:
<223> OTHER INFORMATION: Chemically-synthesized primer

<400> SEQUENCE: 48
ggaattctgc gaggtgccaa caaggc                                            26

<210> SEQ ID NO 49
<211> LENGTH: 40
<212> TYPE: DNA
<213> ORGANISM: Artificial Sequence
<220> FEATURE:
<223> OTHER INFORMATION: Chemically-synthesized primer

<400> SEQUENCE: 49
ggacatgttt ctctataaca aaattcgact gctgtggacc                             40

<210> SEQ ID NO 50
<211> LENGTH: 43
<212> TYPE: DNA
<213> ORGANISM: Artificial Sequence
<220> FEATURE:
<223> OTHER INFORMATION: Chemically-synthesized primer

<400> SEQUENCE: 50
cagcagtcga attttgttat agagaaacat gtccatatat acg                         43

<210> SEQ ID NO 51
<211> LENGTH: 31
<212> TYPE: DNA
<213> ORGANISM: Artificial Sequence
<220> FEATURE:
<223> OTHER INFORMATION: Chemically-synthesized primer

<400> SEQUENCE: 51
gctctagagc aagacacttt ggaactgggg g                                      31

-continued

```
<210> SEQ ID NO 52
<211> LENGTH: 30
<212> TYPE: DNA
<213> ORGANISM: Artificial Sequence
<220> FEATURE:
<223> OTHER INFORMATION: Chemically-synthesized primer

<400> SEQUENCE: 52
catgccatgg gctgcgaggt cccaacaagg                                    30

<210> SEQ ID NO 53
<211> LENGTH: 36
<212> TYPE: DNA
<213> ORGANISM: Artificial Sequence
<220> FEATURE:
<223> OTHER INFORMATION: Chemically-synthesized primer

<400> SEQUENCE: 53
ggaggtggtg tacaataaat ttctctgcac tctggc                            36

<210> SEQ ID NO 54
<211> LENGTH: 45
<212> TYPE: DNA
<213> ORGANISM: Artificial Sequence
<220> FEATURE:
<223> OTHER INFORMATION: Chemically-synthesized primer

<400> SEQUENCE: 54
gtgcagagaa atttattgta caccacctcc aaaaataaaa aatgg                  45

<210> SEQ ID NO 55
<211> LENGTH: 28
<212> TYPE: DNA
<213> ORGANISM: Artificial Sequence
<220> FEATURE:
<223> OTHER INFORMATION: Chemically-synthesized primer

<400> SEQUENCE: 55
cgcaagctta agacactttg gaactggg                                     28

<210> SEQ ID NO 56
<211> LENGTH: 30
<212> TYPE: DNA
<213> ORGANISM: Artificial Sequence
<220> FEATURE:
<223> OTHER INFORMATION: Chemically-synthesized primer

<400> SEQUENCE: 56
catgccatgg gctgcgaggt cccaacaagg                                    30

<210> SEQ ID NO 57
<211> LENGTH: 36
<212> TYPE: DNA
<213> ORGANISM: Artificial Sequence
<220> FEATURE:
<223> OTHER INFORMATION: Chemically-synthesized primer

<400> SEQUENCE: 57
gacatttgac cactttgcat tcaggtggtg ggccac                            36

<210> SEQ ID NO 58
<211> LENGTH: 38
<212> TYPE: DNA
<213> ORGANISM: Artificial Sequence
<220> FEATURE:
```

<223> OTHER INFORMATION: Chemically-synthesized primer

<400> SEQUENCE: 58
ggaccacctg aatgcaaagt ggtcaaatgt cgatttcc                              38

<210> SEQ ID NO 59
<211> LENGTH: 28
<212> TYPE: DNA
<213> ORGANISM: Artificial Sequence
<220> FEATURE:
<223> OTHER INFORMATION: Chemically-synthesized primer

<400> SEQUENCE: 59
cgcaagctta agacactttg gaactggg                                        28

<210> SEQ ID NO 60
<211> LENGTH: 38
<212> TYPE: DNA
<213> ORGANISM: Artificial Sequence
<220> FEATURE:
<223> OTHER INFORMATION: Chemically-synthesized primer

<400> SEQUENCE: 60
catgcatcat ctcaggtaac actgtcattt gggataat                             38

<210> SEQ ID NO 61
<211> LENGTH: 39
<212> TYPE: DNA
<213> ORGANISM: Artificial Sequence
<220> FEATURE:
<223> OTHER INFORMATION: Chemically-synthesized primer

<400> SEQUENCE: 61
attatcccaa atgcacagtg ttacctgaga tgatgcatg                            39

<210> SEQ ID NO 62
<211> LENGTH: 37
<212> TYPE: DNA
<213> ORGANISM: Artificial Sequence
<220> FEATURE:
<223> OTHER INFORMATION: Chemically-synthesized primer

<400> SEQUENCE: 62
ctgtcatttg ggataataaa acacctattt gtgacag                              37

<210> SEQ ID NO 63
<211> LENGTH: 36
<212> TYPE: DNA
<213> ORGANISM: Artificial Sequence
<220> FEATURE:
<223> OTHER INFORMATION: Chemically-synthesized primer

<400> SEQUENCE: 63
ctgcacaaat aggtgtttta ttatcccaaa tgacag                               36

<210> SEQ ID NO 64
<211> LENGTH: 65
<212> TYPE: PRT
<213> ORGANISM: Artificial Sequence
<220> FEATURE:
<223> OTHER INFORMATION: Chemically-synthesized amino acid sequence

<400> SEQUENCE: 64

Cys Glu Val Pro Thr Arg Leu Asn Ser Ala Ser Leu Lys Gln Pro Tyr
1               5                   10                  15

-continued

```
Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
    50                  55                  60

Ser
65

<210> SEQ ID NO 65
<211> LENGTH: 63
<212> TYPE: PRT
<213> ORGANISM: Artificial Sequence
<220> FEATURE:
<223> OTHER INFORMATION: Chemically-synthesized amino acid sequence

<400> SEQUENCE: 65

Cys Pro Tyr Ile Arg Asp Pro Leu Asn Gly Gln Ala Val Pro Ala Asn
1               5                   10                  15

Gly Thr Tyr Glu Phe Gly Tyr Gln Met His Phe Ile Cys Asn Glu Gly
            20                  25                  30

Tyr Tyr Leu Ile Gly Glu Glu Ile Leu Tyr Cys Glu Leu Lys Gly Ser
            35                  40                  45

Val Ala Ile Trp Ser Gly Lys Pro Pro Ile Cys Glu Lys Val Leu
    50                  55                  60

<210> SEQ ID NO 66
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 66

Cys Thr Pro Pro Pro Lys Ile Lys Asn Gly Lys His Thr Phe Ser Glu
1               5                   10                  15

Val Glu Val Phe Glu Tyr Leu Asp Ala Val Thr Tyr Ser Cys Asp Pro
            20                  25                  30

Ala Pro Gly Pro Asp Pro Phe Ser Leu Ile Gly Glu Ser Thr Ile Tyr
            35                  40                  45

Cys Gly Asp Asn Ser Val Trp Ser Arg Ala Ala Pro Glu Cys
    50                  55                  60

<210> SEQ ID NO 67
<211> LENGTH: 60
<212> TYPE: PRT
<213> ORGANISM: Artificial Sequence
<220> FEATURE:
<223> OTHER INFORMATION: Chemically-synthesized amino acid sequence

<400> SEQUENCE: 67

Cys Arg Phe Pro Val Val Glu Asn Gly Lys Gln Ile Ser Gly Phe Gly
1               5                   10                  15

Lys Lys Phe Tyr Tyr Lys Ala Thr Asx Met Phe Glu Cys Asp Lys Gly
            20                  25                  30

Phe Tyr Leu Asp Gly Ser Asp Thr Ile Val Cys Asp Ser Asn Ser Thr
            35                  40                  45

Trp Asp Pro Pro Val Pro Lys Cys Leu Lys Val Leu
    50                  55                  60
```

-continued

```
<210> SEQ ID NO 68
<211> LENGTH: 66
<212> TYPE: PRT
<213> ORGANISM: Artificial Sequence
<220> FEATURE:
<223> OTHER INFORMATION: Chemically-synthesized amino acid sequence

<400> SEQUENCE: 68

Ser Cys Glu Val Pro Thr Arg Leu Asn Ser Ala Ser Leu Lys Gln Pro
1               5                   10                  15

Tyr Ile Thr Gln Asn Tyr Phe Pro Val Gly Thr Val Val Glu Tyr Glu
            20                  25                  30

Cys Arg Pro Gly Tyr Arg Arg Glu Pro Ser Leu Ser Pro Lys Leu Thr
        35                  40                  45

Cys Leu Gln Asn Leu Lys Trp Ser Thr Ala Val Glu Phe Cys Lys Lys
    50                  55                  60

Lys Ser
65

<210> SEQ ID NO 69
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 69

Cys Pro Asn Pro Gly Glu Ile Arg Asn Gly Gln Ile Asp Val Pro Gly
1               5                   10                  15

Gly Ile Leu Phe Gly Ala Thr Ile Ser Phe Ser Cys Asn Thr Gly Tyr
            20                  25                  30

Lys Leu Phe Gly Ser Thr Ser Ser Phe Cys Leu Ile Ser Gly Ser Ser
        35                  40                  45

Val Gln Trp Ser Asp Pro Leu Pro Glu Cys Arg Glu Ile Tyr
    50                  55                  60

<210> SEQ ID NO 70
<211> LENGTH: 65
<212> TYPE: PRT
<213> ORGANISM: Artificial Sequence
<220> FEATURE:
<223> OTHER INFORMATION: Chemically-synthesized amino acid sequence

<400> SEQUENCE: 70

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
        35                  40                  45

Leu Gln Asn Leu Lys Trp Ser Thr Ala Val Glu Phe Cys Lys Lys Lys
    50                  55                  60

Ser
65

<210> SEQ ID NO 71
<211> LENGTH: 65
<212> TYPE: PRT
<213> ORGANISM: Artificial Sequence
<220> FEATURE:
<223> OTHER INFORMATION: Chemically-synthesized amino acid sequence
```

-continued

```
<400> SEQUENCE: 71

Cys Glu Val Pro Thr Arg Leu Asn Ser Ala Ser Leu Lys Gln Pro Tyr
1               5                   10                  15

Ile Thr Gln Asn Tyr Phe Pro Val Gly Thr Val Val Glu Tyr Glu Cys
            20                  25                  30

Arg Pro Gly Tyr Arg Arg Glu Pro Ser Leu Ser Pro Lys Leu Thr Cys
            35                  40                  45

Leu Gln Asn Leu Lys Trp Ser Thr Ala Val Glu Phe Cys Lys Lys Lys
        50                  55                  60

Ser
65

<210> SEQ ID NO 72
<211> LENGTH: 64
<212> TYPE: PRT
<213> ORGANISM: Artificial Sequence
<220> FEATURE:
<223> OTHER INFORMATION: Chemically-synthesized amino acid sequence

<400> SEQUENCE: 72

Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
            20                  25                  30

Gly Tyr Phe Tyr Ile Pro Pro Leu Ala Thr His Thr Ile Cys Asp Arg
            35                  40                  45

Asn His Thr Trp Leu Pro Val Ser Asp Asp Ala Cys Tyr Arg Glu Thr
        50                  55                  60

<210> SEQ ID NO 73
<211> LENGTH: 64
<212> TYPE: PRT
<213> ORGANISM: Artificial Sequence
<220> FEATURE:
<223> OTHER INFORMATION: Chemically-synthesized amino acid sequence

<400> SEQUENCE: 73

Cys Asn Glu Leu Pro Pro Arg Arg Asn Thr Glu Ile Leu Thr Gly Ser
1               5                   10                  15

Trp Ser Asp Gln Thr Tyr Pro Glu Gly Thr Gln Ala Ile Tyr Lys Cys
            20                  25                  30

Arg Pro Gly Tyr Arg Ser Leu Gly Asn Ile Ile Met Val Cys Arg Lys
            35                  40                  45

Gly Glu Trp Val Ala Leu Asn Pro Leu Arg Lys Cys Gln Lys Arg Pro
        50                  55                  60

<210> SEQ ID NO 74
<211> LENGTH: 63
<212> TYPE: PRT
<213> ORGANISM: Artificial Sequence
<220> FEATURE:
<223> OTHER INFORMATION: Chemically-synthesized amino acid sequence

<400> SEQUENCE: 74

Gly His Cys Gln Ala Pro Asp His Phe Leu Phe Ala Lys Leu Lys Thr
1               5                   10                  15

Gln Thr Asn Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
            35                  40                  45
```

-continued

Asn Leu Val Trp Ser Ser Pro Lys Asp Val Cys Lys Arg Lys Ser
    50                  55                  60

<210> SEQ ID NO 75
<211> LENGTH: 68
<212> TYPE: PRT
<213> ORGANISM: Artificial Sequence
<220> FEATURE:
<223> OTHER INFORMATION: Chemically-synthesized amino acid sequence

<400> SEQUENCE: 75

Ser Cys Cys Thr Ile Pro Ser Arg Pro Ile Asn Met Lys Phe Lys Asn
1               5                  10                  15

Ser Val Glu Thr Asp Ala Asn Ala Asn Tyr Asn Ile Gly Asp Thr Ile
            20                  25                  30

Glu Tyr Leu Cys Leu Pro Gly Tyr Arg Lys Gln Lys Met Met Gly Pro
        35                  40                  45

Ile Tyr Ala Lys Cys Thr Gly Thr Gly Trp Thr Leu Phe Asn Gln Cys
    50                  55                  60

Ile Lys Arg Arg
65

<210> SEQ ID NO 76
<211> LENGTH: 61
<212> TYPE: PRT
<213> ORGANISM: Artificial Sequence
<220> FEATURE:
<223> OTHER INFORMATION: Chemically-synthesized amino acid sequence

<400> SEQUENCE: 76

Cys Ser Gln Lys Thr Leu Ile Gly Tyr Arg Leu Lys Met Ser Arg Asp
1               5                  10                  15

Gly Asp Ile Ala Val Gly Glu Thr Val Glu Leu Arg Cys Arg Ser Gly
            20                  25                  30

Tyr Thr Thr Tyr Ala Arg Asn Ile Thr Ala Thr Cys Leu Gln Gly Gly
        35                  40                  45

Thr Trp Ser Glu Pro Thr Ala Thr Cys Asn Lys Lys Ser
    50                  55                  60

<210> SEQ ID NO 77
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 77

Ser Cys Pro Thr Arg Asn Gln Tyr Val Ser Val Lys Tyr Val Asn Leu
1               5                  10                  15

Thr Asn Tyr Ser Gln Pro Tyr Pro Asn Gln Thr Thr Leu His Val Thr
            20                  25                  30

Cys Arg Glu Gln Tyr Ala Lys Arg Pro Val Gln Thr Val Thr Cys Val
        35                  40                  45

Asn Gln Asn Trp Thr Val Pro Lys Lys Cys Gln Lys Lys Lys
    50                  55                  60

<210> SEQ ID NO 78
<211> LENGTH: 62
<212> TYPE: PRT
<213> ORGANISM: Artificial Sequence
<220> FEATURE:

<223> OTHER INFORMATION: Chemically-synthesized amino acid sequence

<400> SEQUENCE: 78

Cys Pro Asn Pro Gly Glu Ile Arg Asn Gly Gln Ile Asp Val Pro Gly
1               5                   10                  15

Gly Ile Leu Phe Gly Ala Thr Ile Ser Phe Ser Cys Asn Thr Gly Tyr
            20                  25                  30

Lys Leu Ile Gly Ser Thr Ser Ser Phe Cys Leu Ile Ser Gly Ser Ser
        35                  40                  45

Val Gln Trp Ser Asp Lys Leu Pro Ile Cys Glu Lys Val Leu
    50                  55                  60

<210> SEQ ID NO 79
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 79

Cys Pro Asn Pro Gly Glu Ile Arg Asn Gly Gln Ile Asp Val Pro Gly
1               5                   10                  15

Gly Ile Leu Phe Gly Ala Thr Ile Ser Phe Ser Cys Asn Thr Gly Tyr
            20                  25                  30

Lys Leu Phe Gly Ser Thr Ser Ser Phe Cys Leu Ile Ser Gly Ser Ser
        35                  40                  45

Val Gln Trp Ser Asp Pro Leu Pro Glu Cys Arg Glu Ile Tyr
    50                  55                  60

<210> SEQ ID NO 80
<211> LENGTH: 63
<212> TYPE: PRT
<213> ORGANISM: Artificial Sequence
<220> FEATURE:
<223> OTHER INFORMATION: Chemically-synthesized amino acid sequence

<400> SEQUENCE: 80

Cys Pro Tyr Ile Arg Asp Pro Leu Asn Gly Gln Ala Val Pro Ala Asn
1               5                   10                  15

Gly Thr Tyr Glu Phe Gly Tyr Gln Met His Phe Ile Cys Asn Glu Gly
            20                  25                  30

Tyr Tyr Leu Ile Gly Glu Glu Ile Leu Tyr Cys Glu Leu Lys Gly Ser
        35                  40                  45

Val Ala Ile Trp Ser Gly Lys Pro Pro Ile Cys Glu Lys Val Leu
    50                  55                  60

<210> SEQ ID NO 81
<211> LENGTH: 61
<212> TYPE: PRT
<213> ORGANISM: Artificial Sequence
<220> FEATURE:
<223> OTHER INFORMATION: Chemically-synthesized amino acid sequence

<400> SEQUENCE: 81

Cys Gly His Pro Gly Asp Thr Pro Phe Gly Thr Phe Thr Leu Thr Gly
1               5                   10                  15

Gly Asn Val Phe Glu Tyr Gly Val Lys Ala Val Tyr Thr Cys Asn Glu
            20                  25                  30

Gly Tyr Gln Leu Leu Gly Glu Ile Asn Tyr Arg Glu Cys Asp Thr Asp
        35                  40                  45

```
Gly Trp Thr Asn Asp Ile Pro Ile Cys Glu Val Val Lys
    50                  55                  60

<210> SEQ ID NO 82
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 82

Cys Lys Thr Pro Pro Asp Pro Val Asn Gly Met Val His Val Ile Thr
1               5                   10                  15

Asp Ile Gln Val Gly Ser Arg Ile Asn Tyr Ser Cys Thr Thr Gly His
            20                  25                  30

Arg Leu Ile Gly His Ser Ser Ala Glu Cys Ile Leu Ser Gly Asn Thr
        35                  40                  45

Ala His Trp Ser Thr Lys Pro Pro Ile Cys Gln Arg Ile Pro
    50                  55                  60

<210> SEQ ID NO 83
<211> LENGTH: 63
<212> TYPE: PRT
<213> ORGANISM: Artificial Sequence
<220> FEATURE:
<223> OTHER INFORMATION: Chemically-synthesized amino acid sequence

<400> SEQUENCE: 83

Cys Pro Ser Pro Arg Asp Ile Asp Asn Gly His His Leu Asp Ile Gly
1               5                   10                  15

Gly Val Asp Phe Gly Ser Ser Ile Thr Tyr Ser Cys Asn Ser Gly Tyr
            20                  25                  30

Tyr Leu Ile Gly Glu Tyr Lys Ser Tyr Cys Lys Leu Gly Ser Thr Gly
        35                  40                  45

Ser Met Val Trp Asn Pro Lys Ala Pro Ile Cys Glu Ser Val Lys
    50                  55                  60

<210> SEQ ID NO 84
<211> LENGTH: 67
<212> TYPE: PRT
<213> ORGANISM: Artificial Sequence
<220> FEATURE:
<223> OTHER INFORMATION: Chemically-synthesized amino acid sequence

<400> SEQUENCE: 84

Cys Pro Asn Pro Gly Glu Ile Gln Asn Gly Lys Val Ile Phe His Gly
1               5                   10                  15

Gly Gln Asp Ala Leu Lys Tyr Gly Ala Asn Ile Ser Tyr Val Cys Asn
            20                  25                  30

Glu Gly Tyr Phe Leu Val Gly Arg Glu Tyr Val Arg Tyr Cys Met Ile
        35                  40                  45

Gly Ala Ser Gly Gln Met Ala Trp Ser Ser Ser Pro Pro Phe Cys Glu
    50                  55                  60

Lys Glu Lys
65

<210> SEQ ID NO 85
<211> LENGTH: 63
<212> TYPE: PRT
<213> ORGANISM: Artificial Sequence
<220> FEATURE:
<223> OTHER INFORMATION: Chemically-synthesized amino acid sequence
```

<400> SEQUENCE: 85

Cys Ser Thr Pro Gln Asp Leu Leu Asn Gln Arg Tyr Thr Val Thr Gly
1               5                   10                  15

Asn Leu Tyr Tyr Gln Ser Val Ile Thr Tyr Thr Cys Asn Ser Gln Tyr
            20                  25                  30

Ser Leu Ile Gln Ser Thr Thr Ser Ala Cys Leu Leu Lys Arg Gly Gly
        35                  40                  45

Arg Val Asp Trp Thr Pro Arg Pro Pro Ile Cys Asp Ile Lys Lys
    50                  55                  60

<210> SEQ ID NO 86
<211> LENGTH: 66
<212> TYPE: PRT
<213> ORGANISM: Artificial Sequence
<220> FEATURE:
<223> OTHER INFORMATION: Chemically-synthesized amino acid sequence

<400> SEQUENCE: 86

Cys Thr Pro Pro Pro Lys Ile Lys Asn Gly Lys His Thr Phe Ser Glu
1               5                   10                  15

Val Glu Val Phe Glu Tyr Leu Asp Ala Val Thr Tyr Ser Cys Asp Pro
            20                  25                  30

Ala Pro Gly Pro Asp Pro Phe Ser Leu Ile Gly Glu Ser Thr Ile Tyr
        35                  40                  45

Cys Gly Asp Asn Ser Val Trp Ser Arg Ala Ala Pro Glu Cys Lys Val
    50                  55                  60

Val Lys
65

<210> SEQ ID NO 87
<211> LENGTH: 62
<212> TYPE: PRT
<213> ORGANISM: Artificial Sequence
<220> FEATURE:
<223> OTHER INFORMATION: Chemically-synthesized amino acid sequence

<400> SEQUENCE: 87

Cys Pro Ala Pro Pro Gln Ile Asp Asn Gly Ile Ile Gln Gly Glu Arg
1               5                   10                  15

Asp His Tyr Gly Tyr Arg Gln Ser Val Thr Tyr Ala Cys Asn Lys Gly
            20                  25                  30

Phe Thr Met Ile Gly Glu His Ser Ile Tyr Cys Thr Val Asn Asn Asp
        35                  40                  45

Glu Gly Glu Trp Ser Gly Pro Pro Pro Glu Cys Arg Gly Cys
    50                  55                  60

<210> SEQ ID NO 88
<211> LENGTH: 66
<212> TYPE: PRT
<213> ORGANISM: Artificial Sequence
<220> FEATURE:
<223> OTHER INFORMATION: Chemically-synthesized amino acid sequence

<400> SEQUENCE: 88

Cys Thr Pro Pro Pro Lys Ile Lys Asn Gly Lys His Thr Phe Ser Glu
1               5                   10                  15

Val Glu Val Phe Glu Tyr Leu Asp Ala Val Thr Tyr Ser Cys Asp Pro
            20                  25                  30

Ala Pro Gly Pro Asp Pro Phe Ser Leu Ile Gly Glu Ser Thr Ile Tyr

-continued

```
              35                  40                  45

Cys Gly Asp Asn Ser Val Trp Ser Arg Ala Ala Pro Glu Cys Lys Val
    50                  55                  60

Val Lys
65

<210> SEQ ID NO 89
<211> LENGTH: 64
<212> TYPE: PRT
<213> ORGANISM: Artificial Sequence
<220> FEATURE:
<223> OTHER INFORMATION: Chemically-synthesized amino acid sequence

<400> SEQUENCE: 89

Cys Leu Pro Val Thr Ala Pro Glu Asn Gly Lys Ile Val Ser Ser Ala
1               5                   10                  15

Met Glu Pro Asp Arg Glu Tyr His Phe Gly Gln Ala Val Arg Phe Val
                20                  25                  30

Cys Asn Ser Gly Tyr Lys Ile Glu Gly Asp Glu Glu Met His Cys Ser
        35                  40                  45

Asp Asp Gly Phe Trp Ser Lys Glu Lys Pro Lys Cys Val Glu Ile Ser
    50                  55                  60

<210> SEQ ID NO 90
<211> LENGTH: 68
<212> TYPE: PRT
<213> ORGANISM: Artificial Sequence
<220> FEATURE:
<223> OTHER INFORMATION: Chemically-synthesized amino acid sequence

<400> SEQUENCE: 90

Cys Gly Leu Pro Pro Thr Ile Ala Asn Gly Asp Phe Ile Ser Thr Asn
1               5                   10                  15

Arg Glu Asn Phe His Tyr Gly Ser Val Val Thr Tyr Arg Cys Asn Leu
                20                  25                  30

Gly Ser Arg Gly Arg Lys Val Phe Glu Leu Val Gly Glu Pro Ser Ile
        35                  40                  45

Tyr Cys Thr Ser Asn Asp Asp Gln Val Gly Ile Trp Ser Gly Pro Ala
    50                  55                  60

Pro Gln Cys Ile
65

<210> SEQ ID NO 91
<211> LENGTH: 58
<212> TYPE: PRT
<213> ORGANISM: Artificial Sequence
<220> FEATURE:
<223> OTHER INFORMATION: Chemically-synthesized amino acid sequence

<400> SEQUENCE: 91

Cys Gln Leu Pro Pro Ser Ile Ser Asn Gly Arg His Asn Gly Tyr Asn
1               5                   10                  15

Asp Phe Tyr Thr Asp Gly Ser Val Val Thr Tyr Ser Cys Asn Ser Gly
                20                  25                  30

Tyr Ser Leu Ile Gly Asn Ser Gly Val Leu Cys Ser Gly Gly Glu Trp
        35                  40                  45

Ser Asn Pro Pro Thr Cys Gln Ile Val Lys
    50                  55

<210> SEQ ID NO 92
```

```
<211> LENGTH: 59
<212> TYPE: PRT
<213> ORGANISM: Artificial Sequence
<220> FEATURE:
<223> OTHER INFORMATION: Chemically-synthesized amino acid sequence

<400> SEQUENCE: 92

Cys His Arg Pro Lys Ile Glu Asn Gly Asp Phe Lys Pro Asp Lys Asp
1               5                   10                  15

Tyr Tyr Glu Tyr Asn Asp Ala Val His Phe Glu Cys Asn Glu Gly Tyr
                20                  25                  30

Thr Leu Val Gly Pro His Ser Ile Ala Cys Ala Val Asn Asn Thr Trp
            35                  40                  45

Thr Ser Asn Met Pro Thr Cys Glu Leu Ala Gly
        50                  55

<210> SEQ ID NO 93
<211> LENGTH: 63
<212> TYPE: PRT
<213> ORGANISM: Artificial Sequence
<220> FEATURE:
<223> OTHER INFORMATION: Chemically-synthesized amino acid sequence

<400> SEQUENCE: 93

Cys Lys Pro Pro Pro Gln Ile Ala Asn Gln Thr His Thr Asn Val Lys
1               5                   10                  15

Asp Phe Tyr Thr Tyr Leu Asp Thr Val Thr Tyr Ser Cys Asn Asp Glu
                20                  25                  30

Thr Lys Leu Thr Leu Thr Gln Pro Ser Ser Lys Leu Cys Ser Glu Thr
            35                  40                  45

Gly Ser Trp Val Pro Asn Gly Glu Thr Lys Cys Glu Phe Ile Phe
        50                  55                  60

<210> SEQ ID NO 94
<211> LENGTH: 60
<212> TYPE: PRT
<213> ORGANISM: Artificial Sequence
<220> FEATURE:
<223> OTHER INFORMATION: Chemically-synthesized amino acid sequence

<400> SEQUENCE: 94

Cys Arg Phe Pro Val Val Glu Asn Gly Lys Gln Ile Ser Gly Phe Gly
1               5                   10                  15

Lys Lys Phe Tyr Tyr Lys Ala Thr Val Met Phe Glu Cys Asp Lys Gly
                20                  25                  30

Phe Tyr Leu Asp Gly Ser Asp Thr Ile Val Cys Asp Ser Asn Ser Thr
            35                  40                  45

Trp Asp Pro Pro Val Pro Lys Cys Leu Lys Val Leu
        50                  55                  60

<210> SEQ ID NO 95
<211> LENGTH: 59
<212> TYPE: PRT
<213> ORGANISM: Artificial Sequence
<220> FEATURE:
<223> OTHER INFORMATION: Chemically-synthesized amino acid sequence

<400> SEQUENCE: 95

Cys Arg Phe Pro Val Val Glu Asn Gly Lys Gln Ile Ser Gly Phe Gly
1               5                   10                  15

Lys Lys Phe Tyr Tyr Lys Ala Thr Val Met Phe Glu Cys Asp Lys Gly
                20                  25                  30
```

105 106

-continued

```
Phe Tyr Leu Asp Gly Ser Asp Thr Ile Val Cys Asp Ser Asn Ser Thr
        35                  40                  45

Trp Asp Pro Pro Val Pro Lys Cys Leu Lys Val
        50                  55

<210> SEQ ID NO 96
<211> LENGTH: 56
<212> TYPE: PRT
<213> ORGANISM: Artificial Sequence
<220> FEATURE:
<223> OTHER INFORMATION: Chemically-synthesized amino acid sequence

<400> SEQUENCE: 96

Cys Lys Ser Pro Asp Val Ile Asn Gly Ser Pro Ile Ser Gln Lys Ile
1               5                   10                  15

Ile Tyr Lys Glu Asn Glu Arg Phe Gln Tyr Lys Cys Asn Met Gly Tyr
            20                  25                  30

Glu Tyr Ser Glu Arg Gly Asp Ala Val Cys Thr Glu Ser Gly Trp Arg
        35                  40                  45

Pro Leu Pro Ser Cys Glu Glu Ala
    50                  55

<210> SEQ ID NO 97
<211> LENGTH: 53
<212> TYPE: PRT
<213> ORGANISM: Artificial Sequence
<220> FEATURE:
<223> OTHER INFORMATION: Chemically-synthesized amino acid sequence

<400> SEQUENCE: 97

Cys Pro His Pro Thr Ile Leu Asn Gly Tyr Leu Ser Ser Gly Phe Lys
1               5                   10                  15

Arg Ser Tyr Ser Tyr Asn Asp Asn Val Asp Phe Thr Cys Lys Tyr Gly
            20                  25                  30

Tyr Lys Leu Ser Gly Ser Ser Ser Thr Cys Ser Pro Gly Asn Thr
        35                  40                  45

Trp Gln Pro Glu Leu
    50

<210> SEQ ID NO 98
<211> LENGTH: 59
<212> TYPE: PRT
<213> ORGANISM: Artificial Sequence
<220> FEATURE:
<223> OTHER INFORMATION: Chemically-synthesized amino acid sequence

<400> SEQUENCE: 98

Cys Lys Phe Pro Ser Val Thr His Gly Tyr Pro Ile Gln Gly Phe Ser
1               5                   10                  15

Leu Thr Tyr Lys His Lys Gln Ser Val Thr Phe Ala Cys Asn Asp Gly
            20                  25                  30

Phe Val Leu Arg Gly Ser Pro Thr Ile Thr Cys Asn Val Thr Glu Trp
        35                  40                  45

Asp Pro Pro Leu Pro Lys Cys Val Leu Glu Asp
    50                  55

<210> SEQ ID NO 99
<211> LENGTH: 56
<212> TYPE: PRT
<213> ORGANISM: Artificial Sequence
<220> FEATURE:
```

```
<223> OTHER INFORMATION: Chemically-synthesized amino acid sequence

<400> SEQUENCE: 99

Cys Lys Leu Pro Gln Val Ala Asn Ala Tyr Val Glu Val Arg Lys Ser
1               5                   10                  15

Ala Thr Ser Met Gln Tyr Leu His Ile Asn Val Lys Cys Tyr Lys Gly
            20                  25                  30

Phe Met Leu Tyr Gln Glu Thr Pro Asn Thr Cys Asn His Gln Val Trp
        35                  40                  45

Ser Pro Ala Ile Pro Glu Cys Met
    50                  55

<210> SEQ ID NO 100
<211> LENGTH: 6
<212> TYPE: PRT
<213> ORGANISM: Artificial Sequence
<220> FEATURE:
<223> OTHER INFORMATION: Chemically-synthesized amino acid sequence

<400> SEQUENCE: 100

Glu Cys Arg Glu Ile Tyr
1               5

<210> SEQ ID NO 101
<211> LENGTH: 6
<212> TYPE: PRT
<213> ORGANISM: Artificial Sequence
<220> FEATURE:
<223> OTHER INFORMATION: Chemically-synthesized amino acid sequence

<400> SEQUENCE: 101

Ile Cys Glu Lys Val Leu
1               5
```